(12) United States Patent
Junutula et al.

(10) Patent No.: US 7,723,485 B2
(45) Date of Patent: *May 25, 2010

(54) CYSTEINE ENGINEERED ANTI-MUC16 ANTIBODIES AND ANTIBODY DRUG CONJUGATES

(75) Inventors: Jagath R. Junutula, Fremont, CA (US); William Mallet, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/116,457

(22) Filed: May 7, 2008

(65) Prior Publication Data

US 2008/0311134 A1 Dec. 18, 2008

Related U.S. Application Data

(60) Provisional application No. 60/916,657, filed on May 8, 2007.

(51) Int. Cl.
| | |
|---|---|
| C07K 16/00 | (2006.01) |
| C12P 21/08 | (2006.01) |
| C07K 17/00 | (2006.01) |
| C07K 17/14 | (2006.01) |
| A61K 39/395 | (2006.01) |
| A61K 39/00 | (2006.01) |
| G01N 33/53 | (2006.01) |
| G01N 33/574 | (2006.01) |
| C12P 21/04 | (2006.01) |

(52) U.S. Cl. ............... 530/387.1; 530/387.3; 530/387.7; 530/388.15; 530/391.1; 424/130.1; 424/178.1; 424/134.1; 424/181.1; 435/69.6; 435/7.1; 435/7.23

(58) Field of Classification Search ........................ None
See application file for complete search history.

(56) References Cited

U.S. PATENT DOCUMENTS

| | | | |
|---|---|---|---|
| 5,219,996 | A | 6/1993 | Bodmer et al. |
| 6,753,165 | B1 | 6/2004 | Cox et al. |
| 6,858,710 | B2 | 2/2005 | Bangur et al. |
| 7,521,541 | B2 * | 4/2009 | Eigenbrot et al. ........ 530/387.1 |
| 2003/0078399 | A1 | 4/2003 | Lloyd et al. |
| 2004/0057952 | A1 | 3/2004 | Payne et al. |
| 2004/0126378 | A1 | 7/2004 | Fanger et al. |
| 2005/0064518 | A1 | 3/2005 | Albone et al. |
| 2005/0238649 | A1 | 10/2005 | Doronina et al. |
| 2005/0276812 | A1 | 12/2005 | Ebens et al. |
| 2007/0092940 | A1 | 4/2007 | Eigenbrot et al. |
| 2009/0175865 | A1 * | 7/2009 | Eigenbrot et al. ........ 424/133.1 |

FOREIGN PATENT DOCUMENTS

| | | | |
|---|---|---|---|
| WO | 2005/081711 | A2 | 9/2005 |
| WO | 2006/034488 | A2 | 3/2006 |
| WO | 2006/132670 | A2 | 12/2006 |
| WO | 2007/001851 | A2 | 4/2007 |

OTHER PUBLICATIONS

Bernhard et al, "Cysteine analogs of recombinant barley ribsome inactivating protein from antibody conjugates with enhanced stability and potency in vitro" *Bionjug Chem.* 5(2):126-32 (1994).
Better et al., "Gelonin analogs with engineered cysteine residues form antibody immunoconjugates with unique properties" *J Biol Chem.* 269(13):9644-50 (Apr. 1, 1994).
Chen et al., "Armed antibodies targeting the mucin repeats of the ovarian cancer antigen, MUC16, are highly efficacious in animal tumor models" *Cancer Research* 67(10):4924-32 (May 15, 2007).
Corneillie et al, "Converting Weak Binders into Infinite Binders" *Bioconjugate Chem.* 15(6):1389-1391 (2004).
Hafner et al., "Noncompetitive Immunoassay of Small Analytes at the Femtolar Level by Affinity Probe Capillary Electrophoresis: Direct Analysis of Digoxin Using a Uniform-Labeled scFv Immunoreagent" *Anal. Chem* 72(23):5779-5786 (Dec. 1, 2000).
Junutula et al., "Rapid identification of reactive cysteine residues for site-specific labeling of antibody-Fabs" *J Immunol Methods* 332:41-52 (2008).
Junutula et al., "Site-specific conjugation of a cytotoxic drug to an antibody improves the therapeutic index" *Nat Biotechnol.* 26(8):925-32 (Aug. 2008).
McDonagh et al., "Engineered antibody-drug conjugates with defined sites and stoichiometries of drug attachment" *Protein Eng Des Sel.* 19(7):299-307 (2006).
Renard et al., "Deriving Topological Contraints from Functional Data for the Design of Reagentless Fluorescent Immunosensors" *J. Mol. Biol.* 326:167-175 (2003).
Shopes, "A Genetically Engineered Human IgG With Limited Flexibility Fully Initiates Cytolysis Via Complement" *Molecular Immunology* 30(6):603-609 (1993).
Singleton et al., "Characterization of antibodies to CA 125 that bind preferentially to the cell-associated form of the antigen" *Tumour Biol.* 27:122-32 (2006).
Stimmel et al., "Site-specific Conjugation on Serin—Cysteine Variant Monoclonal Antibodies" *Journal of Biological Chemistry* 275(39):30445-50 (Sep. 29, 2000).

* cited by examiner

*Primary Examiner*—Larry R. Helms
*Assistant Examiner*—Anne M. Gussow
(74) *Attorney, Agent, or Firm*—Alex Andrus

(57) ABSTRACT

Cysteine engineered anti-MUC16 antibodies are engineered by replacing one or more amino acids of a parent anti-MUC16 antibody with non cross-linked, reactive cysteine amino acids. Methods of design, preparation, screening, and selection of the cysteine engineered anti-MUC16 antibodies are provided. Cysteine engineered anti-MUC16 antibodies (Ab) are conjugated with one or more drug moieties (D) through a linker (L) to form cysteine engineered anti-MUC16 antibody-drug conjugates having Formula I:

$$Ab\text{-}(L\text{-}D)_p \quad \quad I$$

where p is 1 to 4. Diagnostic and therapeutic uses for cysteine engineered antibody drug compounds and compositions are disclosed.

40 Claims, 21 Drawing Sheets

EVQLVESGGGLVQPGGSLRLSCAASGYSITNDYAWNWVRQAPGKGLEWVGYISYSGYTTY
NPSLKSRFTISRDTSKNTLYLQMNSLRAEDTAVYYCARWTSGLDYWGQGTLVTVSSCSTK
GPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK                              SEQ ID NO:1

DIQMTQSPSSLSASVGDRVTITCKASDLIHNWLAWYQQKPGKAPKLLIYGATSLETGVPS
RFSGSGSGTDFTLTISSLQPEDFATYYCQQYWTTPFTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC                      SEQ ID NO:2

Figure 1

DVQLQESGPGLVNPSQSLSLTCTVTGYSITNDYAWNWIRQFPGNKLEWMGYINYSGYTTY
NPSLKSRISITRDTSKNQFFLHLNSVTTEDTATYYCARWDGGLTYWGQGTLVTVSACSTK
GPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK                              SEQ ID NO:3

DIQMTQSSSFLSVSLGGRVTITCKASDLIHNWLAWYQQKPGNAPRLLISGATSLETGVPS
RFSGSGSGNDYTLSIASLQTEDAATYYCQQYWTTPFTFGSGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC                      SEQ ID NO:4

Figure 2

Humanized Trastuzumab light chain sequence alignment with humanized and chimeric 3A5 (anti-MUC16 ab) light chain

```
HuTMAb-LC    1    DIQMTQSPSSLSASVGDRVTITCRASQDVNTAVAWYQQKPGKAPKLLIYS          50
Hu3A5-LC     1    DIQMTQSPSSLSASVGDRVTITCKASDLIHNWLAWYQQKPGKAPKLLIYG          50
Ch3A5-LC     1    DIQMTQSSSFLSVSLGGRVTITCKASDLIHNWLAWYQQKPGNAPRLLISG          50
                                 15

HuTMAb-LC   51    ASFLYSGVPSRFSGSRSGTDFTLTISSLQPEDFATYYCQQHYTTPPTFGQ         100
Hu3A5-LC    51    ATSLETGVPSRFSGSGSGTDFTLTISSLQPEDFATYYCQQYWTTPFTFGQ         100
Ch3A5-LC    51    ATSLETGVPSRFSGSGSGNDYTLSIASLQTEDAATYYCQQYWTTPFTFGS         100

HuTMAb-LC  101    GTKVEIKRTVAAPSVFIFPPSDEQLKSGTASVVCLLNNFYPREAKVQWKV         150
Hu3A5-LC   101    GTKVEIKRTVAAPSVFIFPPSDEQLKSGTASVVCLLNNFYPREAKVQWKV         150
Ch3A5-LC   101    GTKVEIKRTVAAPSVFIFPPSDEQLKSGTASVVCLLNNFYPREAKVQWKV         150
                           110   114         121      127

HuTMAb-LC  151    DNALQSGNSQESVTEQDSKDSTYSLSSTLTLSKADYEKHKVYACEVTHQG         200
Hu3A5-LC   151    DNALQSGNSQESVTEQDSKDSTYSLSSTLTLSKADYEKHKVYACEVTHQG         200
Ch3A5-LC   151    DNALQSGNSQESVTEQDSKDSTYSLSSTLTLSKADYEKHKVYACEVTHQG         200
                                  168

HuTMAb-LC  201    LSSPVTKSFNRGEC      214              HuTMAb-LC    SEQ ID NO:5
Hu3A5-LC   201    LSSPVTKSFNRGEC      214              Hu3A5-LC     SEQ ID NO:2
Ch3A5-LC   201    LSSPVTKSFNRGEC      214              Ch3A5-LC     SEQ ID NO:4
                      205
```

The numbering denotes for 3A5 light chain according to sequential numbering

FIG. 3

Humanized Trastuzumab heavy chain sequence alignment with
humanized and chimeric 3A5 (anti-MUC16 ab) heavy chain

```
HuTMAb-HC    1  EVQLVESGGGLVQPGGSLRLSCAASGFNIKDTYIH-WVRQAPGKGLEWVA              49
Hu3A5-HC     1  EVQLVESGGGLVQPGGSLRLSCAASGYSITNDYAWNWVRQAPGKGLEWVG              50
Ch3A5-HC     1  DVQLQESGPGLVNPSQSLSLTCTVTGYSITNDYAWNWIRQFPGNKLEWMG              50
                     5                              23

Hu3A5-HC    50  RIYPTNGYTRYADSVKGRFTISADTSKNTAYLQMNSLRAEDTAVYYCSRW              99
Hu3A5-HC    51  YISYS-GYTTYNPSLKSRFTISRDTSKNTLYLQMNSLRAEDTAVYYCARW              99
Ch3A5-HC    51  YINYS-GYTTYNPSLKSRISITRDTSKNQFFLHLNSVTTEDTATYYCARW              99
                                                         88

Hu3A5-HC   100  GGDGFYAMDYWGQGTLVTVSSASTKGPSVFPLAPSSKSTSGGTAALGCLV             149
Hu3A5-HC   100  TSG----LDYWGQGTLVTVSSASTKGPSVFPLAPSSKSTSGGTAALGCLV             145
Ch3A5-HC   100  DGG----LIYWGQGILVIVSAASIKGPSVFPLAPSSKSISGGIAALGCLV             145
                                     115 117 119

Hu3A5-HC   150  KDYFPEPVTVSWNSGALTSGVHTFPAVLQSSGLYSLSSVVTVPSSSLGTQ             199
Hu3A5-HC   146  KDYFPEPVTVSWNSGALTSGVHTFPAVLQSSGLYSLSSVVTVPSSSLGTQ             195
Ch3A5-HC   146  KDYFPEPVTVSWNSGALTSGVHTFPAVLQSSGLYSLSSVVTVPSSSLGTQ             195

Hu3A5-HC   200  TYICNVNHKPSNTKVDKKVEPKSCDKTHTCPPCPAPELLGGPSVFLFPPK             249
Hu3A5-HC   196  TYICNVNHKPSNTKVDKKVEPKSCDKTHTCPPCPAPELLGGPSVFLFPPK             245
Ch3A5-HC   196  TYICNVNHKPSNTKVDKKVEPKSCDKTHTCPPCPAPELLGGPSVFLFPPK             245

Hu3A5-HC   250  PKDTLMISRTPEVTCVVVDVSHEDPEVKFNWYVDGVEVHNAKTKPREEQY             299
Hu3A5-HC   246  PKDTLMISRTPEVTCVVVDVSHEDPEVKFNWYVDGVEVHNAKTKPREEQY             295
Ch3A5-HC   246  PKDTLMISRTPEVTCVVVDVSHEDPEVKFNWYVDGVEVHNAKTKPREEQY             295
                                                          281
```

FIG. 3 CONTINUED

| | | |
|---|---|---|
| 300 | NSTYRVVSVLTVLHQDWLNGKEYKCKVSNKALPAPIEKTISKAKGQPREP | 349 |
| 296 | NSTYRVVSVLTVLHQDWLNGKEYKCKVSNKALPAPIEKTISKAKGQPREP | 345 |
| 296 | NSTYRVVSVLTVLHQDWLNGKEYKCKVSNKALPAPIEKTISKAKGQPREP | 345 |
| 350 | QVYTLPPSREEMTKNQVSLTCLVKGFYPSDIAVEWESNGQPENNYKTTPP | 399 |
| 346 | QVYTLPPSREEMTKNQVSLTCLVKGFYPSDIAVEWESNGQPENNYKTTPP | 395 |
| 346 | QVYTLPPSREEMTKNQVSLTCLVKGFYPSDIAVEWESNGQPENNYKTTPP | 395 |
| | 374 | |
| 400 | VLDSDGSFFLYSKLTVDKSRWQQGNVFSCSVMHEALHNHYTQKSLSLSPG | 449 |
| 396 | VLDSDGSFFLYSKLTVDKSRWQQGNVFSCSVMHEALHNHYTQKSLSLSPG | 445 |
| 396 | VLDSDGSFFLYSKLTVDKSRWQQGNVFSCSVMHEALHNHYTQKSLSLSPG | 445 |
| | 399 | |
| 450 | K | 450 |
| 446 | K | 446 |
| 446 | K | 446 |

HuTMAb-HC    SEQ ID NO:6
Hu3A5-HC     SEQ ID NO:7
Ch3A5-HC     SEQ ID NO:8

The numbering denotes for 3A5 heavy chain according to sequential numbering

FIG. 4

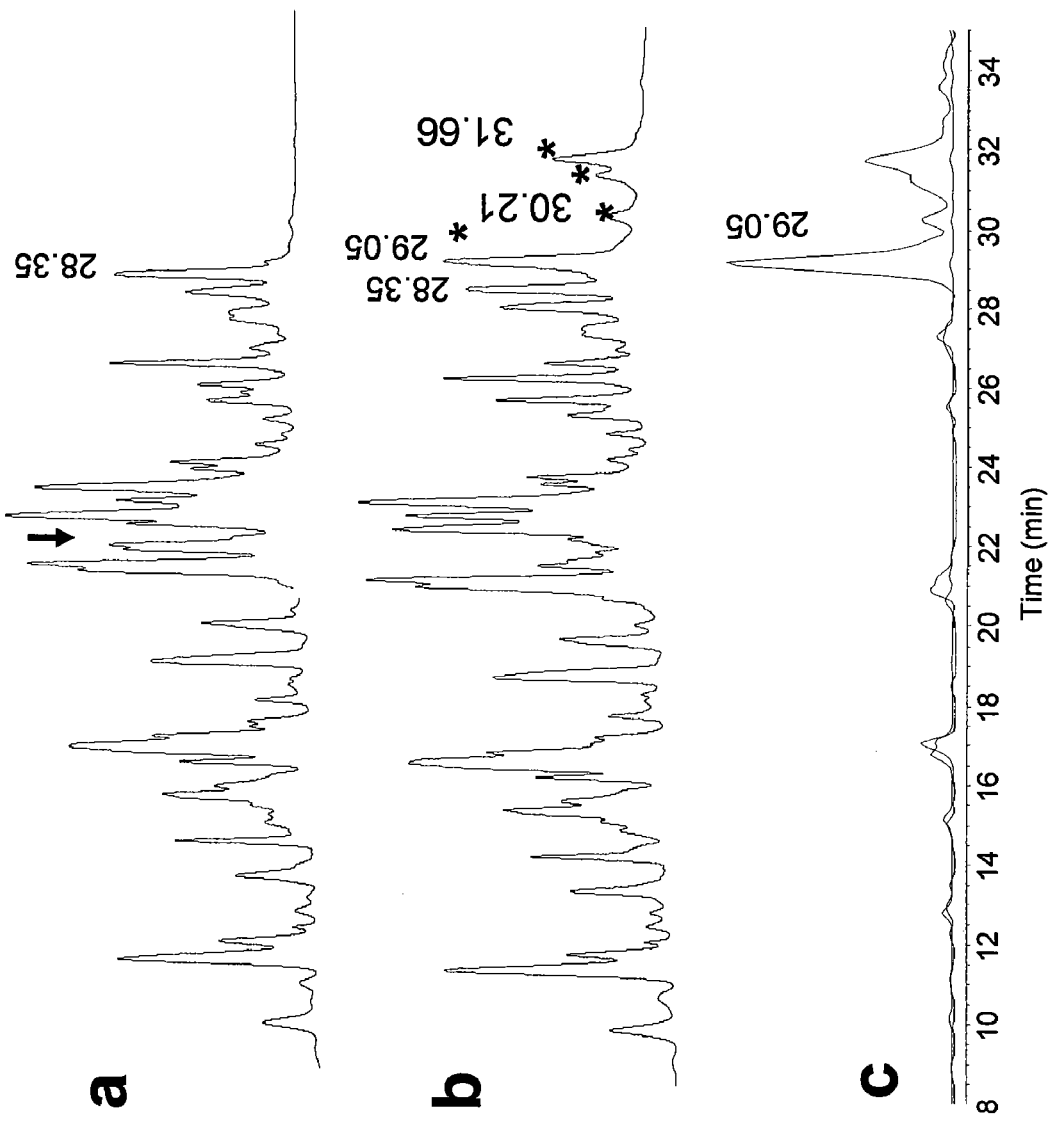

| Conjugated antibody | REDUCTION (DTT) | INTACT |
|---|---|---|
| Std Hu 3A5-VC-MMAE 3.5 drugs per IgG | LC<br>LC + 1 MCvcPAB-MMAE<br>LC+ 1 MCvcPAB<br>HC<br>HC + 1 MCvcPAB-MMAE<br>HC + 2 MCvcPAB-MMAE<br>HC + 3 MCvcPAB-MMAE | LC + 1 MCvc<br>LC + 1 MCvcPAB<br>LC + 1 MCvcPAB-MMAE<br>HC + 1 MCvcPAB-MMAE<br>HC + 3 MCvcPAB-MMAE<br>LC/HC + 2 MCvcPAB-MMAE<br>2 HC + 2 MCvcPAB-MMAE<br>LC/2HC + 1 MCvcPAB-MMAE |
| Thio Hu3A5-VC-MMAE 1.9 drugs per IgG | LC<br>HC<br>HC + 1 MCvcPAB-MMAE | Intact + 2 MCvcPAB-MMAE |
| Thio Hu3A5-VC-MMAE 1.6 drugs per IgG | LC<br>HC<br>HC + 1 MCvcPAB-MMAE | Intact + 2 MCvcPAB-MMAE<br>Intact + 1 MCvcPAB-MMAE<br>+ 1 MCvc |

FIG. 9

SEQUENCE LISTING

```
<160> NUMBER OF SEQ ID NOS: 42

<210> SEQ ID NO 1
<211> LENGTH: 446
<212> TYPE: PRT
<213> ORGANISM: Artificial sequence
<220> FEATURE:
<223> OTHER INFORMATION: chemically synthesized

<400> SEQUENCE: 1

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Ile Thr
                20                  25                  30

Asn Asp Tyr Ala Trp Asn Trp Val Arg Gln Ala Pro Gly Lys Gly
                35                  40                  45

Leu Glu Trp Val Gly Tyr Ile Ser Tyr Ser Gly Tyr Thr Thr Tyr
                50                  55                  60

Asn Pro Ser Leu Lys Ser Arg Phe Thr Ile Ser Arg Asp Thr Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Trp Thr Ser Gly Leu Asp Tyr
                95                 100                 105

Trp Gly Gln Gly Thr Leu Val Thr Val Ser Ser Cys Ser Thr Lys
               110                 115                 120

Gly Pro Ser Val Phe Pro Leu Ala Pro Ser Ser Lys Ser Thr Ser
               125                 130                 135

Gly Gly Thr Ala Ala Leu Gly Cys Leu Val Lys Asp Tyr Phe Pro
               140                 145                 150

Glu Pro Val Thr Val Ser Trp Asn Ser Gly Ala Leu Thr Ser Gly
               155                 160                 165

Val His Thr Phe Pro Ala Val Leu Gln Ser Ser Gly Leu Tyr Ser
               170                 175                 180

Leu Ser Ser Val Val Thr Val Pro Ser Ser Ser Leu Gly Thr Gln
               185                 190                 195
```

```
Thr Tyr Ile Cys Asn Val Asn His Lys Pro Ser Asn Thr Lys Val
                200                 205                 210

Asp Lys Lys Val Glu Pro Lys Ser Cys Asp Lys Thr His Thr Cys
                215                 220                 225

Pro Pro Cys Pro Ala Pro Glu Leu Leu Gly Gly Pro Ser Val Phe
                230                 235                 240

Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro
                260                 265                 270

Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly
                305                 310                 315

Lys Glu Tyr Lys Cys Lys Val Ser Asn Lys Ala Leu Pro Ala Pro
                320                 325                 330

Ile Glu Lys Thr Ile Ser Lys Ala Lys Gly Gln Pro Arg Glu Pro
                335                 340                 345

Gln Val Tyr Thr Leu Pro Pro Ser Arg Glu Glu Met Thr Lys Asn
                350                 355                 360

Gln Val Ser Leu Thr Cys Leu Val Lys Gly Phe Tyr Pro Ser Asp
                365                 370                 375

Ile Ala Val Glu Trp Glu Ser Asn Gly Gln Pro Glu Asn Asn Tyr
                380                 385                 390

Lys Thr Thr Pro Pro Val Leu Asp Ser Asp Gly Ser Phe Phe Leu
                395                 400                 405

Tyr Ser Lys Leu Thr Val Asp Lys Ser Arg Trp Gln Gln Gly Asn
                410                 415                 420

Val Phe Ser Cys Ser Val Met His Glu Ala Leu His Asn His Tyr
                425                 430                 435

Thr Gln Lys Ser Leu Ser Leu Ser Pro Gly Lys
                440                 445

<210> SEQ ID NO 2
<211> LENGTH: 214
<212> TYPE: PRT
<213> ORGANISM: Artificial sequence
<220> FEATURE:
<223> OTHER INFORMATION: chemically synthesized

<400> SEQUENCE: 2

Asp Ile Gln Met Thr Gln Ser Pro Ser Ser Leu Ser Ala Ser Val
 1               5                  10                  15

Gly Asp Arg Val Thr Ile Thr Cys Lys Ala Ser Asp Leu Ile His
                20                  25                  30

Asn Trp Leu Ala Trp Tyr Gln Gln Lys Pro Gly Lys Ala Pro Lys
                35                  40                  45

Leu Leu Ile Tyr Gly Ala Thr Ser Leu Glu Thr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90
```

```
Tyr Trp Thr Thr Pro Phe Thr Phe Gly Gln Gly Thr Lys Val Glu
                95                 100                 105

Ile Lys Arg Thr Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
               155                 160                 165

Gln Asp Ser Lys Asp Ser Thr Tyr Ser Leu Ser Ser Thr Leu Thr
               170                 175                 180

Leu Ser Lys Ala Asp Tyr Glu Lys His Lys Val Tyr Ala Cys Glu
               185                 190                 195

Val Thr His Gln Gly Leu Ser Ser Pro Val Thr Lys Ser Phe Asn
               200                 205                 210

Arg Gly Glu Cys

<210> SEQ ID NO 3
<211> LENGTH: 446
<212> TYPE: PRT
<213> ORGANISM: Artificial sequence
<220> FEATURE:
<223> OTHER INFORMATION: chemically synthesized

<400> SEQUENCE: 3

Asp Val Gln Leu Gln Glu Ser Gly Pro Gly Leu Val Asn Pro Ser
 1               5                  10                  15

Gln Ser Leu Ser Leu Thr Cys Thr Val Thr Gly Tyr Ser Ile Thr
                20                  25                  30

Asn Asp Tyr Ala Trp Asn Trp Ile Arg Gln Phe Pro Gly Asn Lys
                35                  40                  45

Leu Glu Trp Met Gly Tyr Ile Asn Tyr Ser Gly Tyr Thr Thr Tyr
                50                  55                  60

Asn Pro Ser Leu Lys Ser Arg Ile Ser Ile Thr Arg Asp Thr Ser
                65                  70                  75

Lys Asn Gln Phe Phe Leu His Leu Asn Ser Val Thr Thr Glu Asp
                80                  85                  90

Thr Ala Thr Tyr Tyr Cys Ala Arg Trp Asp Gly Gly Leu Thr Tyr
                95                 100                 105

Trp Gly Gln Gly Thr Leu Val Thr Val Ser Ala Cys Ser Thr Lys
               110                 115                 120

Gly Pro Ser Val Phe Pro Leu Ala Pro Ser Ser Lys Ser Thr Ser
               125                 130                 135

Gly Gly Thr Ala Ala Leu Gly Cys Leu Val Lys Asp Tyr Phe Pro
               140                 145                 150

Glu Pro Val Thr Val Ser Trp Asn Ser Gly Ala Leu Thr Ser Gly
               155                 160                 165

Val His Thr Phe Pro Ala Val Leu Gln Ser Ser Gly Leu Tyr Ser
               170                 175                 180

Leu Ser Ser Val Val Thr Val Pro Ser Ser Ser Leu Gly Thr Gln
               185                 190                 195

Thr Tyr Ile Cys Asn Val Asn His Lys Pro Ser Asn Thr Lys Val
               200                 205                 210
```

-continued

```
Asp Lys Lys Val Glu Pro Lys Ser Cys Asp Lys Thr His Thr Cys
            215                 220                 225

Pro Pro Cys Pro Ala Pro Glu Leu Leu Gly Gly Pro Ser Val Phe
            230                 235                 240

Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro
            260                 265                 270

Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly
            305                 310                 315

Lys Glu Tyr Lys Cys Lys Val Ser Asn Lys Ala Leu Pro Ala Pro
            320                 325                 330

Ile Glu Lys Thr Ile Ser Lys Ala Lys Gly Gln Pro Arg Glu Pro
            335                 340                 345

Gln Val Tyr Thr Leu Pro Pro Ser Arg Glu Glu Met Thr Lys Asn
            350                 355                 360

Gln Val Ser Leu Thr Cys Leu Val Lys Gly Phe Tyr Pro Ser Asp
            365                 370                 375

Ile Ala Val Glu Trp Glu Ser Asn Gly Gln Pro Glu Asn Asn Tyr
            380                 385                 390

Lys Thr Thr Pro Pro Val Leu Asp Ser Asp Gly Ser Phe Phe Leu
            395                 400                 405

Tyr Ser Lys Leu Thr Val Asp Lys Ser Arg Trp Gln Gln Gly Asn
            410                 415                 420

Val Phe Ser Cys Ser Val Met His Glu Ala Leu His Asn His Tyr
            425                 430                 435

Thr Gln Lys Ser Leu Ser Leu Ser Pro Gly Lys
            440                 445

<210> SEQ ID NO 4
<211> LENGTH: 214
<212> TYPE: PRT
<213> ORGANISM: Artificial sequence
<220> FEATURE:
<223> OTHER INFORMATION: chemically synthesized

<400> SEQUENCE: 4

Asp Ile Gln Met Thr Gln Ser Ser Ser Phe Leu Ser Val Ser Leu
  1               5                  10                  15

Gly Gly Arg Val Thr Ile Thr Cys Lys Ala Ser Asp Leu Ile His
                 20                  25                  30

Asn Trp Leu Ala Trp Tyr Gln Gln Lys Pro Gly Asn Ala Pro Arg
                 35                  40                  45

Leu Leu Ile Ser Gly Ala Thr Ser Leu Glu Thr Gly Val Pro Ser
                 50                  55                  60

Arg Phe Ser Gly Ser Gly Ser Gly Asn Asp Tyr Thr Leu Ser Ile
                 65                  70                  75

Ala Ser Leu Gln Thr Glu Asp Ala Ala Thr Tyr Tyr Cys Gln Gln
                 80                  85                  90

Tyr Trp Thr Thr Pro Phe Thr Phe Gly Ser Gly Thr Lys Val Glu
                 95                 100                 105
```

```
Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 5
<211> LENGTH: 214
<212> TYPE: PRT
<213> ORGANISM: Artificial sequence
<220> FEATURE:
<223> OTHER INFORMATION: chemically synthesized

<400> SEQUENCE: 5

Asp Ile Gln Met Thr Gln Ser Pro Ser Ser Leu Ser Ala Ser Val
 1               5                  10                  15

Gly Asp Arg Val Thr Ile Thr Gly Arg Ala Ser Gln Asp Val Asn
            20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
            50                  55                  60

Arg Phe Ser Gly Ser Arg Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

His Tyr Thr Thr Pro Pro Thr Phe Gly Gln Gly Thr Lys Val Glu
            95                  100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 6
```

<211> LENGTH: 450
<212> TYPE: PRT
<213> ORGANISM: Artificial sequence
<220> FEATURE:
<223> OTHER INFORMATION: chemically synthesized

<400> SEQUENCE: 6

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val His Gln Ala Pro Gly Lys Gly Leu
                35                  40                  45

Glu Trp Val Ala Arg Ile Tyr Pro Thr Asn Gly Tyr Thr Arg Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ser Arg Trp Gly Gly Asp Gly Phe Tyr
                95                 100                 105

Ala Met Asp Tyr Trp Gly Gln Gly Thr Leu Val Thr Val Ser Ser
               110                 115                 120

Ala Ser Thr Lys Gly Pro Ser Val Phe Pro Leu Ala Pro Ser Ser
               125                 130                 135

Lys Ser Thr Ser Gly Gly Thr Ala Ala Leu Gly Cys Leu Val Lys
               140                 145                 150

Asp Tyr Phe Pro Glu Pro Val Thr Val Ser Trp Asn Ser Gly Ala
               155                 160                 165

Leu Thr Ser Gly Val His Thr Phe Pro Ala Val Leu Gln Ser Ser
               170                 175                 180

Gly Leu Tyr Ser Leu Ser Ser Val Val Thr Val Pro Ser Ser Ser
               185                 190                 195

Leu Gly Thr Gln Thr Tyr Ile Gly Asn Val Asn His Lys Pro Ser
               200                 205                 210

Asn Thr Lys Val Asp Lys Lys Val Glu Pro Lys Ser Cys Asp Lys
               215                 220                 225

Thr His Thr Gly Pro Pro Cys Pro Ala Pro Glu Leu Leu Gly Gly
               230                 235                 240

Pro Ser Val Phe Leu Phe Pro Pro Lys Pro Lys Asp Thr Leu Met
               245                 250                 255

Ile Ser Arg Thr Pro Glu Val Thr Cys Val Val Val Asp Val Ser
               260                 265                 270

His Glu Asp Pro Glu Val Lys Phe Asn Trp Tyr Val Asp Gly Val
               275                 280                 285

Glu Val His Asn Ala Lys Thr Lys Pro Arg Glu Glu Gln Tyr Asn
               290                 295                 300

Ser Thr Tyr Arg Val Val Ser Val Leu Thr Val Leu His Gln Asp
               305                 310                 315

Trp Leu Asn Gly Lys Glu Tyr Lys Cys Lys Val Ser Asn Lys Ala
               320                 325                 330

Leu Pro Ala Pro Ile Glu Lys Thr Ile Ser Lys Ala Lys Gly Gln
               335                 340                 345

Pro Arg Glu Pro Gln Val Tyr Thr Leu Pro Pro Ser Arg Glu Glu
               350                 355                 360
```

```
Met Thr Lys Asn Gln Val Ser Leu Thr Cys Leu Val Lys Gly Phe
                365                 370                 375

Tyr Pro Ser Asp Ile Ala Val Glu Trp Glu Ser Asn Gly Gln Pro
                380                 385                 390

Glu Asn Asn Tyr Lys Thr Thr Pro Pro Val Leu Asp Ser Asp Gly
                395                 400                 405

Ser Phe Phe Leu Tyr Ser Lys Leu Thr Val Asp Lys Ser Arg Trp
                410                 415                 420

Gln Gln Gly Asn Val Phe Ser Cys Ser Val Met His Glu Ala Leu
                425                 430                 435

His Asn His Tyr Thr Gln Lys Ser Leu Ser Leu Ser Pro Gly Lys
                440                 445                 450

<210> SEQ ID NO 7
<211> LENGTH: 446
<212> TYPE: PRT
<213> ORGANISM: Artificial sequence
<220> FEATURE:
<223> OTHER INFORMATION: chemically synthesized

<400> SEQUENCE: 7

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Ser Tyr Ser Gly Tyr Thr Thr Tyr
                 50                  55                  60

Asn Pro Ser Ile Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Thr Ser Gly Leu Asp Tyr
                 95                 100                 105

Trp Gly Gln Gly Thr Leu Val Thr Val Ser Ser Ala Ser Thr Lys
                110                 115                 120

Gly Pro Ser Val Phe Pro Leu Ala Pro Ser Ser Lys Ser Thr Ser
                125                 130                 135

Gly Gly Thr Ala Ala Leu Gly Cys Leu Val Lys Asp Tyr Phe Pro
                140                 145                 150

Glu Pro Val Thr Val Ser Trp Asn Ser Gly Ala Leu Thr Ser Gly
                155                 160                 165

Val His Thr Phe Pro Ala Val Leu Gln Ser Ser Gly Leu Tyr Ser
                170                 175                 180

Leu Ser Ser Val Val Thr Val Pro Ser Ser Ser Leu Gly Thr Gln
                185                 190                 195

Thr Tyr Ile Cys Asn Val Asn His Lys Pro Ser Asn Thr Lys Val
                200                 205                 210

Asp Lys Lys Val Glu Pro Lys Ser Cys Asp Lys Thr His Thr Cys
                215                 220                 225

Pro Pro Cys Pro Ala Pro Glu Leu Leu Gly Gly Pro Ser Val Phe
                230                 235                 240

Leu Phe Pro Pro Lys Pro Lys Asp Thr Leu Met Ile Ser Arg Thr
                245                 250                 255
```

```
Pro Glu Val Thr Cys Val Val Val Asp Val Ser His Glu Asp Pro
            260                 265                 270

Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Ala
            290                 295                 300

Val Val Ser Val Leu Thr Val Leu His Gln Asp Trp Leu Asn Gly
            305                 310                 315

Lys Glu Tyr Lys Cys Lys Val Ser Asn Lys Ala Leu Pro Ala Pro
            320                 325                 330

Ile Glu Lys Thr Ile Ser Lys Ala Lys Gly Gln Pro Arg Glu Pro
            335                 340                 345

Gln Val Tyr Thr Leu Pro Pro Ser Arg Glu Glu Met Thr Lys Asn
            350                 355                 360

Gln Val Ser Leu Thr Cys Leu Val Lys Gly Phe Tyr Pro Ser Asp
            365                 370                 375

Ile Ala Val Glu Trp Glu Ser Asn Gly Gln Pro Glu Asn Asn Tyr
            380                 385                 390

Lys Thr Thr Pro Pro Val Leu Asp Ser Asp Gly Ser Phe Phe Leu
            395                 400                 405

Tyr Ser Lys Leu Thr Val Asp Lys Ser Arg Trp Gln Gln Gly Asn
            410                 415                 420

Val Phe Ser Cys Ser Val Met His Glu Ala Leu His Asn His Tyr
            425                 430                 435

Thr Gln Lys Ser Leu Ser Leu Ser Pro Gly Lys
            440                 445

<210> SEQ ID NO 8
<211> LENGTH: 446
<212> TYPE: PRT
<213> ORGANISM: Artificial sequence
<220> FEATURE:
<223> OTHER INFORMATION: chemically synthesized

<400> SEQUENCE: 8

Asp Val Gln Leu Gln Glu Ser Gly Pro Gly Leu Val Asn Pro Ser
  1               5                  10                  15

Gln Ser Leu Ser Leu Thr Cys Thr Val Thr Gly Tyr Ser Ile Thr
             20                  25                  30

Asn Asp Tyr Ala Trp Asn Trp Ile Arg Gln Phe Pro Gly Asn Lys
             35                  40                  45

Leu Glu Trp Met Gly Tyr Ile Asn Tyr Ser Gly Tyr Thr Thr Tyr
             50                  55                  60

Asn Pro Ser Leu Lys Ser Arg Ile Ser Ile Thr Arg Asp Thr Ser
             65                  70                  75

Lys Asn Gln Phe Phe Leu His Leu Asn Ser Val Thr Thr Glu Asp
             80                  85                  90

Thr Ala Thr Tyr Tyr Cys Ala Arg Trp Asp Gly Gly Leu Thr Tyr
             95                 100                 105

Trp Gly Gln Gly Thr Leu Val Thr Val Ser Ala Ala Ser Thr Lys
            110                 115                 120

Gly Pro Ser Val Phe Pro Leu Ala Pro Ser Ser Lys Ser Thr Ser
            125                 130                 135

Gly Gly Thr Ala Ala Leu Gly Cys Leu Val Lys Asp Tyr Phe Pro
            140                 145                 150
```

```
Glu Pro Val Thr Val Ser Trp Asn Ser Gly Ala Leu Thr Ser Gly
                155                 160                 165

Val His Thr Phe Pro Ala Val Leu Gln Ser Ser Gly Leu Tyr Ser
                170                 175                 180

Leu Ser Ser Val Val Thr Val Pro Ser Ser Ser Leu Gly Thr Gln
                185                 190                 195

Thr Tyr Ile Cys Asn Val Asn His Lys Pro Ser Asn Thr Lys Val
                200                 205                 210

Asp Lys Lys Val Glu Pro Lys Ser Cys Asp Lys Thr His Thr Cys
                215                 220                 225

Pro Pro Cys Pro Ala Pro Glu Leu Leu Gly Gly Pro Ser Val Phe
                230                 235                 240

Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro
                260                 265                 270

Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly
                305                 310                 315

Lys Glu Tyr Lys Cys Lys Val Ser Asn Lys Ala Leu Pro Ala Pro
                320                 325                 330

Ile Glu Lys Thr Ile Ser Lys Ala Lys Gly Gln Pro Arg Glu Pro
                335                 340                 345

Gln Val Tyr Thr Leu Pro Pro Ser Arg Glu Glu Met Thr Lys Asn
                350                 355                 360

Gln Val Ser Leu Thr Cys Leu Val Lys Gly Phe Tyr Pro Ser Asp
                365                 370                 375

Ile Ala Val Glu Trp Glu Ser Asn Gly Gln Pro Glu Asn Asn Tyr
                380                 385                 390

Lys Thr Thr Pro Pro Val Leu Asp Ser Asp Gly Ser Phe Phe Leu
                395                 400                 405

Tyr Ser Lys Leu Thr Val Asp Lys Ser Arg Trp Gln Gln Gly Asn
                410                 415                 420

Val Phe Ser Cys Ser Val Met His Glu Ala Leu His Asn His Tyr
                425                 430                 435

Thr Gln Lys Ser Leu Ser Leu Ser Pro Gly Lys
                440                 445

<210> SEQ ID NO 9
<211> LENGTH: 10
<212> TYPE: PRT
<213> ORGANISM: Artificial sequence
<220> FEATURE:
<223> OTHER INFORMATION: chemically synthesized

<400> SEQUENCE: 9

Glu Val Gln Leu Cys Glu Ser Gly Gly Gly
                5                   10

<210> SEQ ID NO 10
<211> LENGTH: 11
<212> TYPE: PRT
<213> ORGANISM: Artificial sequence
```

```
<220> FEATURE:
<223> OTHER INFORMATION: chemically synthesized

<400> SEQUENCE: 10

Leu Arg Leu Ser Cys Cys Ala Ser Gly Tyr Ser
                  5                  10

<210> SEQ ID NO 11
<211> LENGTH: 11
<212> TYPE: PRT
<213> ORGANISM: Artificial sequence
<220> FEATURE:
<223> OTHER INFORMATION: chemically synthesized

<400> SEQUENCE: 11

Met Asn Ser Leu Arg Cys Glu Asp Thr Ala Val
                  5                  10

<210> SEQ ID NO 12
<211> LENGTH: 11
<212> TYPE: PRT
<213> ORGANISM: Artificial sequence
<220> FEATURE:
<223> OTHER INFORMATION: chemically synthesized

<400> SEQUENCE: 12

Thr Leu Val Thr Val Cys Ser Ala Ser Thr Lys
                  5                  10

<210> SEQ ID NO 13
<211> LENGTH: 11
<212> TYPE: PRT
<213> ORGANISM: Artificial sequence
<220> FEATURE:
<223> OTHER INFORMATION: chemically synthesized

<400> SEQUENCE: 13

Val Thr Val Ser Ser Cys Ser Thr Lys Gly Pro
                  5                  10

<210> SEQ ID NO 14
<211> LENGTH: 11
<212> TYPE: PRT
<213> ORGANISM: Artificial sequence
<220> FEATURE:
<223> OTHER INFORMATION: chemically synthesized

<400> SEQUENCE: 14

Val Ser Ala Ala Ser Cys Lys Gly Pro Ser Val
                  5                  10

<210> SEQ ID NO 15
<211> LENGTH: 11
<212> TYPE: PRT
<213> ORGANISM: Artificial sequence
<220> FEATURE:
<223> OTHER INFORMATION: chemically synthesized

<400> SEQUENCE: 15

Trp Tyr Val Asp Gly Cys Glu Val His Asn Ala
                  5                  10

<210> SEQ ID NO 16
<211> LENGTH: 11
<212> TYPE: PRT
<213> ORGANISM: Artificial sequence
<220> FEATURE:
```

<223> OTHER INFORMATION: chemically synthesized

<400> SEQUENCE: 16

Lys Gly Phe Val Pro Cys Asp Ile Ala Val Glu
                5                   10

<210> SEQ ID NO 17
<211> LENGTH: 11
<212> TYPE: PRT
<213> ORGANISM: Artificial sequence
<220> FEATURE:
<223> OTHER INFORMATION: chemically synthesized

<400> SEQUENCE: 17

Pro Pro Val Leu Asp Cys Gly Asp Ser Phe Phe
                5                   10

<210> SEQ ID NO 18
<211> LENGTH: 10
<212> TYPE: PRT
<213> ORGANISM: Artificial sequence
<220> FEATURE:
<223> OTHER INFORMATION: chemically synthesized

<400> SEQUENCE: 18

Asp Val Gln Leu Cys Glu Ser Gly Pro Gly
                5                   10

<210> SEQ ID NO 19
<211> LENGTH: 11
<212> TYPE: PRT
<213> ORGANISM: Artificial sequence
<220> FEATURE:
<223> OTHER INFORMATION: chemically synthesized

<400> SEQUENCE: 19

Leu Ser Leu Thr Cys Cys Val Thr Gly Tyr Ser
                5                   10

<210> SEQ ID NO 20
<211> LENGTH: 11
<212> TYPE: PRT
<213> ORGANISM: Artificial sequence
<220> FEATURE:
<223> OTHER INFORMATION: chemically synthesized

<400> SEQUENCE: 20

Leu Asn Ser Val Thr Cys Glu Asp Thr Ala Thr
                5                   10

<210> SEQ ID NO 21
<211> LENGTH: 11
<212> TYPE: PRT
<213> ORGANISM: Artificial sequence
<220> FEATURE:
<223> OTHER INFORMATION: chemically synthesized

<400> SEQUENCE: 21

Thr Leu Val Thr Val Cys Ser Ala Ser Thr Lys
                5                   10

<210> SEQ ID NO 22
<211> LENGTH: 11
<212> TYPE: PRT
<213> ORGANISM: Artificial sequence
<220> FEATURE:
<223> OTHER INFORMATION: chemically synthesized

```
<400> SEQUENCE: 22

Val Thr Val Ser Ser Cys Ser Thr Lys Gly Pro
                5                   10

<210> SEQ ID NO 23
<211> LENGTH: 11
<212> TYPE: PRT
<213> ORGANISM: Artificial sequence
<220> FEATURE:
<223> OTHER INFORMATION: chemically synthesized

<400> SEQUENCE: 23

Val Ser Ala Ala Ser Cys Lys Gly Pro Ser Val
                5                   10

<210> SEQ ID NO 24
<211> LENGTH: 11
<212> TYPE: PRT
<213> ORGANISM: Artificial sequence
<220> FEATURE:
<223> OTHER INFORMATION: chemically synthesized

<400> SEQUENCE: 24

Trp Tyr Val Asp Gly Cys Glu Val His Asn Ala
                5                   10

<210> SEQ ID NO 25
<211> LENGTH: 11
<212> TYPE: PRT
<213> ORGANISM: Artificial sequence
<220> FEATURE:
<223> OTHER INFORMATION: chemically synthesized

<400> SEQUENCE: 25

Lys Gly Phe Val Pro Cys Asp Ile Ala Val Glu
                5                   10

<210> SEQ ID NO 26
<211> LENGTH: 11
<212> TYPE: PRT
<213> ORGANISM: Artificial sequence
<220> FEATURE:
<223> OTHER INFORMATION: chemically synthesized

<400> SEQUENCE: 26

Pro Pro Val Leu Asp Cys Asp Gly Ser Phe Phe
                5                   10

<210> SEQ ID NO 27
<211> LENGTH: 11
<212> TYPE: PRT
<213> ORGANISM: Artificial sequence
<220> FEATURE:
<223> OTHER INFORMATION: chemically synthesized

<400> SEQUENCE: 27

Ser Leu Ser Ala Ser Cys Gly Asp Arg Val Thr
                5                   10

<210> SEQ ID NO 28
<211> LENGTH: 11
<212> TYPE: PRT
<213> ORGANISM: Artificial sequence
<220> FEATURE:
<223> OTHER INFORMATION: chemically synthesized
```

```
<400> SEQUENCE: 28

Glu Ile Lys Arg Thr Cys Ala Ala Pro Ser Val
                5                   10

<210> SEQ ID NO 29
<211> LENGTH: 11
<212> TYPE: PRT
<213> ORGANISM: Artificial sequence
<220> FEATURE:
<223> OTHER INFORMATION: chemically synthesized

<400> SEQUENCE: 29

Thr Val Ala Ala Pro Cys Val Phe Ile Phe Pro
                5                   10

<210> SEQ ID NO 30
<211> LENGTH: 11
<212> TYPE: PRT
<213> ORGANISM: Artificial sequence
<220> FEATURE:
<223> OTHER INFORMATION: chemically synthesized

<400> SEQUENCE: 30

Phe Ile Phe Pro Pro Cys Asp Glu Gln Leu Lys
                5                   10

<210> SEQ ID NO 31
<211> LENGTH: 11
<212> TYPE: PRT
<213> ORGANISM: Artificial sequence
<220> FEATURE:
<223> OTHER INFORMATION: chemically synthesized

<400> SEQUENCE: 31

Asp Glu Gln Leu Lys Cys Gly Thr Ala Ser Val
                5                   10

<210> SEQ ID NO 32
<211> LENGTH: 11
<212> TYPE: PRT
<213> ORGANISM: Artificial sequence
<220> FEATURE:
<223> OTHER INFORMATION: chemically synthesized

<400> SEQUENCE: 32

Val Thr Glu Gln Asp Cys Lys Asp Ser Thr Tyr
                5                   10

<210> SEQ ID NO 33
<211> LENGTH: 11
<212> TYPE: PRT
<213> ORGANISM: Artificial sequence
<220> FEATURE:
<223> OTHER INFORMATION: chemically synthesized

<400> SEQUENCE: 33

Gly Leu Ser Ser Pro Cys Thr Lys Ser Phe Asn
                5                   10
```

```
<210> SEQ ID NO 34
<211> LENGTH: 11
<212> TYPE: PRT
<213> ORGANISM: Artificial sequence
<220> FEATURE:
<223> OTHER INFORMATION: chemically synthesized

<400> SEQUENCE: 34

Phe Leu Ser Val Ser Cys Gly Gly Arg Val Thr
                 5                   10

<210> SEQ ID NO 35
<211> LENGTH: 11
<212> TYPE: PRT
<213> ORGANISM: Artificial sequence
<220> FEATURE:
<223> OTHER INFORMATION: chemically synthesized

<400> SEQUENCE: 35

Glu Ile Lys Arg Thr Cys Ala Ala Pro Ser Val
                 5                   10

<210> SEQ ID NO 36
<211> LENGTH: 11
<212> TYPE: PRT
<213> ORGANISM: Artificial sequence
<220> FEATURE:
<223> OTHER INFORMATION: chemically synthesized

<400> SEQUENCE: 36

Thr Val Ala Ala Pro Cys Val Phe Ile Phe Pro
                 5                   10

<210> SEQ ID NO 37
<211> LENGTH: 11
<212> TYPE: PRT
<213> ORGANISM: Artificial sequence
<220> FEATURE:
<223> OTHER INFORMATION: chemically synthesized

<400> SEQUENCE: 37

Phe Ile Phe Pro Pro Cys Asp Glu Gln Leu Lys
                 5                   10

<210> SEQ ID NO 38
<211> LENGTH: 11
<212> TYPE: PRT
<213> ORGANISM: Artificial sequence
<220> FEATURE:
<223> OTHER INFORMATION: chemically synthesized

<400> SEQUENCE: 38

Asp Glu Gln Leu Lys Cys Gly Thr Ala Ser Val
                 5                   10

<210> SEQ ID NO 39
<211> LENGTH: 11
<212> TYPE: PRT
<213> ORGANISM: Artificial sequence
<220> FEATURE:
<223> OTHER INFORMATION: chemically synthesized

<400> SEQUENCE: 39

Val Thr Glu Gln Asp Cys Lys Asp Ser Thr Tyr
                 5                   10
```

```
<210> SEQ ID NO 40
<211> LENGTH: 11
<212> TYPE: PRT
<213> ORGANISM: Artificial sequence
<220> FEATURE:
<223> OTHER INFORMATION: chemically synthesized

<400> SEQUENCE: 40

Gly Leu Ser Ser Pro Cys Thr Lys Ser Phe Asn
 1               5                  10

<210> SEQ ID NO 41
<211> LENGTH: 19
<212> TYPE: PRT
<213> ORGANISM: Artificial sequence
<220> FEATURE:
<223> OTHER INFORMATION: chemically synthesized

<400> SEQUENCE: 41

Met Gly Trp Ser Cys Ile Ile Leu Phe Leu Val Ala Thr Ala Thr
 1               5                  10                  15

Gly Val His Ser

<210> SEQ ID NO 42
<211> LENGTH: 19
<212> TYPE: PRT
<213> ORGANISM: Artificial sequence
<220> FEATURE:
<223> OTHER INFORMATION: chemically synthesized

<400> SEQUENCE: 42

Met Gly Trp Ser Cys Ile Ile Leu Phe Leu Val Ala Thr Ala Thr
 1               5                  10                  15

Gly Ala Tyr Ala
```

CYSTEINE ENGINEERED ANTI-MUC16 ANTIBODIES AND ANTIBODY DRUG CONJUGATES

CROSS REFERENCE TO RELATED APPLICATIONS

This non-provisional application filed under 37 CFR §1.53 (b), claims the benefit under 35 USC §119(e) of U.S. Provisional Application Ser. No. 60/916,657 filed on 8 May 2007, which is incorporated by reference in entirety.

FIELD OF THE INVENTION

The invention relates generally to antibodies engineered with reactive cysteine residues and more specifically to antibodies with therapeutic or diagnostic applications. The cysteine engineered antibodies may be conjugated with chemotherapeutic drugs, toxins, affinity ligands such as biotin, and detection labels such as fluorophores. The invention also relates to methods of using antibodies and antibody-drug conjugate compounds for in vitro, in situ, and in vivo diagnosis or treatment of mammalian cells, or associated pathological conditions.

BACKGROUND OF THE INVENTION

Antibody therapy has been established for the targeted treatment of patients with cancer, immunological and angiogenic disorders. Transmembrane or otherwise tumor-associated polypeptides specifically expressed on the surface of cancer cells as compared to normal, non-cancerous cell(s) have been identified as cellular targets for cancer diagnosis and therapy with antibodies. Identification of such tumor-associated cell surface antigen polypeptides, i.e. tumor associated antigens (TAA), allows specific targeting of cancer cells for destruction via antibody-based therapies.

The use of antibody-drug conjugates (ADC), i.e. immunoconjugates, for the local delivery of cytotoxic or cytostatic agents, i.e. drugs to kill or inhibit tumor cells in the treatment of cancer (Lambert, J. (2005) Curr. Opinion in Pharmacology 5:543-549; Wu et al (2005) Nature Biotechnology 23(9):1137-1146; Payne, G. (2003) Cancer Cell 3:207-212; (Polakis, P. Arming antibodies for cancer therapy. Curr Opin Pharmacol 5, 382-387, 2005). Syrigos and Epenetos (1999) Anticancer Research 19:605-614; Niculescu-Duvaz and Springer (1997) Adv. Drug Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al (ed.s), pp. 475-506). Efforts to improve the therapeutic index, i.e. maximal efficacy and minimal toxicity of ADC have focused on the selectivity of polyclonal (Rowland et al (1986) Cancer Immunol. Immunother., 21:183-87) and monoclonal antibodies (mAbs) as well as drug-linking and drug-releasing properties (Lambert, J. (2005) Curr. Opinion in Pharmacology 5:543-549). Drug moieties used in antibody drug conjugates include bacterial protein toxins such as diphtheria toxin, plant protein toxins such as ricin, small molecules such as auristatins, geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al (1996) Proc. Natl. Acad. Sci. USA 93:8618-8623), calicheamicin (Lode et al (1998) Cancer Res. 58:2928; Hinman et al (1993) Cancer Res. 53:3336-3342), daunomycin, doxorubicin, methotrexate, and vindesine (Rowland et al (1986) supra). The drug moieties may affect cytotoxic and cytostatic mechanisms including tubulin binding, DNA binding, or topoisomerase inhibition. Some cytotoxic drugs tend to be inactive or less active when conjugated to large antibodies or protein receptor ligands.

The auristatin peptides, auristatin E (AE) and monomethylauristatin (MMAE), synthetic analogs of dolastatin (WO 02/088172), have been conjugated as drug moieties to various antibodies (Klussman, et al (2004), Bioconjugate Chemistry 15(4):765-773; Doronina et al (2003) Nature Biotechnology 21(7):778-784; Francisco et al (2003) Blood 102(4):1458-1465; US 2004/0018194; WO 04/032828; Mao et al (2004) Cancer Research 64(3):781-788); Bhaskar et al (2003) Cancer Res. 63:6387-6394); WO 03/043583; U.S. Pat. No. 5,767,237; U.S. Pat. No. 6,124,431; US 2005/0238649).

Conventional means of attaching, i.e. linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody or through cysteine sulfhydryls (thiols) activated by reducing interchain disulfide bonds, generating a heterogeneous antibody-drug conjugate mixture, containing species with different molar ratios of drug to antibody, linked at different sites, each with a distinct in vivo profile of pharmacokinetics, efficacy, and safety (Hamblett et al (2004) Clin. Cancer Res. 10:7063-7070; Wang et al (2005) Protein Sci. 14:2436-2446). Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods may be inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multi-step conjugation process may be nonreproducible due to difficulties in controlling the reaction conditions and characterizing reactants and intermediates.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Extracellular proteins generally do not have free thiols (Garman, 1997, Non-Radioactive Labelling: A Practical Approach, Academic Press, London, at page 55). Antibody cysteine thiol groups are generally more reactive, i.e. more nucleophilic, towards electrophilic conjugation reagents than antibody amine or hydroxyl groups. Solvent-accessible inter-chain disulfide bond cysteines with serine to allow directed conjugation to the remaining cysteines (McDonagh et al (2006) Protein Eng. Des. Sel. 19:299-307). However, elimination of these disulfide bonds could disrupt quaternary structure of the antibody, thereby perturbing the behavior of the antibody in vivo, including changes in antibody effector functions (Michaelsen et al (1994) Proc Natl Acad Sci USA 91:9243-9247; Romans et al (1977) Proc Natl Acad Sci USA 74:2531-2535; Seegan et al (1979) Proc Natl Acad Sci USA 76:907-911). Cysteine residues have been introduced into proteins by genetic engineering techniques to form covalent attachments to ligands or to form new intramolecular disulfide bonds (Better et al (1994) J. Biol. Chem. 13:9644-9650; Bernhard et al (1994) Bioconjugate Chem. 5:126-132; Greenwood et al (1994) Therapeutic Immunology 1:247-255; Tu et al (1999) Proc. Natl. Acad. Sci USA 96:4862-4867; Kanno et al (2000) J. of Biotechnology, 76:207-214; Chmura et al (2001) Proc. Nat. Acad. Sci. USA 98(15):8480-8484; U.S. Pat. No. 6,248,564). However, engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of *E. coli*, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys thiol groups are unavailable for active site participation and interactions. Furthermore, the protein may be rendered inactive or non-specific, by misfolding or loss of tertiary structure (Zhang et al (2002) Anal. Biochem. 311:1-9).

Cysteine-engineered antibodies have been designed as FAB antibody fragments (thioFab) and expressed as full-length, IgG monoclonal (thioMab) antibodies (US 2007/0092940, the contents of which are incorporated by reference). ThioFab and ThioMab antibodies have been conjugated through linkers at the newly introduced cysteine thiols with thiol-reactive linker reagents and drug-linker reagents to prepare antibody drug conjugates (Thio ADC).

MUC16 is a tumor associated antigen polypeptide, expressed by the human ocular surface epithelia (Argueso et al (2003) Investigative Ophthalmology & Visual Science 44(6):2487-95) in the mucosa of the bronchus, fallopian tube, and uterus (Kabawat et al. (1983) International Journal of Gynecological Pathology 2:275-85). One proposed function of MUC16 is to provide a protective, lubricating barrier against particles and infectious agents at mucosal surfaces. Highly polymorphic, MUC16 is composed of three domains, a Ser-/Thr-rich N-terminal domain, a repeat domain of between eleven and more than 60 partially conserved tandem repeats of on average 156 amino acids each, and a C-terminal non-repeating domain containing a transmembrane sequence and a short cytoplasmic tail. MUC16 is heavily O-glycosylated and N-glycosylated (O'Brien et al (2002) Tumour Biol. 23:154-169; O'Brien et al (2001) Tumour Biol. 22:348-366 (2001); Fendrick et al (1997) Tumour Biol. 18:278-289; Wong et al (2003) J. Biol. Chem. 278:28619-28634; McLemore et al (2005) biol. Res. Nurs. 6:262-267). mRNA encoding the MUC16 polypeptide expressed from the MUC16 gene is significantly, reproducibly and detectably overexpressed in certain types of human cancerous ovarian, breast and pancreatic tumors as compared to the corresponding normal human ovarian, breast and pancreatic tissues, respectively (WO 2007/001851). A variety of independent and different types of cancerous human ovarian tissue samples quantitatively analyzed for MUC16 expression show the level of expression of MUC16 in the cancerous samples is variable, with a significant number of the cancerous samples showing an at least 6-fold (to as high as an about 580-fold) increase in MUC16 expression when compared to the mean level of MUC16 expression for the group of normal ovarian tissue samples analyzed. In particular, detectable and reproducible MUC16 overexpression was observed for ovarian cancer types; endometrioid adenocarcinoma, serous cystadenocarcinoma, including papillary and clear cell adenocarcinoma, as compared to normal ovarian tissue. Due to its overexpression in certain human tumors, the MUC16 polypeptide and the nucleic acid encoding that polypeptide are targets for quantitative and qualitative comparisons among various mammalian tissue samples. The unique expression profiles of MUC16 polypeptide, and the nucleic acid encoding that polypeptide, can be exploited for the diagnosis and therapeutic treatment of certain types of cancerous tumors in mammals.

CA125 (Carcinoma antigen 125 (O772P, CA-O772P, CA-125) is an extracellular shed protein encoded by the MUC16 gene (Yin et al (2002) Intl. J. of Cancer 98(5):737-740), and a serum marker used routinely to monitor patients with ovarian cancer. CA125 is a mullerian duct differentiation antigen that is overexpressed in epithelial ovarian cancer cells and secreted into the blood, although its expression is not entirely confined to ovarian cancer (Bast et al (1981) J. Clin. Invest. 68:1331-1337). Serum CA125 levels are elevated in about 80% of patients with epithelial ovarian cancer (EOC) but in less than 1% of healthy women (Bast et al. (1983) N. Engl. J. Med. 309:883-887). CA125 is a giant mucin-like glycoprotein present on the cell surface of tumor cells associated with beta-galactoside-binding, cell-surface lectins, which are components of the extracellular matrix implicated in the regulation of cell adhesion, apoptosis, cell proliferation and tumor progression (Seelenmeyer et al (2003) Journal of Cell Science 116(7):1305-1318). High serum concentration of CA125 is typical of serous ovarian adenocarcinoma, whereas it is not elevated in mucinous ovarian cancer. CA125 is not recommended for ovarian cancer screening because normal level does not exclude tumor. However, CA125 detection is a standard tool in monitoring clinical course and disease status in patients who have histologically confirmed malignancies. Numerous studies have confirmed the usefulness of CA125 levels in monitoring the progress of patients with EOC (Bast et al (1998) Int. J. Biol. Markers 13:179-187; Verheijen et al (1999) Sem. Cancer Biol. 9:117-124; Menon et al (2000) Curr. Opin. Obstet. Gynecol. 12:39-42; Meyer et al (2000) Br. J. Cancer 82:1535-1538), and as a cancer serum marker. A rise in CA125 levels typically precedes clinical detection by about 3 months. During chemotherapy, changes in serum CA125 levels correlate with the course of the disease. CA125 is used as a surrogate marker for clinical response in trials of new drugs. On the other hand, CA125 is not useful in the initial diagnosis of EOC because of its elevation in a number of benign conditions (Bast et al (1998) Int. J. Biol. Markers 13:179-187; Meden et al (1998) Int. J. Biol. Markers 13:231-237). The CA125-specific antibody MAb-B43.13 (oregovomab, OvaRex MAb-B43.13) was in clinical trials for patients with ovarian carcinoma as an immunotherapeutic agent Mobus et al (2003) American Journal of Obstetrics and Gynecology 189(1):28-36; Ehlen et al (2005) International journal of gynecological cancer 15(6):1023-34.

Certain anti-MUC16 antibodies, including 3A5 and 11D10, have been disclosed in WO 2007/001851; U.S. Ser. No. 11/452,990, filed 14 Jun. 2006, Dennis et al, "Compositions and Methods for the Diagnosis and Treatment of Tumor", the contents of which are incorporated by reference. The 3A5 monoclonal antibody binds multiple sites of the MUC16 polypeptide with 433 pM affinity by OVCAR-3

Scatchard analysis. The 3A5 and 11D10 anti-MUC16 antibodies have been conjugated to auristatin drug moieties MMAE and MMAF. The conjugates inhibit in vitro tumor cell proliferation (WO 2007/001851). An 11D10 anti-MUC16 antibody was conjugated to the maytansinoid DM1 drug moiety (US 2005/0276812). Certain anti-MUC16 antibody variants have been cysteine engineered by the introduction of a cysteine amino acid unit and conjugated to DM1 (US 2007/0092940, the contents of which are incorporated by reference).

SUMMARY

In one aspect, the invention includes a cysteine engineered anti-MUC16 antibody comprising one or more free cysteine amino acids and a sequence selected from SEQ ID NOS:9-40. The cysteine engineered anti-MUC16 antibody binds to a MUC16 polypeptide. Tumor-associated antigens (TAA) such as O772P (CA125, MUC16) polypeptides can be prepared for use in generating cysteine engineered antibodies using methods and information which are well known in the art, and for example in WO 2007/001851. The cysteine engineered anti-MUC16 antibody may be prepared by a process comprising replacing one or more amino acid residues of a parent anti-MUC16 antibody by cysteine.

The one or more free cysteine amino acid residues of the cysteine engineered anti-MUC16 antibody are located in a light chain or a heavy chain.

In one aspect, the invention includes a method of determining the presence of a MUC16 protein in a sample suspected of containing said protein, said method comprising exposing said sample to a cysteine engineered anti-MUC16 antibody and determining binding of said antibody to said MUC16 protein in said sample, wherein binding of the antibody to said protein is indicative of the presence of said protein in said sample.

Cysteine engineered anti-MUC16 antibodies may be used as naked antibodies (unconjugated to a drug or label moiety) or as antibody-drug conjugates (ADC). The cysteine engineered anti-MUC16 antibody may be covalently attached to an auristatin drug moiety whereby an antibody drug conjugate is formed. The antibody-drug conjugate may comprise a cysteine engineered anti-MUC16 antibody (Ab), and an auristatin drug moiety (D) wherein the cysteine engineered anti-MUC16 antibody is attached through one or more free cysteine amino acids by a linker moiety (L) to D; the compound having Formula I:

Ab-(L-D)$_p$       I where p is 1, 2, 3, or 4. Auristatin drug moieties include MMAE and MMAF.

Another aspect of the invention is a mixture of antibody-drug conjugate compounds comprising a cysteine engineered anti-MUC16 antibody (Ab) which binds to a MUC16 polypeptide and comprising one or more free cysteine amino acids, a sequence selected from SEQ ID NOS:9-40, and an auristatin drug moiety (D) wherein the cysteine engineered anti-MUC16 antibody is attached through one or more free cysteine amino acids by a linker moiety (L) to D; the compound having Formula I:

Ab-(L-D)$_p$       I where p is 1, 2, 3, or 4, and the average drug loading is from 1 to 2.

Auristatin drug moieties include MMAE and MMAF.

An aspect of the invention is an assay for detecting cancer cells comprising: (a) exposing cells to a cysteine engineered anti-MUC16 antibody-drug conjugate; and (b) determining the extent of binding of the cysteine engineered anti-MUC16 antibody-drug conjugate compound to the cells.

An aspect of the invention is a pharmaceutical formulation comprising the cysteine engineered anti-MUC16 antibody drug conjugate, and a pharmaceutically acceptable diluent, carrier or excipient.

An aspect of the invention is a method of inhibiting cellular proliferation comprising treating mammalian tumor cells in a cell culture medium with a cysteine engineered anti-MUC16 antibody-drug conjugate compound, whereby proliferation of the tumor cells is inhibited.

An aspect of the invention is a method of treating cancer comprising administering to a patient the pharmaceutical formulation. The patient may be administered a chemotherapeutic agent in combination with the cysteine engineered anti-MUC16 antibody-drug conjugate compound.

An aspect of the invention is an article of manufacture comprising the pharmaceutical formulation, a container; and a package insert or label indicating that the compound can be used to treat cancer characterized by the overexpression of a MUC16 polypeptide.

An aspect of the invention is a method for making a Formula I antibody drug conjugate compound comprising the steps of: (a) reacting an engineered cysteine group of the cysteine engineered antibody with a linker reagent to form antibody-linker intermediate Ab-L; and (b) reacting Ab-L with an activated drug moiety D; whereby the antibody-drug conjugate is formed; or comprising the steps of: (c) reacting a nucleophilic group of a drug moiety with a linker reagent to form drug-linker intermediate D-L; and (d) reacting D-L with an engineered cysteine group of the cysteine engineered antibody; whereby the antibody-drug conjugate is formed.

BRIEF DESCRIPTION OF THE DRAWINGS

FIG. 1 shows the Heavy Chain sequence: SEQ ID NO:1, and Light Chain sequence: SEQ ID NO:2 of humanized cysteine engineered anti-MUC16 antibody, A117C thio hu 3A5.

FIG. 2 shows the Heavy Chain sequence: SEQ ID NO:3, and Light Chain sequence: SEQ ID NO:4 of chimeric cysteine engineered anti-MUC16 antibody, A117C thio ch 3A5.

FIG. 3 shows alignment of humanized trastuzumab light chain (HuTMAb-LC, SEQ ID NO:5), humanized std 3A5 antiMUC16 light chain (Hu3A5-LC, SEQ ID NO:2), and chimeric std 3A5 antiMUC16 light chain (Ch3A5-LC, SEQ ID NO:4) sequences. The numbering follows the sequential numbering convention.

FIG. 4 shows alignment of humanized trastuzumab heavy chain (HuTMAb-HC, SEQ ID NO:6), humanized std 3A5 antiMUC16 heavy chain (Hu3A5-HC, SEQ ID NO:7), and chimeric std 3A5 antiMUC16 heavy chain (Ch3A5-HC, SEQ ID NO:8) sequences. The numbering follows the sequential numbering convention.

FIG. 8c shows peptide mapping—identification of peptide(s) containing cytotoxic drug in the TDC-Fab. Peptide maps of unconjugated (top panel a) and conjugated (middle panel b) Thio-3A5 and TDC generated from tryptic digests of maleimidylated purified Fabs. Peptides labeled with MC-vc-PAB-MMAE have increased hydrophobicity and are expected to elute later in the chromatogram. Four drug-conjugated peptides (labeled with *) eluted at the end of the gradient. They can also be identified as cytotoxic drug containing peptides by a characteristic in-source fragmentation ion (m/z 718.5) that is observed in all MC-vc-PAB-MMAE containing mass spectra. Bottom panel (c) shows an overlay of the extracted ion chromatogram from the unconjugated and the conjugated digests. The strongest peaks coincide with the late eluting peaks of the conjugate digest. All four peaks were identified as complete or partial tryptic cleavage fragments located around the mutated cysteine in position 114 of the Fab-HC. The m/z ions in the main peak at 29.05 min deconvoluted to give a mass of 3962 daltons, which is the expected mass for peptide HC99-120+1 drug. The drug-containing peptide masses did not map to any other region of the protein. The peak labeled with an arrow in top panel (a) is the maleimide labeled peptide HC99-120.

FIG. 9 summarizes the major species detected by tandem liquid chromatography and mass spectrometric (LC-MS) analyses of the standard humanized 3A5-VC-MMAE conjugate (std hu 3A5-VC-MMAE) and two preparations of the corresponding thio conjugates (thio hu 3A5-VC-MMAE). Proteins were analyzed under reducing conditions ("reduction (DTT)") to disrupt interchain disulfide bonds and under native conditions ("intact").

std ch 3A5-MC-vc-PAB-MMAE, 3.0 mg/kg; E) std ch 3A5-MC-vc-PAB-MMAE, 6.0 mg/kg; F) thio ch 3A5-MC-vc-PAB-MMAE, 1.5 mg/kg; G) thio ch 3A5-MC-vc-PAB-MMAE, 3.0 mg/kg; H) thio ch 3A5-MC-vc-PAB-MMAE, 6.0 mg/kg.

Figure 17:
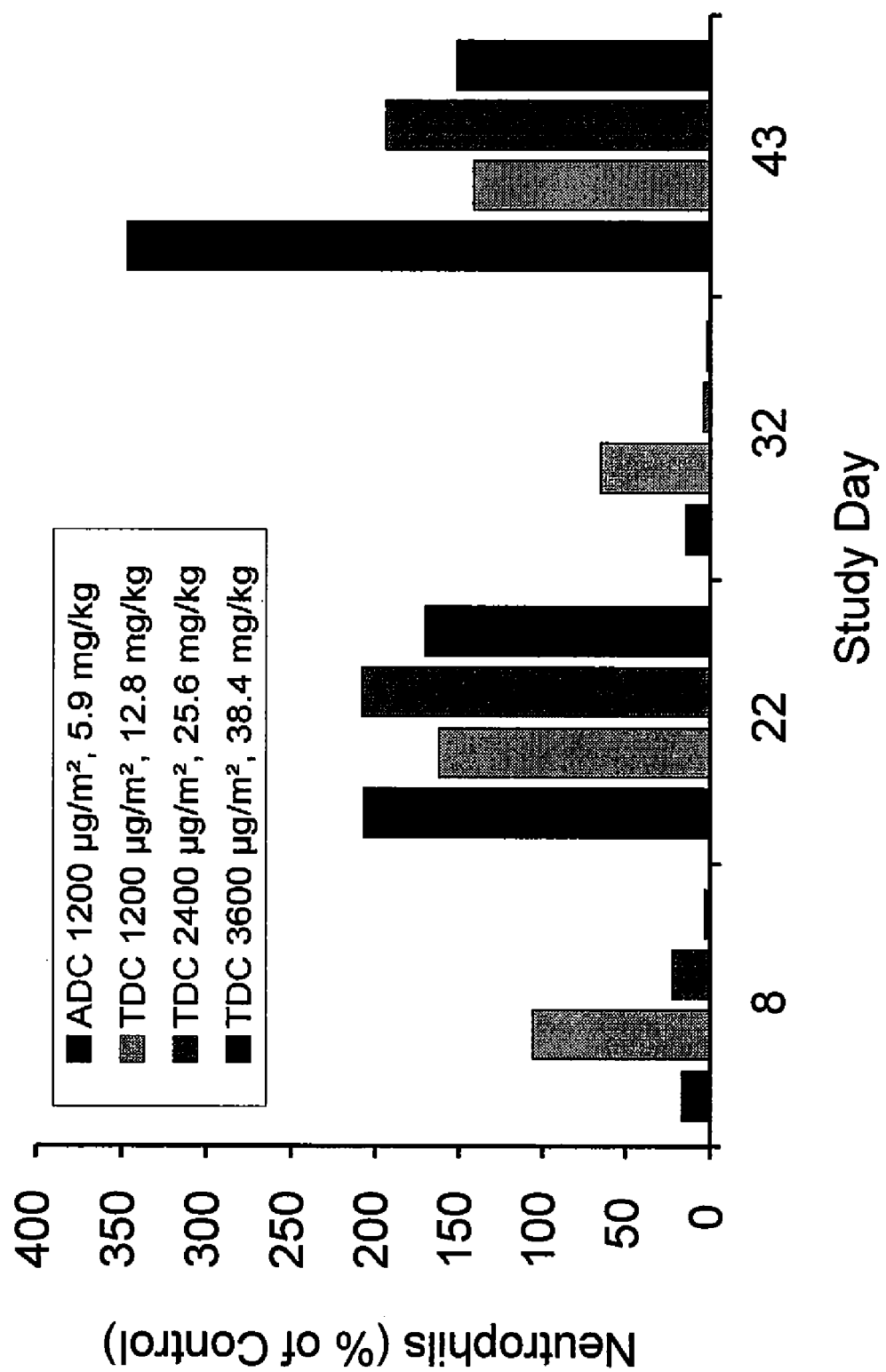

FIG. 17 shows data from safety studies in cynomolgus monkeys dosed at days 1 and 22 with standard anti-MUC16-MC-vc-PAB-MMAE ADC at a drug exposure of 1200 µg/m$^2$ drug (5.9 mg/kg antibody); and thio anti-MUC16-MC-vc-PAB-MMAE ADC (TDC) at drug exposures of 1200, 2400, and 3600 µg/m$^2$. Neutrophil levels were measured at 8, 22 (before second dose), 32, and 43 days after dosing. Neutrophil levels were normalized to the corresponding levels in vehicle-treated animals at the given time point.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

DEFINITIONS

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein that is capable of recognizing and binding to a specific antigen (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species such as human, murine, or rabbit. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; minibodies (U.S. Pat. No. 5,641,870, Example 2; Zapata et al (1995) Protein Eng. 8(10): 1057-1062); Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see for example: U.S. Pat. No. 4,816,567; U.S. Pat. No. 5,807,715). The monoclonal antibodies may also be isolated from phage antibody libraries using the techniques described in Clackson et al (1991) Nature, 352:624-628; Marks et al (1991) J. Mol. Biol., 222:581-597.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

"Native antibodies" are usually heterotetrameric glycoproteins of about 150,000 daltons, composed of two identical light (L) chains and two identical heavy (H) chains. Each light chain is linked to a heavy chain by one covalent disulfide bond, in addition to several hydrophobic interactions held between variable as well as constant domains of light and heavy chain Fab, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all, or substantially all, of the FRs are those of a human immunoglobulin sequence. The humanized antibody optionally also will comprise at least a portion of an immmunoglobulin constant region (Fc), typically that of a human immunoglobulin. The Fc fragment comprises the carboxy-terminal portions of both H chains held together by disulfides and hydrophobic interaction between several amino acid residues. The effector functions of antibodies are determined by sequences in the Fc region, which region is also the part recognized by Fc receptors (FcR) found on certain types of cells (Jones et al (1986) Nature 321:522-525; Riechmann et al (1988) Nature 332:323-329; Presta, (1992) Curr. Op. Struct. Biol. 2:593-596; Verhoeyen et al (1988) Science, 239:1534-1536; Sims et al (1993) J. Immunol. 151: 2296; Chothia et al (1987) J. Mol. Biol., 196:901). Other methods use a particular framework region derived from the consensus sequence of all human antibodies of a particular subgroup of light or heavy chains (Carter et al (1992) Proc. Natl. Acad. Sci. USA, 89:4285; Presta et al (1993) J. Immunol. 151:2623).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Transgenic animals (e.g., mice) are available that are capable, upon immunization, of producing a full repertoire of human antibodies in the absence of endogenous immunoglobulin production (Jakobovits et al (1993) Proc. Natl. Acad. Sci. USA, 90:2551; Jakobovits et al (1993) Nature, 362:255-258; Bruggemann et al (1993) Year in Immuno. 7:33; U.S. Pat. No. 5,545,806; U.S. Pat. No. 5,569,825; U.S. Pat. No. 5,591,669; U.S. Pat. No. 5,545,807; and WO 97/17852.

An "intact antibody" herein is one comprising VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native sequence polypeptide or with at least one ligand binding domain of a native receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991, and which code is found in WO 2007/001851.

The terms "Fc receptor" or "FcR" mean a receptor that binds to the Fc constant region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review M. in Daëron, (1997) "Annu. Rev.

Immunol." 15:203-234). FcRs are reviewed in Ravetch and Kinet, (1991) "Annu. Rev. Immunol"., 9:457-92; Capel et al (1994) Immunomethods 4:25-34; and de Haas et al (1995) J. Lab. Clin. Med. 126:330-41. Other FcRs, including those to be identified in the future, are encompassed by the term "FcR" herein. The term also includes the neonatal receptor, FcRn, which is responsible for the transfer of maternal IgGs to the fetus (Guyer et al (1976) J. Immunol., 117:587 and Kim et al (1994) J. Immunol. 24:249).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)), whereas Chothia refers to the location of the structural loops (Chothia and Lesk (1987) J. Mol. Biol. 196:901-917). The "contact" hypervariable regions are based on an analysis of the available complex crystal structures. The residues from each of these hypervariable regions are noted below. Unless otherwise denoted, Kabat numbering according to the Kabat Database of aligned sequences of proteins will be employed (Wu and Kabat (1970) J. Exp. Med. 132:211-250; Johnson and Wu (2000) Nuc. Acids Res. 28(1):214-218). Hypervariable region locations are generally as follows: amino acids 24-34 (HVR-L1), amino acids 49-56 (HVR-L2), amino acids 89-97 (HVR-L3), amino acids 26-35A (HVR-H1), amino acids 49-65 (HVR-H2), and amino acids 93-102 (HVR-H3). Hypervariable regions may also comprise "extended hypervariable regions" as follows: amino acids 24-36 (L1), and amino acids 46-56 (L2) in the VL. The variable domain residues are numbered according to Kabat et al., supra for each of these definitions. An "altered hypervariable region" for the purposes herein is a hypervariable region comprising one or more (e.g. one to about 16) amino acid substitution(s) therein. An "unmodified hypervariable region" for the purposes herein is a hypervariable region having the same amino acid sequence as a non-human antibody from which it was derived, i.e. one which lacks one or more amino acid substitutions therein.

The terms "variable domain residue numbering as in Kabat", "amino acid position numbering as in Kabat", and variations thereof, refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

An "antigen" is a predetermined polypeptide, carbohydrate, nucleic acid, lipid, hapten or other naturally occurring or synthetic compound to which an antibody can selectively bind.

"Framework" or "FR" residues are those variable domain residues other than the hypervariable region residues as herein defined. A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al, Sequences of Proteins of Immunological Interest, 5th Ed. Public Health Service, National Institutes of Health, Bethesda, Md. (1991). In one embodiment, for the VL, the subgroup is subgroup kappa I as in Kabat et al. In one embodiment, for the VH, the subgroup is subgroup III as in Kabat et al. A "VH subgroup III consensus framework" comprises the consensus sequence obtained from the amino acid sequences in variable heavy subgroup III of Kabat et al. A "VL subgroup I consensus framework" comprises the consensus sequence obtained from the amino acid sequences in variable light kappa subgroup I of Kabat et al.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the VH and VL domains which enables the scFv to form the desired structure for antigen binding (Plückthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites (EP 404,097; WO 93/11161; Hollinger et al (1993) Proc. Natl. Acad. Sci. USA 90:6444-6448).

A "free cysteine amino acid" refers to a cysteine amino acid residue which has been engineered into a parent antibody, has a thiol functional group (—SH), and is not paired as, or otherwise part of, an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 80% yield with a thiol-reactive reagent has a thiol reactivity value of 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests. Thiol-reactive reagents which allow capture of the cysteine engineered antibody and comparison and quantitation of the cysteine reactivity include biotin-PEO-maleimide ((+)-biotinyl-3-maleimidopropionamidyl-3,6-dioxaoctainediamine, Oda et al (2001) Nature Biotechnology 19:379-382, Pierce Biotechnology, Inc.) Biotin-BMCC, PEO-Iodoacetyl Biotin, Iodoacetyl-LC-Biotin, and Biotin-HPDP (Pierce Biotechnology, Inc.), and Nα-(3-maleimidylpropionyl)biocytin (MPB, Molecular Probes, Eugene, Oreg.). Other commercial sources for biotinylation, bifunctional and multifunctional linker reagents include Molecular Probes, Eugene, Oreg., and Sigma, St. Louis, Mo.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" a molecular target or an antigen of interest, e.g., MUC16 or CA125 antigens, is one capable of binding that antigen with sufficient affinity such that the antibody is useful in targeting a cell expressing the antigen. Where the antibody is one which binds a MUC16 polypeptide, it will usually preferentially bind MUC16, and may be one which does not significantly cross-react with other proteins. In such embodiments, the extent of binding of the antibody to these non-MUC16 proteins (e.g., cell surface binding to endogenous receptor) will be less than 10% of the binding to MUC16 as determined by fluorescence activated cell sorting (FACS) analysis or radioimmunoprecipitation (RIA).

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a CA125/O772P polypeptide-expressing cancer if, after receiving a therapeutic amount of an anti-CA125/O772P antibody, such as a cysteine engineered anti-MUC16 antibody, or antibody drug conjugate thereof, according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the cysteine engineered anti-MUC16 antibody, or antibody drug conjugate thereof, may prevent growth and/or kill existing cancer cells, it may be cytostatic and/or cytotoxic. Reduction of these signs or symptoms may also be felt by the patient. The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

The terms "cancer" and "cancerous" refer to or describe the physiological condition in mammals that is typically characterized by unregulated cell growth. A "tumor" comprises one or more cancerous cells, and refers to all neoplastic cell growth and proliferation, whether malignant or benign, and all pre-cancerous and cancerous cells and tissues. Examples of cancer include, but are not limited to, carcinoma, lymphoma, blastoma, sarcoma, and leukemia or lymphoid malignancies. More particular examples of such cancers include ovarian cancer, squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, including pancreatic adenocarcinoma, glioblastoma, cervical cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A cancer which "overexpresses" an antigenic receptor is one which has significantly higher levels of the receptor, such as MUC16, at the cell surface thereof, compared to a noncancerous cell of the same tissue type. Such overexpression may be caused by gene amplification or by increased transcription or translation. Receptor overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 98/45479), southern blotting, northern blotting, or polymerase chain reaction (PCR) techniques, such as real time quantitative reverse-transcriptase PCR (qRT-PCR).

The terms "cell proliferative disorder" and "proliferative disorder" refer to disorders that are associated with some degree of abnormal cell proliferation. In one embodiment, the cell proliferative disorder is cancer.

The term "therapeutically effective amount" refers to an amount of a drug, e.g. a cysteine engineered anti-MUC16 antibody drug conjugate or chemotherapeutic agent, effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The term "cytostatic" refers to the effect of limiting the function of cells, such as limiting cellular growth or proliferation of cells. For cancer therapy, efficacy can, for example, be measured by assessing the time to disease progression (TTP) and/or determining the response rate (RR).

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK222584 (Novartis), oxaliplatin (Eloxatin®, Sanofi), 5-FU (5-fluorouracil), leucovorin, rapamycin (sirolimus, RAPAMUNE®, Wyeth), lapatinib (TYKERB®, GSK572016, GlaxoSmithKline), lonafarnib (SCH 66336), sorafenib (BAY43-9006, Bayer Labs.), capecitabine (XELODA®, Roche), docetaxel (TAXOTERE®), and gefitinib (IRESSA®, Astrazeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2', 2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylomithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY 117018, onapristone, and FARESTON. toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (x) anti-angiogenic agents such as bevacizumab (AVASTIN®, Genentech); and (xi) pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The following abbreviations are used herein and have the indicated definitions: Boc is N-(t-butoxycarbonyl), cit is citrulline (2-amirio-5-ureido pentanoic acid), dap is dolaproine, DCC is 1,3-dicyclohexylcarbodiimide, DCM is dichloromethane, DEA is diethylamine, DMSO is dimethylsulfoxide, DTNB is 5,5'-dithiobis(2-nitrobenzoic acid), DTPA is diethylenetriaminepentaacetic acid, DTT is dithiothreitol, Fmoc is N-(9-fluorenylmethoxycarbonyl), gly is glycine, HOBt is 1-hydroxybenzotriazole, HPLC is high pressure liquid chromatography, Mtr is 4-anisyldiphenylmethyl (or 4-methoxytrityl), PAB is p-aminobenzylcarbamoyl, PBS is phosphate-buffered saline (pH 7), PEG is polyethylene glycol, MC is 6-maleimidocaproyl, phe is L-phenylalanine, SEC is size-exclusion chromatography, TFA is trifluoroacetic acid, TLC is thin layer chromatography, UV is ultraviolet, and val is valine.

Cysteine Engineered Anti-MUC16 Antibodies

The compounds of the invention include cysteine engineered anti-MUC16 antibodies where one or more amino acids of any form of wild-type or parent anti-MUC16 antibody is replaced with a cysteine amino acid. The engineered cysteine amino acid is a free cysteine acid and not part of an intrachain or interchain disulfide unit. Any form of anti-MUC16 antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered anti-MUC16 antibodies of the invention include monoclonal antibodies, humanized or chimeric monoclonal antibodies, antigen-binding fragments of antibodies, fusion polypeptides and analogs that preferentially bind cell-associated MUC16 polypeptides.

Figure 12:
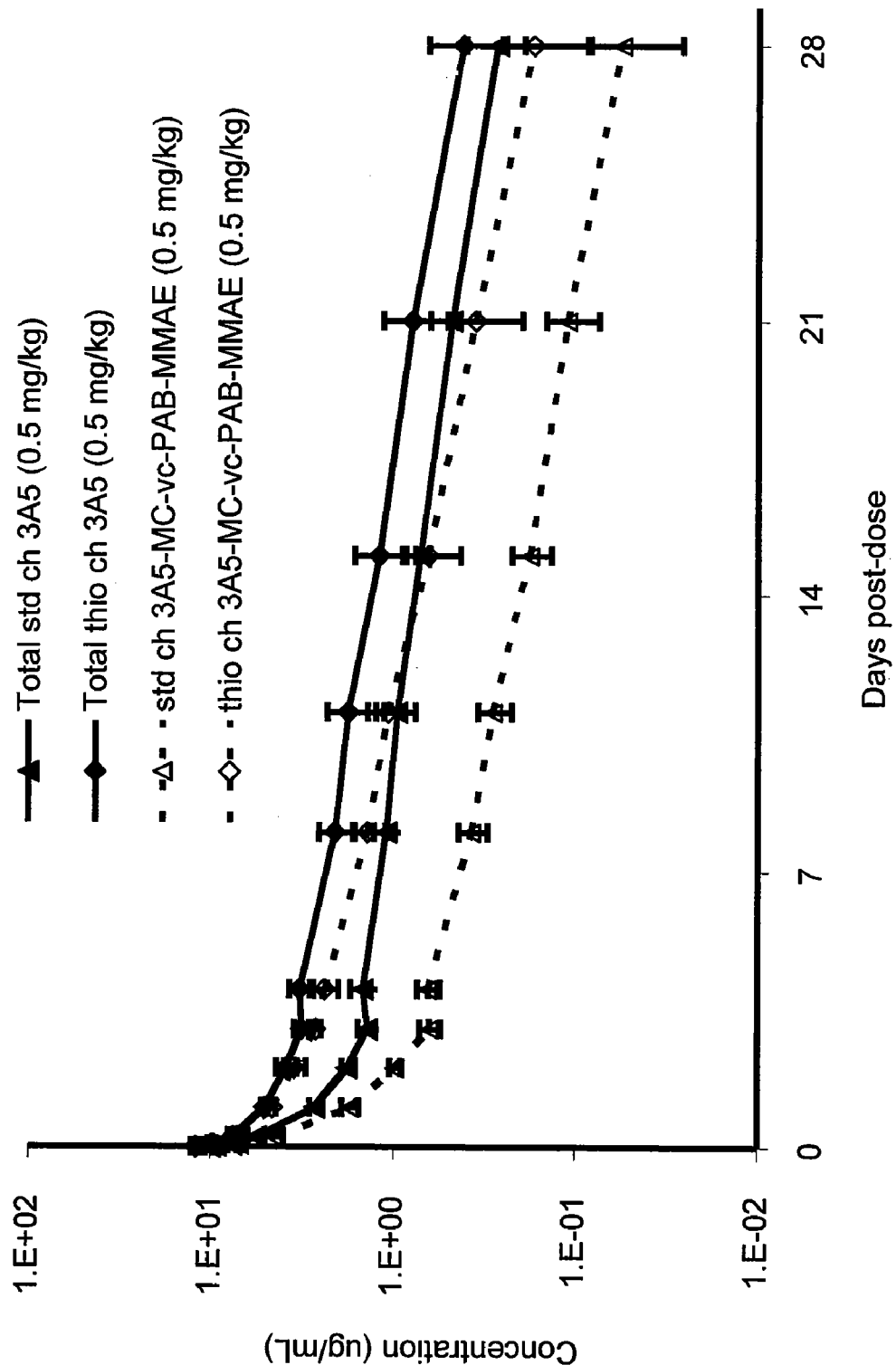
FIG. 12 shows a pharmacokinetic plot of plasma clearance over time after a single administration in rats of 0.5 mg/kg of: thio ch 3A5-MC-vc-PAB-MMAE and std ch 3A5-MC-vc-PAB-MMAE by measuring total antibody and ADC.

Cysteine engineered anti-MUC16 antibodies retain the antigen binding capability of their wild type, parent anti-MUC16 antibody counterparts. Thus, cysteine engineered anti-MUC16 antibodies are capable of binding to MUC16 antigens including receptor proteins O772P (CA125, MUC16, Genbank accession no. AF361486), as described in Yin et al J. (2001) Biol. Chem. 276 (29):27371-27375); WO2004045553 (claim 14); WO200292836 (claim 6; FIG. 12); WO200283866 (claim 15; Page 116-121); US2003124140 (Example 16); Cross-references: GI:34501467; AAK74120.3; AF361486_1.

A cysteine engineered anti-MUC16 antibody comprises one or more free cysteine amino acids with reduced sulfhydryl (thiol) groups wherein the cysteine engineered anti-MUC16 antibody binds to a MUC16 polypeptide.

In one embodiment, the cysteine engineered anti-MUC16 antibody is prepared by a process comprising replacing one or more amino acid residues of a parent anti-MUC16 antibody by cysteine.

Mutants with replaced ("engineered") cysteine (Cys) residues may be evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention may be in the ranges of 0.6 to 1.0; 0.7 to 1.0; or 0.8 to 1.0.

In one aspect, the invention concerns an isolated cysteine engineered anti-MUC16 antibody comprising an amino acid sequence that is encoded by a nucleotide sequence that hybridizes to the complement of a DNA molecule encoding (a) a cysteine engineered antibody having a full-length amino acid sequence as disclosed herein, (b) a cysteine engineered antibody amino acid sequence lacking the signal peptide as disclosed herein, (c) an extracellular domain of a transmembrane cysteine engineered antibody protein, with or without the signal peptide, as disclosed herein, (d) an amino acid sequence encoded by any of the nucleic acid sequences disclosed herein or (e) any other specifically defined fragment of a full-length cysteine engineered antibody amino acid sequence as disclosed herein.

In one aspect, the invention provides an isolated cysteine engineered anti-MUC16 antibody without the N-terminal signal sequence and/or without the initiating methionine and is encoded by a nucleotide sequence that encodes such an amino acid sequence as described in. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

Another aspect of the invention provides an isolated cysteine engineered anti-MUC16 antibody which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

In other embodiments, the invention provides isolated anti-MUC16 chimeric cysteine engineered antibodies comprising any of the herein described cysteine engineered antibody fused to a heterologous (non-MUC16) polypeptide. Examples of such chimeric molecules comprise any of the herein described cysteine engineered antibodies fused to a heterologous polypeptide such as, for example, an epitope tag sequence or an Fc region of an immunoglobulin.

The cysteine engineered anti-MUC16 antibody may be a monoclonal antibody, antibody fragment, chimeric antibody, humanized antibody, single-chain antibody or antibody that competitively inhibits the binding of an anti-MUC16 polypeptide antibody to its respective antigenic epitope. Antibodies of the present invention may optionally be conjugated to a growth inhibitory agent or cytotoxic agent such as a toxin, including, for example, an auristatin, an antibiotic, a radioactive isotope, a nucleolytic enzyme, or the like. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In other embodiments of the present invention, the invention provides vectors comprising DNA encoding any of the herein described cysteine engineered anti-MUC16 antibodies. Host cells comprising any such vector are also provided. By way of example, the host cells may be CHO cells, *E. coli* cells, or yeast cells. A process for producing any of the herein described polypeptides is further provided and comprises culturing host cells under conditions suitable for expression of the desired polypeptide and recovering the desired polypeptide from the cell culture.

Parent and cysteine engineered anti-MUC16 antibodies bind to a MUC16 polypeptide or MUC16 polypeptide variant described in "Compositions and Methods for the Diagnosis and Treatment of Tumor", WO 2007/001851, Dennis et al, U.S. Ser. No. 11/452,990, filed 14 Jun. 2006 to Genentech, Inc.) and are described as O772P, Ovarian carcinoma antigen CA125, or MUC16 Human, and in Genbank accession no. AF361486. Cross-references: GI:34501467; AAK74120.3; AF361486_1; Swiss-Prot entry Q8WX17.

A MUC16 polypeptide variant is a MUC16/CA125/O772P polypeptide having at least about 80% amino acid sequence identity with a MUC16 or CA125/O772P polypeptide sequence as disclosed in WO 2007/001851 which is a: (i) full-length native sequence; (ii) a polypeptide sequence lacking the signal peptide; (iii) an extracellular domain, with or without the signal peptide; (iv) or any other fragment of a full-length MUC16/CA125/O772P polypeptide sequence (such as those encoded by a nucleic acid that represents only a portion of the complete coding sequence for a full-length MUC16/CA125/O772P polypeptide). Such MUC16 polypeptide variants include, for instance, polypeptides wherein one or more amino acid residues are added, or deleted, at the N- or C-terminus of the full-length native amino acid sequence. Ordinarily, a MUC16 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence MUC16 polypeptide sequence, a MUC16 polypeptide sequence lacking the signal peptide, an extracellular domain of a MUC16 polypeptide, with or without the signal peptide, or any other specifically defined fragment of a full-length MUC16 polypeptide sequence. Ordinarily, MUC16 polypeptide variants are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, MUC16 variant polypeptides will have no more than one conservative amino acid substitution as compared to the native MUC16 polypeptide sequence, alternatively no more than 2, 3, 4, 5, 6, 7, 8, 9, or 10 conservative amino acid substitution as compared to the native MUC16 polypeptide sequence.

MUC16 polypeptides may be prepared by recombinant expression in: (i) *E. coli* with pBR322 vector; (ii) mammalian cells such as human HEK293 cells (ATCC CCL 1573), COS (simian fibroblast, SV-40) cells, Chinese Hamster Ovary (CHO) cells with the pRK5 vector; (iii) yeast, such as yeast strain AB110; or (iv) baculovirus-infected insect cells (WO 2007/001851). Native or recombinant MUC16 polypeptides may be purified by a variety of standard techniques in the art of protein purification. For example, pro-MUC16 polypeptide, mature MUC16 polypeptide, or pre-MUC16 polypeptide is purified by immunoaffinity chromatography using antibodies specific for the MUC16 polypeptide of interest. In general, an immunoaffinity column is constructed by covalently coupling the anti-MUC16 polypeptide antibody to an activated chromatographic resin. MUC16 polypeptides may be produced recombinantly as a fusion polypeptide with a heterologous polypeptide, which may be a signal sequence or other polypeptide having a specific cleavage site at the N-terminus of the mature protein or polypeptide. Alternatively, MUC16 polypeptides may be produced as fusion polypeptides with a signal sequence and a heterologous polypeptide sequence that allows purification of the MUC16 fusion polypeptide; examples of such polypeptides are polyhistidine ($HiS_6$ or $His_8$), human IgG Fc, the FLAG epitope (KDYKDDDDK), and the gD epitope (KYALADASLK-MADPNRFRGKDLPVL). The signal sequence may be a component of the vector, or it may be a part of the anti-MUC16 antibody- or MUC16 polypeptide-encoding DNA that is inserted into the vector. The signal sequence may be a prokaryotic signal sequence selected, for example, from the group of the alkaline phosphatase, penicillinase, 1pp; or heat-stable enterotoxin II leaders. For yeast secretion the signal sequence may be, e.g., the yeast invertase leader, alpha factor leader (including *Saccharomyces* and *Kluyveromyces* α-factor leaders (U.S. Pat. No. 5,010,182), or acid phosphatase leader, the *C. albicans* glucoamylase leader (EP 0362179), or the signal described in WO 90/13646. In mammalian cell expression, mammalian signal sequences may be used to direct secretion of the protein, such as signal sequences from secreted polypeptides of the same or related species, as well as viral secretory leaders.

A MUC16-expressing cell expresses an endogenous or transfected MUC16 polypeptide antigen either on the cell surface or in a secreted form. A MUC16-expressing cancer comprises cells that have a MUC16 polypeptide present on the cell surface or that produce and secrete a MUC16 antigenic polypeptide. A MUC16-expressing cancer optionally produces sufficient levels of MUC16 polypeptide on the surface of cells thereof, such that an anti-MUC16 antibody, or antibody drug conjugate thereof, can bind thereto and may exert a therapeutic effect with respect to the cancer. A cancer which overexpresses a MUC16 polypeptide is one which has significantly higher levels of MUC16 polypeptide at the cell surface thereof, or produces and secretes, compared to a noncancerous cell of the same tissue type. Such overexpression may be caused by gene amplification or by increased transcription or translation. MUC16 polypeptide overexpression may be determined in a clinical setting by evaluating increased levels of the MUC16 protein present on the surface of a cell, or secreted by the cell (e.g., via an immunohistochemistry assay using anti-MUC16 antibodies prepared against an isolated MUC16 polypeptide which may be prepared using recombinant DNA technology from an isolated nucleic acid encoding the MUC16 polypeptide; FACS analysis, etc.). Alternatively, or additionally, one may measure levels of MUC16 polypeptide-encoding nucleic acid or mRNA in the cell, e.g., via fluorescent in situ hybridization (FISH) using a nucleic acid based probe corresponding to a MUC16-encoding nucleic acid or the complement thereof; (WO 98/45479), Southern blotting, Northern blotting, or polymerase chain reaction (PCR) techniques, such as real time quantitative reverse-transcriptase PCR (qRT-PCR). One may also detect MUC16 polypeptide overexpression by measuring shed antigen in a biological fluid such as serum, e.g., using antibody-based assays (U.S. Pat. No. 4,933,294; WO 91/05264; U.S. Pat. No. 5,401,638; Sias et al (1990) J. Immunol. Methods 132:73-80). Various other in vivo assays may be contemplated. Alternatively, cells within the body of the patient may be exposed to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

Parent and cysteine engineered anti-MUC16 antibodies are capable of binding, preferably specifically, to a MUC16 polypeptide as described herein. MUC16 binding oligopeptides may be identified without undue experimentation using well known techniques. In this regard, it is noted that techniques for screening oligopeptide libraries for oligopeptides that are capable of specifically binding to a polypeptide target are well known in the art (U.S. Pat. No. 5,55,6762; U.S. Pat. No. 5,750,373; U.S. Pat. No. 4,708,871; U.S. Pat. No. 4,833, 092; U.S. Pat. No. 5,223,409; U.S. Pat. No. 5,403,484; U.S. Pat. No. 5,571,689; U.S. Pat. No. 5,663,143; WO 84/03506; WO84/03564; Geysen et al (1984) Proc. Natl. Acad. Sci. USA, 81:3998-4002; Geysen et al (1985) Proc. Natl. Acad. Sci. USA, 82:178-182; Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

The parent and cysteine engineered anti-MUC16 antibodies of the invention include polyclonal, monoclonal, humanized, human, bispecific, and heteroconjugate antibodies. Various forms of a humanized anti-MUC16 antibody are contemplated. For example, the humanized antibody may be an antibody fragment, such as a Fab. Alternatively, the humanized antibody may be an intact antibody, such as an intact IgG1 antibody.

Bispecific anti-MUC16 antibodies are antibodies that have binding specificities for at least two different epitopes. Exemplary bispecific anti-MUC16 antibodies may bind to two different epitopes of a MUC16 protein as described herein. Other such antibodies may combine a MUC16 binding site with a binding site for another protein. Alternatively, an anti-MUC16 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD 16), so as to focus and localize cellular defense mechanisms to the MUC16-expressing cell. Bispecific antibodies may also be used to localize cytotoxic agents to cells which express MUC16. These antibodies possess a MUC16-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies). Traditional production of full length bispecific antibodies is based on the co-expression of two immunoglobulin heavy chain-light chain pairs, where the two chains have different specificities (Millstein et al (1983) Nature 305:537-539).

Heteroconjugate anti-MUC16 antibodies are also within the scope of the present invention. Heteroconjugate antibodies are composed of two covalently joined antibodies. Such antibodies have, for example, been proposed to target immune system cells to unwanted cells (U.S. Pat. No. 4,676, 980), and for treatment of HIV infection (WO 91/00360; WO 92/200373; EP 03089). It is contemplated that the antibodies may be prepared in vitro using known methods in synthetic protein chemistry, including those involving crosslinking agents.

The anti-MUC16 antibodies of the present invention can be multivalent antibodies with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

The effector function of an anti-MUC16 antibody may be modified by introducing one or more amino acid substitutions in an Fc region. Such modification may enhance antigen-dependent cell-mediated cyotoxicity (ADCC) and/or complement dependent cytotoxicity (CDC) of the anti-MUC16 antibody. The homodimeric antibody thus generated may have improved internalization capability and/or increased complement-mediated cell killing and antibody-dependent cellular cytotoxicity (ADCC). See Caron et al (1992) J. Exp Med. 176:1191-1195 and Shopes, B. J. (1992) Immunol. 148:2918-2922. Homodimeric anti-MUC16 antibodies with enhanced anti-tumor activity may also be prepared using heterobifunctional cross-linkers as described in Wolff et al (1993) Cancer Research 53:2560-2565. Alternatively, an antibody can be engineered which has dual Fc regions and may thereby have enhanced complement lysis and ADCC capabilities (Stevenson et al (1989) Anti-Cancer Drug Design 3:219-230).

The serum half life of an anti-MUC16 antibody may be modulated by incorporating a salvage receptor binding epitope, e.g. an antibody fragment (U.S. Pat. No. 5,739,277). As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Monoclonal antibodies binding to MUC16 epitopes, including 3A5, are determined by standard competitive binding analysis and epitope mapping (WO 2007/001851), including cross-blocking studies by direct fluorescence on intact PC3 cells engineered to express MUC16 using the PANDEX™ Screen Machine to quantitate fluorescence (Fendly et al (1990) Cancer Research 50:1550-1558). Binding of monoclonal antibody 3A5 to OVCAR-3, OVCA-432 and SK-OV-3 cells was determined by standard flow cytometry analyses to parallel the expression level of MUC16 mRNA expressed in each of these three specific cell lines as determined by standard quantitative PCR analyses. More specifically, as determined by standard quantitative PCR analysis, OVCAR-3, OVCA-432 and SK-OV-3 cells express a high, moderate and low level of MUC16 mRNA, respectively. Flow cytometry analyses showed monoclonal anti-MUC16 antibody 3A5 binds quantitatively and parallels the relative amount of MUC16 mRNA present in those cell lines.

FIG. 3 shows alignment of humanized trastuzumab (anti HER2) light chain (HuTMAb-LC, SEQ ID NO:5), humanized std (standard, parent) 3A5 antiMUC16 light chain (Hu3A5-LC, SEQ ID NO:2), and chimeric std (standard, parent) 3A5 antiMUC16 light chain (Ch3A5-LC, SEQ ID NO:4) sequences (WO 2007/001851, incorporated by reference). The numbering follows the sequential numbering convention.

FIG. 4 shows alignment of humanized trastuzumab heavy chain (HuTMAb-HC, SEQ ID NO:6), humanized std 3A5 antiMUC16 heavy chain (Hu3A5-HC, SEQ ID NO:7), and chimeric std 3A5 antiMUC16 heavy chain (Ch3A5-HC, SEQ ID NO:8) sequences (WO 2007/001851, incorporated by reference). The numbering follows the sequential numbering convention. The label marking sequential number position 281 is actually 278 (Kabat 275; Eu 279).

Immunohistochemistry analysis was performed using 3A5 monoclonal antibodies (WO 2007/001851; Sambrook et al *Molecular Cloning: A Laboratory Manual*, New York: Cold Spring Harbor Press, 1989; Ausubel et al., *Current Protocols of Molecular Biology*, Unit 3.16, John Wiley and Sons, 1997). Monoclonal antibody 3A5 binds strongly to 16 of 20 human endometrioid adenocarcinoma tumor samples, 24 of 25 human serous ovarian cystadenocarcinoma samples and 5 of 10 human clear cell ovarian tumor samples.

Monoclonal antibody 3A5 becomes internalized into cells to which it binds MUC16 polypeptide on the cell surface. Specifically, OVCAR-3 cells were incubated for 18 hours with monoclonal antibody 3A5 and fluorescent dextran and then cell-associated 3A5 was quantitatively detected with a fluorescein-labeled anti-3A5 antibody. These analyses demonstrated that antibody 3A5 co-localizes with dextran, indicating trafficking of the 3A5 antibody into subcellular components of the incubated cells, including the lysosomal compartments of these cells.

Modifications of Anti-MUC16 Antibodies

Modifications and variations in the anti-MUC16 antibodies described herein, can be made, for example, using any of the techniques and guidelines known in the art for conservative and non-conservative mutations, for example, those in U.S. Pat. No. 5,364,934. Variations may be a substitution, deletion or insertion of one or more codons encoding the antibody or polypeptide that results in a change in the amino acid sequence as compared with the native sequence anti-MUC16 antibody. Optionally the variation is by substitution of at least one amino acid with any other amino acid in one or more of the domains of the anti-MUC16 antibody. The variations can be made using methods known in the art such as oligonucleotide-mediated (site-directed) mutagenesis, alanine scanning, and PCR mutagenesis. Site-directed mutagenesis (Carter et al (1986) Nucl. Acids Res., 13:4331; Zoller et al (1987) Nucl. Acids Res., 10:6487), cassette mutagenesis (Wells et al (1985) Gene, 34:315), restriction selection mutagenesis (Wells et al (1986) Philos. Trans. R. Soc. London SerA, 317:415) or other known techniques can be performed on the cloned DNA to produce the anti-MUC16 antibody variant DNA. Amino acid changes may alter post-translational processes of the anti-MUC16 antibody, such as changing the number or position of glycosylation sites or altering the membrane anchoring characteristics. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, (1983) W. H. Freeman & Co., San Francisco, pp. 79-86), acetylation of the N-terminal amine, and amidation of any C-terminal carboxyl group. Anti-MUC16 antibodies can be prepared by introducing appropriate nucleotide changes into the encoding DNA, and/or by chemical synthesis.

Anti-MUC16 antibody fragments may be truncated at the N-terminus or C-terminus, or may lack internal residues, for example, when compared with a full length anti-MUC16 antibody. Certain fragments lack amino acid residues that are not essential for a desired biological activity of the anti-MUC16 antibody. Anti-MUC16 antibody fragments may be prepared by any of a number of conventional techniques. Desired peptide fragments may be chemically synthesized. An alternative approach involves generating antibody fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or fragment, by polymerase chain reaction (PCR). Oligonucleotides that define the desired termini of the DNA fragment are employed at the 5' and 3' primers in the PCR. Preferably, anti-MUC16 antibody fragments share at least one biological and/or immunological activity with the native anti-MUC16 antibody disclosed herein.

A particularly preferred type of substitutional variant involves substituting one or more hypervariable region residues of a humanized or human antibody. Generally, the resulting variant(s) selected for further development will have improved biological properties relative to the antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human MUC16 polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of covalent modification of the anti-MUC16 antibody included within the scope of this invention comprises altering the native glycosylation pattern of the antibody or polypeptide by deleting one or more carbohydrate moieties found in native sequence anti-MUC16 antibody (either by removing the underlying glycosylation site or by deleting the glycosylation by chemical and/or enzymatic means), and/or adding one or more glycosylation sites that are not present in the native sequence anti-MUC16 antibody. In addition, the modification includes qualitative changes in the glycosylation of the native proteins, involving a change in the nature and proportions of the various carbohydrate moieties present. Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-Linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Addition of glycosylation sites to the anti-MUC16 antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the anti-MUC16 antibody (for O-linked glycosylation sites). The anti-MUC16 antibody amino acid sequence may optionally be altered through changes at the DNA level, particularly by mutating the DNA encoding the anti-MUC16 antibody at preselected bases such that codons are generated that will translate into the desired amino acids.

Another means of increasing the number of carbohydrate moieties on the anti-MUC16 antibody is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the anti-MUC16 antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties can be achieved by the use of a variety of endo- and exo-glycosidases as described by Thotakura et al (1987) Meth. Enzymol. 138:350.

Another type of covalent modification of anti-MUC16 antibody comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; U.S. Pat. No. 4,496,689; U.S. Pat. No. 4,301,144; U.S. Pat. No. 4,670,417; U.S. Pat. No. 4,791,192 or U.S. Pat. No. 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The anti-MUC16 antibody of the present invention may also be modified in a way to form chimeric molecules comprising an anti-MUC16 antibody fused to another, heterologous polypeptide or amino acid sequence. In one embodiment, such a chimeric molecule comprises a fusion of the anti-MUC16 antibody with a tag polypeptide which provides an epitope to which an anti-tag antibody can selectively bind. The epitope tag is generally placed at the amino- or carboxyl-terminus of the anti-MUC16 antibody. The presence of such epitope-tagged forms of the anti-MUC16 antibody can be detected using an antibody against the tag polypeptide. Also, provision of the epitope tag enables the anti-MUC16 antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al (1988) Mol. Cell. Biol., 8:2159-2165); the c-myc tag and the 8F9, 3C7, 6E10, G4, B7 and 9E10 antibodies thereto (Evan et al (1985) Molecular and Cellular Biology, 5:3610-3616); and the Herpes Simplex virus glycoprotein D (gD) tag and its antibody (Paborsky et al (1990) Protein Engineering, 3(6):547-553). Other tag polypeptides include the Flag-peptide (Hopp et al (1988) BioTechnology 6:1204-1210); the KT3 epitope peptide (Martin et al (1992) Science, 255:192-194); an α-tubulin epitope peptide (Skinner et al (1991) J. Biol. Chem., 266:15163-15166); and the T7 gene 10 protein peptide tag (Lutz-Freyermuth et al (1990) Proc. Natl. Acad. Sci. USA, 87:6393-6397).

In an alternative embodiment, the chimeric molecule may comprise a fusion of the anti-MUC16 antibody with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-MUC16 antibody in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule (U.S. Pat. No. 5,428,130).

Preparation of Anti-MUC16 Antibodies

DNA encoding an amino acid sequence variant of the cysteine engineered anti-MUC16 antibodies and parent anti-MUC16 antibodies of the invention is prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Ho et al (1989) Gene (Amst.) 77:51-59; Kunkel et al (1987) Proc. Natl. Acad. Sci. USA 82:488; Liu et al (1998) J. Biol. Chem. 273:20252-20260), PCR mutagenesis (Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733), and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993).

Phage display technology (McCafferty et al (1990) Nature 348:552-553) can be used to produce anti-MUC16 human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell (Johnson et al (1993) Current Opinion in Structural Biology 3:564-571; Clackson et al (1991) Nature, 352:624-628; Marks et al (1991) J. Mol. Biol. 222:581-597; Griffith et al (1993) EMBO J. 12:725-734; U.S. Pat. No. 5,565,332; U.S. Pat. No. 5,573,905; U.S. Pat. No. 5,567,610; U.S. Pat. No. 5,229,275).

Anti-MUC16 antibodies may be chemically synthesized using known oligopeptide synthesis methodology or may be prepared and purified using recombinant technology. The appropriate amino acid sequence, or portions thereof, may be produced by direct peptide synthesis using solid-phase techniques (Stewart et al., *Solid-Phase Peptide Synthesis*, (1969) W. H. Freeman Co., San Francisco, Calif.; Merrifield, (1963) J. Am. Chem. Soc., 85:2149-2154). In vitro protein synthesis may be performed using manual techniques or by automation. Automated solid phase synthesis may be accomplished, for instance, employing t-BOC or Fmoc protected amino acids and using an Applied Biosystems Peptide Synthesizer (Foster City, Calif.) using manufacturer's instructions. Various portions of the anti-MUC16 antibody or MUC16 polypeptide may be chemically synthesized separately and combined using chemical or enzymatic methods to produce the desired anti-MUC16 antibody or MUC16 polypeptide.

Various techniques have been developed for the production of antibody fragments. Traditionally, these fragments were derived via proteolytic digestion of intact antibodies (Morimoto et al (1992) Journal of Biochemical and Biophysical Methods 24:107-117; and Brennan et al (1985) Science, 229:81), or produced directly by recombinant host cells. Fab, Fv and ScFv anti-MUC16 antibody fragments can all be expressed in and secreted from *E. coli*, thus allowing the facile production of large amounts of these fragments. Antibody fragments can be isolated from the antibody phage libraries discussed herein. Alternatively, Fab'-SH fragments can be directly recovered from *E. coli* and chemically coupled to form F(ab')$_2$ fragments (Carter et al (1992) Bio/Technology 10:163-167), or isolated directly from recombinant host cell culture. The anti-MUC16 antibody may be a (scFv) single chain Fv fragment (WO 93/16185; U.S. Pat. No. 5,571,894; U.S. Pat. No. 5,587,458). The anti-MUC16 antibody fragment may also be a "linear antibody" (U.S. Pat. No. 5,641,870). Such linear antibody fragments may be monospecific or bispecific.

The description below relates primarily to production of anti-MUC16 antibodies by culturing cells transformed or transfected with a vector containing anti-MUC16 antibody-encoding nucleic acid. DNA encoding anti-MUC16 antibodies may be obtained from a cDNA library prepared from tissue believed to possess the anti-MUC16 antibody mRNA and to express it at a detectable level. Accordingly, human anti-MUC16 antibody or MUC16 polypeptide DNA can be conveniently obtained from a cDNA library prepared from human tissue. The anti-MUC16 antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding anti-MUC16 antibody or MUC16 polypeptide is PCR methodology (Sambrook et al., supra; Dieffenbach et al., *PCR Primer: A Laboratory Manual*, Cold Spring Harbor Laboratory Press, 1995).

Host cells are transfected or transformed with expression or cloning vectors described herein for anti-MUC16 antibody or MUC16 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, *Enterobacteriaceae* such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include *Enterobacteriaceae* such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is an exemplary host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)

169 degP ompTkan'; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease (U.S. Pat. No. 4,946,783). Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* may be faster and more cost efficient using, for example, expression of antibody fragments and polypeptides in bacteria with translation initiation regio (TIR) and signal sequences for optimizing expression and secretion (U.S. Pat. No. 5,648,237; U.S. Pat. No. 5,789,199; U.S. Pat. No. 5,840,523). After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-MUC16 antibody- or MUC16 polypeptide-encoding vectors. *Saccharomyces cerevisiae* is a commonly used lower eukaryotic host microorganism. Others include *Schizosaccharomyces pombe* (Beach and Nurse, (1981) Nature, 290: 140; EP 139,383); *Kluyveromyces* hosts (U.S. Pat. No. 4,943,529; Fleer et al (1991) Bio/Technology, 9:968-975) such as, e.g., *K. lactis* (MW98-8C, CBS683, CBS4574; Louvencourt et al (1983) J. Bacteriol., 154(2):737-742), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al (1990) Bio/Technology, 8:135), *K. thermotolerans*, and *K. marxianus; yarrowia* (EP 402226); *Pichia pastoris* (EP 183070; Sreekrishna et al (1988) J. Basic Microbiol., 28:265-278); *Candida; Trichoderma reesia* (EP 244234); *Neurospora crassa* (Case et al (1979) Proc. Natl. Acad. Sci. USA, 76:5259-5263); *Schwanniomyces* such as *Schwanniomyces occidentalis* (EP 394538); and filamentous fungi such as, e.g., *Neurospora, Penicillium, Tolypocladium* (WO 91/00357), and *Aspergillus* hosts such as *A. nidulans* (Ballance et al (1983) Biochem. Biophys. Res. Commun., 112:284-289; Tilbum et al (1983) Gene, 26:205-221; Yelton et al (1984) Proc. Natl. Acad. Sci. USA, 81: 1470-1474) and *A. niger* (Kelly and Hynes, (1985) EMBO J., 4:475-479). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*.

Suitable host cells for the expression of glycosylated anti-MUC16 antibody or MUC16 polypeptide may also be derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Examples of useful mammalian host cell lines are monkey kidney CV1 line transformed by SV40 (COS-7, ATCC CRL 1651); human embryonic kidney line (293 or 293 cells subcloned for growth in suspension culture, Graham et al (1977) J. Gen Virol. 36:59); baby hamster kidney cells (BHK, ATCC CCL 10); Chinese hamster ovary cells/-DHFR (CHO, Urlaub et al (1980) Proc. Natl. Acad. Sci. USA 77:4216); mouse sertoli cells (TM4, Mather (1980) Biol. Reprod. 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al (1982) Annals N.Y. Acad. Sci. 383:44-68); MRC 5 cells; FS4 cells; and a human hepatoma line (Hep G2).

Host cells are transformed with the above-described expression or cloning vectors for anti-MUC16 antibody production and cultured in conventional nutrient media modified as appropriate for inducing promoters, selecting transformants, or amplifying the genes encoding the desired sequences. The nucleic acid (e.g., cDNA or genomic DNA) encoding anti-MUC16 antibody or MUC16 polypeptide may be inserted into a replicable vector for cloning (amplification of the DNA) or for expression. The vector may, for example, be in the form of a plasmid, cosmid, viral particle, or phage. The appropriate nucleic acid sequence may be inserted into the vector by a variety of procedures.

Growth inhibition of tumor cells in vitro or in vivo can be determined in various ways known in the art, such as inhibiting cell proliferation of a MUC16-expressing tumor cell in vitro or in vivo by about 25-100% compared to the untreated tumor cell, or by about 30-100%, or by about 50-100% or 70-100%. The growth inhibitory effects of an anti-MUC16 antibody in vitro may be assessed by methods known in the art, e.g., using cells which express a MUC16 polypeptide either endogenously or following transfection with the MUC16 gene. For example, appropriate tumor cell lines and MUC16-transfected cells may treated with an anti-MUC16 monoclonal antibody at various concentrations for a few days (e.g., 2-7) days and stained with crystal violet or MTT or analyzed by some other colorimetric assay. A reduced signal indicates growth inhibition. Alternatively, cell viability can be measured by treating cells with an anti-MUC16 antibody or drug conjugate for a few days, then incubating the cells with a reagent that determines cell number as proportional to ATP content, for example by a luminescence assay using a reagent such as Cell TiterGlo (Promega, Madison, Wis.). Another method of measuring proliferation would be by comparing $^3$H-thymidine uptake by the cells treated in the presence or absence an anti-MUC16 antibody. After treatment, the cells are harvested and the amount of radioactivity incorporated into the DNA quantitated in a scintillation counter. Inhibition of proliferation would be demonstrated by a reduction of radioactivity. To select for an anti-MUC16 antibody which induces cell death, loss of membrane integrity as indicated by, e.g., propidium iodide (PI), trypan blue or 7AAD uptake, may be assessed relative to control. Appropriate positive controls include treatment of a selected cell line with a growth inhibitory antibody known to inhibit growth of that cell line. Growth inhibition can be measured at an antibody concentration of about 0.005 to 30 µg/ml or about 0.03 nM to 200 nM in cell culture, where the growth inhibition is determined 1-10 days after exposure of the tumor cells to the antibody. The antibody is growth inhibitory in vivo if administration of the anti-MUC16 antibody at about 1 µg/kg to about 100 mg/kg body weight results in reduction in tumor size or reduction of tumor cell proliferation within about 5 days to 3 months from the first administration of the antibody, preferably within about 5 to 30 days.

Preparation of Cysteine Engineered Anti-MUC16 Antibodies

The design, selection, and preparation methods of the invention enable cysteine engineered anti-MUC16 antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London). The amount of free thiol in a protein may be estimated by the standard Ellman's assay. Immunoglobulin M is an example of a disulfide-linked pentamer, while immunoglobulin G is an example of a protein with internal disulfide bridges bonding the subunits together. In proteins such as this, reduction of the disulfide bonds with a reagent such as dithiothreitol (DTT) or selenol (Singh et al (2002) Anal. Biochem. 304:147-156) is required to generate the reactive free thiol. This approach may result in loss of antibody tertiary structure and antigen binding specificity.

The PHESELECTOR (Phage ELISA for Selection of Reactive Thiols) Assay allows for detection of reactive cysteine groups in antibody-Fabs in an ELISA phage format thereby assisting in the design of cysteine engineered antibodies (US 2007/0092940). The antigen that binds to cysteine engineered antibody is coated on well surfaces, followed by incubation with phage particles displaying cysteine engineered Fabs, addition of HRP labeled secondary antibody, and absorbance detection. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

The PHESELECTOR assay allows screening of reactive thiol groups in antibodies. Identification of the heavy chain A114C Kabat numbering (A121C sequential numbering) variant in the trastuzsumab-Fab by this method is exemplary. The entire Fab molecule may be effectively searched to identify more ThioFab variants with reactive thiol groups. A parameter, fractional surface accessibility, was employed to identify and quantitate the accessibility of solvent to the amino acid residues in a polypeptide. The surface accessibility can be expressed as the surface area ($Å^2$) that can be contacted by a solvent molecule, e.g. water. The occupied space of water is approximated as a 1.4 Å radius sphere. Software is freely available or licensable (Secretary to CCP4, Daresbury Laboratory, Warrington, WA44AD, United Kingdom, Fax: (+44) 1925 603825, or by internet: www.ccp4.ac.uk/dist/html/INDEX.html) as the CCP4 Suite of crystallography programs which employ algorithms to calculate the surface accessibility of each amino acid of a protein with known x-ray crystallography derived coordinates ("The CCP4 Suite: Programs for Protein Crystallography" (1994) Acta. Cryst. D50:760-763). Two exemplary software modules that perform surface accessibility calculations are "AREAIMOL" and "SURFACE", based on the algorithms of B. Lee and F. M. Richards (1971) J. Mol. Biol. 55:379-400. AREAIMOL defines the solvent accessible surface of a protein as the locus of the centre of a probe sphere (representing a solvent molecule) as it rolls over the Van der Waals surface of the protein. AREAIMOL calculates the solvent accessible surface area by generating surface points on an extended sphere about each atom (at a distance from the atom centre equal to the sum of the atom and probe radii), and eliminating those that lie within equivalent spheres associated with neighboring atoms. AREAIMOL finds the solvent accessible area of atoms in a PDB coordinate file, and summarizes the accessible area by residue, by chain and for the whole molecule. Accessible areas (or area differences) for individual atoms can be written to a pseudo-PDB output file. AREAIMOL assumes a single radius for each element, and only recognizes a limited number of different elements.

AREAIMOL and SURFACE report absolute accessibilities, i.e. the number of square Angstroms (Å). Fractional surface accessibility is calculated by reference to a standard state relevant for an amino acid within a polypeptide. The reference state is tripeptide Gly-X-Gly, where X is the amino acid of interest, and the reference state should be an 'extended' conformation, i.e. like those in beta-strands. The extended conformation maximizes the accessibility of X. A calculated accessible area is divided by the accessible area in a Gly-X-Gly tripeptide reference state and reports the quotient, which is the fractional accessibility. Percent accessibility is fractional accessibility multiplied by 100. Another exemplary algorithm for calculating surface accessibility is based on the SOLV module of the program xsae (Broger, C., F. Hoffman-LaRoche, Basel) which calculates fractional accessibility of an amino acid residue to a water sphere based on the X-ray coordinates of the polypeptide. The fractional surface accessibility for every amino acid in an antibody may be calculated using available crystal structure information (Eigenbrot et al. (1993) J Mol Biol. 229:969-995).

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or other mammalian host cells, such as myeloma cells (U.S. Pat. No. 5,807,715; US 2005/0048572; US 2004/0229310) that do not otherwise produce the antibody protein, to obtain the synthesis of monoclonal antibodies in the recombinant host cells.

Sites were identified that do not interfere with antibody effector functions and substitute them with cysteine residues for site-specific labeling. The constant region of the antibody Fab ($CL$ and $CH_1$) is ideally situated for this purpose, as this domain has no apparent role in antigen binding or in Fc-effector functions (Jefferis, R. "Structure-function relationships of the IgG subclasses," in The Human IgG Subclasses.

(Pergamon Press, Oxford; 1990). The PHESELECTOR phage display based method to screen reactive cysteines on the Fab surface identified the variants LC-V110C (Kabat numbering) and HC-A114C (Kabat numbering, equivalent to A118C in Eu numbering and A117C in sequential numbering for anti-MUC16 antibody), as well as others, as being suitable for site-specific labeling of antibody-Fabs (Junutula, J. R. et al. (2008) "Rapid identification of reactive cysteine residues for site-specific labeling of antibody-Fabs" J Immunol Methods 332:41-52.

After design and selection, cysteine engineered antibodies, e.g. ThioFabs, with the engineered, highly reactive unpaired Cys residues, may be produced by: (i) expression in a bacterial, e.g. *E. coli*, system (Skerra et al (1993) Curr. Opinion in Immunol. 5:256-262; Pluckthun (1992) Immunol. Revs. 130: 151-188) or a mammalian cell culture system (WO 01/00245), e.g. Chinese Hamster Ovary cells (CHO); and (ii) purification using common protein purification techniques (Lowman et al (1991) J. Biol. Chem. 266(17): 10982-10988).

The engineered Cys thiol groups react with electrophilic linker reagents and drug-linker intermediates to form cysteine engineered antibody drug conjugates and other labelled cysteine engineered antibodies. Cys residues of cysteine engineered antibodies, and present in the parent antibodies, which are paired and form interchain and intrachain disulfide bonds do not have any reactive thiol groups (unless treated with a reducing agent) and do not react with electrophilic linker reagents or drug-linker intermediates. The newly engineered Cys residue, can remain unpaired, and able to react with, i.e. conjugate to, an electrophilic linker reagent or drug-linker intermediate, such as a drug-maleimide. Exemplary drug-linker intermediates include: MC-MMAE, MC-MMAF, MC-vc-PAB-MMAE, and MC-vc-PAB-MMAF. The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) starting at the N-terminus, differs from the Kabat numbering scheme (bottom row) by insertions noted by a,b,c. Using the Kabat numbering system, the actual linear amino acid sequence may contain fewer or additional amino acids corresponding to a shortening of, or insertion into, a FR or CDR of the variable domain. The cysteine engineered heavy chain variant sites are identified by the sequential numbering and Kabat numbering schemes.

In one embodiment, the cysteine engineered anti-MUC16 antibody is prepared by a process comprising:

(a) replacing one or more amino acid residues of a parent anti-MUC16 antibody by cysteine; and (b) determining the thiol reactivity of the cysteine engineered anti-MUC16 antibody by reacting the cysteine engineered antibody with a thiol-reactive reagent.

The cysteine engineered antibody may be more reactive than the parent antibody with the thiol-reactive reagent.

The free cysteine amino acid residues may be located in the heavy or light chains, or in the constant or variable domains. Antibody fragments, e.g. Fab, may also be engineered with one or more cysteine amino acids replacing amino acids of the antibody fragment, to form cysteine engineered antibody fragments.

Another embodiment of the invention provides a method of preparing (making) a cysteine engineered anti-MUC16 antibody, comprising:

(a) introducing one or more cysteine amino acids into a parent anti-MUC16 antibody in order to generate the cysteine engineered anti-MUC16 antibody; and (b) determining the thiol reactivity of the cysteine engineered antibody with a thiol-reactive reagent;

wherein the cysteine engineered antibody is more reactive than the parent antibody with the thiol-reactive reagent.

Step (a) of the method of preparing a cysteine engineered antibody may comprise:

(i) mutagenizing a nucleic acid sequence. encoding the cysteine engineered antibody;

(ii) expressing the cysteine engineered antibody; and (iii) isolating and purifying the cysteine engineered antibody.

Step (b) of the method of preparing a cysteine engineered antibody may comprise expressing the cysteine engineered antibody on a viral particle selected from a phage or a phagemid particle.

Step (b) of the method of preparing a cysteine engineered antibody may also comprise:

(i) reacting the cysteine engineered antibody with a thiol-reactive affinity reagent to generate an affinity labelled, cysteine engineered antibody; and (ii) measuring the binding of the affinity labelled, cysteine engineered antibody to a capture media.

Another embodiment of the invention is a method of screening cysteine engineered antibodies with highly reactive, unpaired cysteine amino acids for thiol reactivity comprising:

(a) introducing one or more cysteine amino acids into a parent antibody in order to generate a cysteine engineered antibody;

(b) reacting the cysteine engineered antibody with a thiol-reactive affinity reagent to generate an affinity labelled, cysteine engineered antibody; and (c) measuring the binding of the affinity labelled, cysteine engineered antibody to a capture media; and (d) determining the thiol reactivity of the cysteine engineered antibody with the thiol-reactive reagent.

Step (a) of the method of screening cysteine engineered antibodies may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of screening cysteine engineered antibodies may comprise expressing the cysteine engineered antibody on a viral particle selected from a phage or a phagemid particle.

Step (b) of the method of screening cysteine engineered antibodies may also comprise:

(i) reacting the cysteine engineered antibody with a thiol-reactive affinity reagent to generate an affinity labelled, cysteine engineered antibody; and (ii) measuring the binding of the affinity labelled, cysteine engineered antibody to a capture media.

Cysteine Engineering of 3A5 IG Variants

Cysteine was introduced at the heavy chain 117 (sequential numbering for anti-MUC16 3A5 antibody) site into full-length, humanized and chimeric parent monoclonal anti-MUC16 3A5 antibodies by the cysteine engineering methods described herein to give A117C thio hu anti-MUC16 3A5 humanized variant with heavy chain sequence: SEQ ID NO:

1, and light chain sequence: SEQ ID NO:2, FIG. 1, and A117C thio ch anti-MUC16 3A5 chimeric variant with heavy chain sequence: SEQ ID NO:3, and light chain sequence: SEQ ID NO:4, FIG. 2. These cysteine engineered monoclonal antibodies were expressed in CHO (Chinese Hamster Ovary) cells by transient fermentation in media containing 1 mM cysteine.

Affinities of humanized thio anti-MUC16 cysteine engineered antibodies and standard 3A5 IgG were compared by flow cytometry on OVCAR-3 cells (which express endogenous MUC16), serially diluting the antibodies until a reduced shift was observed; binding conditions were selected such that antibodies were in excess of cellular binding sites throughout the titration. Bound antibody was detected using a fluorescent anti-human Fc secondary antibody. Flow cytometry histograms showed binding at saturating (400 ng/mL) and subsaturating (25 ng/mL) concentrations. At all antibody concentrations analyzed, the two anti-MUC16 variants, standard and thio, gave equivalent binding, suggesting equivalent affinities for the antigen. At each concentration tested, thio anti-MUC16 antibody bound to OVCAR-3 cells as efficiently as standard (parent) anti-MUC16 antibody. Surface plasmon resonance analyses using portions of the MUC16 extracellular domain (ECD) also confirmed the high affinity of the thio 3A5 anti-MUC16 antibody for this antigen ($K_D$=116 pM). Comparing cells with high or low/absent MUC16 expression based on RT-PCR studies, thio anti-MUC16 antibody binds to cells that express MUC16 but not to MUC16-negative cell lines. Therefore substitution at HC-A118 does not affect antigen binding.

According to one embodiment, humanized 3A5 cysteine engineered anti-MUC16 antibodies comprise one or more of the following variable region heavy chain sequences with a free cysteine amino acid (SEQ ID NOS: 9-17, Table 1).

TABLE 1

Comparison of heavy chain Sequential, Kabat and Eu numbering for hu 3A5 cysteine engineered anti-MUC16 antibody variants

| Sequence | Sequential Numbering | Kabat Numbering | EU Numbering | SEQ ID NO: |
|---|---|---|---|---|
| EVQLCESGGG | V5C | V5C | | 9 |
| LRLSCCASGYS | A23C | A23C | | 10 |
| MNSLRCEDTAV | A88C | A84C | | 11 |
| TLVTVCSASTK | S115C | S112C | | 12 |
| VTVSSCSTKGP | A117C | A114C | A118C | 13 |
| VSSASCKGPSV | T119C | T116C | T120C | 14 |
| WYVDGCEVHNA | V281C | V278C | V282C | 15 |
| KGFYPCDIAVE | S374C | S371C | S375C | 16 |
| PPVLDCDGSFF | S399C | S396C | S400C | 17 |

According to one embodiment, chimeric 3A5 cysteine engineered anti-MUC16 antibodies comprise one or more of the following variable region heavy chain sequences with a free cysteine amino acid (SEQ ID NOS: 18-26, Table 2).

TABLE 2

Comparison of heavy chain Sequential, Kabat and Eu numbering for predicted ch 3A5 cysteine engineered anti-MUC16 antibody variants

| Sequence | Sequential Numbering | Kabat Numbering | EU Numbering | SEQ ID NO: |
|---|---|---|---|---|
| DVQLCESGPG | Q5C | Q5C | | 18 |
| LSLTCCVTGYS | T23C | T23C | | 19 |
| LNSVTCEDTAT | T88C | T84C | | 20 |
| TLVTVCAASTK | S115C | S112C | | 21 |
| VTVSACSTKGP | A117C | A114C | A118C | 22 |
| VSAASCKGPSV | T119C | T116C | T120C | 23 |
| WYVDGCEVHNA | V281C | V278C | V282C | 24 |
| KGFYPCDIAVE | S374C | S371C | S375C | 25 |
| PPVLDCDGSFF | S399C | S396C | S400C | 26 |

According to one embodiment, humanized 3A5 cysteine engineered anti-MUC16 antibodies comprise one or more of the following variable region light chain sequences with a free cysteine amino acid (SEQ ID NOS: 27-33, Table 3).

TABLE 3

Comparison of light chain Sequential and Kabat numbering for hu 3A5 cysteine engineered anti-MUC16 antibody variants

| Sequence | Sequential Numbering | Kabat Numbering | SEQ ID NO: |
|---|---|---|---|
| SLSASCGDRVT | V15C | V15C | 27 |
| EIKRTCAAPSV | V110C | V110C | 28 |
| TVAAPCVFIFP | S114C | S114C | 29 |
| FTFPPCDEQLK | S121C | S121C | 30 |
| DEQLKCGTASV | S127C | S127C | 31 |
| VTEQDCKDSTY | S168C | S168C | 32 |
| GLSSPCTKSFN | V205C | V205C | 33 |

According to one embodiment, chimeric 3A5 cysteine engineered anti-MUC16 antibodies comprise one or more of the following variable region light chain sequences with a free cysteine amino acid (SEQ ID NOS: 34-40, Table 4).

TABLE 4

Comparison of light chain Sequential and Kabat numbering for ch 3A5 cysteine engineered anti-MUC16 antibody variants

| Sequence | Sequential Numbering | Kabat Numbering | SEQ ID NO: |
|---|---|---|---|
| FLSVSCGGRVT | L15C | L15C | 34 |
| EIKRTCAAPSV | V110C | V110C | 35 |

TABLE 4-continued

Comparison of light chain Sequential and Kabat numbering for ch 3A5 cysteine engineered anti-MUC16 antibody variants

| Sequence | Sequential Numbering | Kabat Numbering | SEQ ID NO: |
|---|---|---|---|
| TVAAP<u>C</u>VFIFP | S114C | S114C | 36 |
| FIFPP<u>C</u>DEQLK | S121C | S121C | 37 |
| DEQLK<u>C</u>GTASV | S127C | S127C | 38 |
| VTEQD<u>C</u>KDSTY | S168C | S168C | 39 |
| GLSSP<u>C</u>TKSFN | V205C | V205C | 40 |

Labelled Cysteine Engineered Anti-MUC16 Antibodies

Cysteine engineered anti-MUC16 antibodies may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g., a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

The exemplary methods described here may be applied generally to the identification and production of antibodies, and more generally, to other proteins through application of the design and screening steps described herein.

Such an approach may be applied to the conjugation of other thiol-reactive reagents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The thiol-reactive reagent may be a drug moiety, a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

Uses of Cysteine Engineered Anti-MUC16 Antibodies

Cysteine engineered anti-MUC16 antibodies, and antibody-drug conjugates and labelled conjugates thereof may find use as therapeutic and/or diagnostic agents. The present invention further provides methods of preventing, managing, treating or ameliorating one or more symptoms associated with a MUC16 related disorder. In particular, the present invention provides methods of preventing, managing, treating, or ameliorating one or more symptoms associated with a cell proliferative disorder, such as cancer, e.g., ovarian cancer, cervical cancer, uterine cancer, pancreatic cancer, including pancreatic adenocarcinoma, lung cancer and breast cancer. The present invention still further provides methods for diagnosing a MUC16 related disorder or predisposition to developing such a disorder, as well as methods for identifying antibodies, and antigen-binding fragments of antibodies, that preferentially bind cell-associated MUC16 polypeptides.

Another embodiment of the present invention is directed to the use of a cysteine engineered anti-MUC16 antibody for the preparation of a medicament useful in the treatment of a MUC16 related disorder.

Cysteine Engineered Anti-MUC16 Antibody-Drug Conjugates

The cysteine engineered anti-MUC16 antibodies resolve the issue of antibody-drug conjugate heterogeneity by directing the attachment of drug moieties at defined sites and with near-uniform stoichiometry (drug/antibody ratio, p value). Additionally, the conjugation conditions results in retention of all the native immunoglobulin disulfide bonds.

An aspect of the invention is an antibody-drug conjugate compound comprising a cysteine engineered anti-MUC16 antibody (Ab), and an auristatin drug moiety (D) wherein the cysteine engineered antibody is attached through one or more free cysteine amino acids by a linker moiety (L) to D; the compound having Formula I:

$$\text{Ab-(L-D)}_p \qquad\qquad \text{I}$$

where p is 1, 2, 3, or 4; and wherein the cysteine engineered antibody is prepared by a process comprising replacing one or more amino acid residues of a parent anti-MUC16 antibody by one or more free cysteine amino acids. When a single cysteine mutation is engineered into the anti-MUC16 parent antibody to form the cysteine engineered anti-MUC16 antibody, two free cysteine amino acids result due to the symmetrical nature of the heavy chains and light chains.

Figure 5:
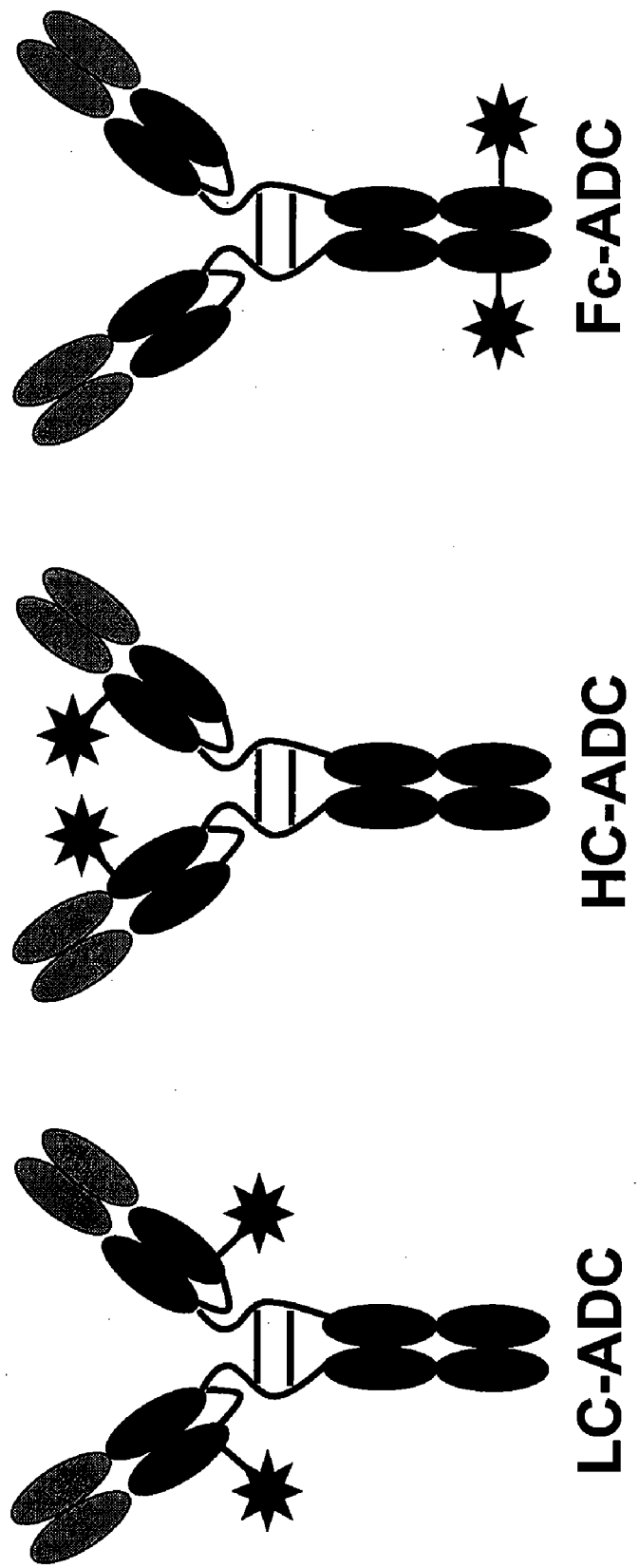
FIG. 5 shows depictions of cysteine engineered anti-MUC16 antibody drug conjugates (ADC) where a drug moiety is attached to an engineered cysteine group in: the light chain (LC-ADC); the heavy chain (HC-ADC); and the Fc region (Fc-ADC).

FIG. 5 shows embodiments of cysteine engineered anti-MUC16 antibody drug conjugates (ADC) where an auristatin drug moiety is attached to an engineered cysteine group in: the light chain (LC-ADC); the heavy chain (HC-ADC); and the Fc region (Fc-ADC).

Conventional antibody-drug conjugation strategies yield heterogeneous mixtures of conjugates that are active on target cells but may also produce systemic toxicities. Potential advantages of cysteine engineered anti-MUC16 antibody drug conjugates include improved safety (larger therapeutic index), improved PK parameters, greater stability and preservation of binding due to retention of the antibody interchain disulfide bonds, defined sites of drug conjugation, and a more nearly homogeneous product mixture. In fact, the thio anti-MUC16 ADC exhibit a larger therapeutic window (approximately four-fold) in pre-clinical animal models than standard anti-MUC16 ADC. When comparing matched IgG antibody (mg/kg) dose levels, our data show equivalent efficacy of the thio and standard MUC16 ADC in mouse xenografts, whereas in rats the 68.6 mg/kg (2820 μg/m² MMAE) dose of the thio ADC exerts similar toxicities as the 16.6 mg/kg (1500 μg/m² MMAE) dose of the standard ADC. When compared in terms of cytotoxic drug dose (μg/m²), the thio ADC is both safer and more efficacious than the standard ADC. A resulting benefit of the thio ADC over the standard ADC would be to reduce the MMAE exposure at an efficacious (mg/kg) dose of ADC. In turn, the improved tolerability of the thio ADC could permit higher dose levels on a mg/kg antibody basis, and to produce a therapeutic benefit for patients with more challenging malignancies, for example, with relatively less sensitivity to MMAE or relatively lower levels of MUC16 expression.

Drug Moieties

Auristatin drug moieties of the antibody-drug conjugates (ADC) of Formula I include dolastatins, auristatins (U.S. Pat. No. 5,635,483; U.S. Pat. No. 5,780,588; U.S. Pat. No. 5,767,237; U.S. Pat. No. 6,124,431), and analogs and derivatives thereof. Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). Various forms of a dolastatin or auristatin drug moiety may be covalently attached to an antibody through the N (amino) terminus or the C (carboxyl) terminus of the peptidic drug moiety (WO 02/088172; Doronina et al (2003) Nature Biotechnology 21(7):778-784; Francisco et al (2003) Blood 102 (4):1458-1465).

Exemplary auristatin embodiments include the N-terminus linked monomethylauristatin drug moieties DE and DF, disclosed in: WO 2005/081711; Senter et al, Proceedings of the American Association for Cancer Research, Volume 45, Abstract Number 623, presented Mar. 28, 2004, the disclosure of each which are expressly incorporated by reference in their entirety. Exemplary auristatin drug moieties include MMAE, and MMAF.

The auristatin drug moiety (D) of the antibody-drug conjugates (ADC) of Formula I include the monomethylauristatin drug moieties MMAE and MMAF. The N-terminus of the MMAE or MMAF drug moiety is covalently attached via a linker to a engineered cysteine of the antibody.

Linkers

"Linker", "Linker Unit", or "link" means a chemical moiety comprising a covalent bond or a chain of atoms that covalently attaches an antibody to a drug moiety. In various embodiments, a linker is specified as L. A "Linker" (L) is a bifunctional or multifunctional moiety which can be used to link one or more Drug moieties (D) and an antibody unit (Ab) to form antibody-drug conjugates (ADC) of Formula I. Antibody-drug conjugates (ADC) can be conveniently prepared using a Linker having reactive functionality for binding to the Drug and to the Antibody. A cysteine thiol of a cysteine engineered antibody (Ab) can form a bond with an electrophilic functional group of a linker reagent, a drug moiety or drug-linker intermediate.

In one aspect, a Linker has a reactive site which has an electrophilic group that is reactive to a nucleophilic cysteine present on an antibody. The cysteine thiol of the antibody is reactive with an electrophilic group on a Linker and forms a covalent bond to a Linker. Useful electrophilic groups include, but are not limited to, maleimide and haloacetamide groups.

Linkers include a divalent radical such as an alkyldiyl, an arylene, a heteroarylene, moieties such as: —(CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Cysteine engineered antibodies react with linker reagents or drug-linker intermediates, with electrophilic functional groups such as maleimide or α-halo carbonyl, according to

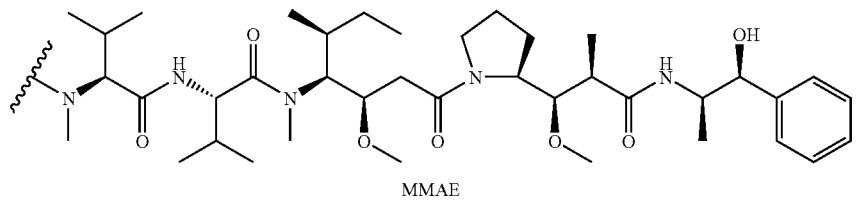

MMAE

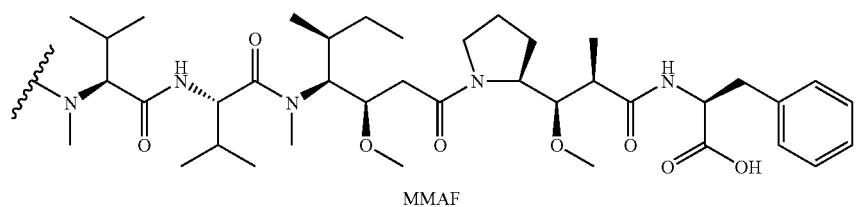

MMAF

Other exemplary auristatin drug moieties include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

the conjugation method at page 766 of Klussman, et al (2004), Bioconjugate Chemistry 15(4):765-773, and according to the protocol of Example 3.

The linker may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), N-succinimidyl 4-(2-pyridylthio) pentanoate ("SPP"), N-succinimidyl 4-(N-maleimidomethyl) cyclohexane-1 carboxylate ("SMCC"), N-Succinimidyl (4-iodo-acetyl) aminobenzoate ("SIAB"), ethyleneoxy —CH$_2$CH$_2$O— as one or more repeating units ("EO" or "PEO"). Additional linker components are known in the art and some are described herein.

In one embodiment, linker L of an ADC has the formula:

-A$_a$-W$_w$—Y$_y$— wherein:

-A- is a Stretcher unit covalently attached to a cysteine thiol of the antibody (Ab);

a is 0 or 1;

each —W— is independently an Amino Acid unit;

w is independently an integer ranging from 0 to 12;

—Y— is a Spacer unit covalently attached to the drug moiety; and y is 0, 1 or 2.

Stretcher Unit

The Stretcher unit (-A-), when present, is capable of linking an antibody unit to an amino acid unit (—W—). In this regard an antibody (Ab) has a free cysteine thiol group that can form a bond with an electrophilic functional group of a Stretcher Unit. Exemplary stretcher units in Formula I conjugates are depicted by Formulas II and III, wherein Ab-, —W—, —Y—, -D, w and y are as defined above, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—$(C_3$-$C_8$ carbocyclyl), $(C_3$-$C_8$ carbocyclyl)-$(CH_2)_r$, $C_3$-C8 heterocyclyl, $(CH_2)_r$—$(C_3$-$C_8$ heterocyclyl), —$(C_3$-$C_8$ heterocyclyl)-$(CH_2)_r$—, —$(CH_2)_rC(O)NR^b(CH_2)_r$, —$(CH_2CH_2O)_r$—, —$(CH_2CH_2O)_r$—, —$CH_2$—, —$(CH_2)_rC(O)NR^b(CH_2CH_2O)_r$—, —$(CH_2)_rC(O)NR^b(CH_2CH_2O)_r$—$CH_2$—, —$(CH_2CH_2O)_rC(O)NR^b(CH_2CH_2O)_r$—, —$(CH_2CH_2O)_rC(O)NR^b(CH_2CH_2O)_r$—$CH_2$—, and —$(CH_2CH_2O)_rC(O)NR^b(CH_2)_r$—; where $R^b$ is H, $C_1$-$C_6$ alkyl, phenyl, or benzyl; and r is independently an integer ranging from 1-10.

Arylene includes divalent aromatic hydrocarbon radicals of 6-20 carbon atoms derived by the removal of two hydrogen atoms from the aromatic ring system. Typical arylene groups include, but are not limited to, radicals derived from benzene, substituted benzene, naphthalene, anthracene, biphenyl, and the like.

Heterocyclyl groups include a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbocyclyl groups include a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cylopent-3-enyl, cyclohexyl, 1-cyclohex-1-enyl, 1-cyclohex-2-enyl, 1-cyclohex-3-enyl, cycloheptyl, and cyclooctyl.

It is to be understood from all the exemplary embodiments of Formula I ADC such as II-V, that even where not denoted expressly, from 1 to 4 drug moieties are linked to an antibody (p=1-4), depending on the number of engineered cysteine residues.

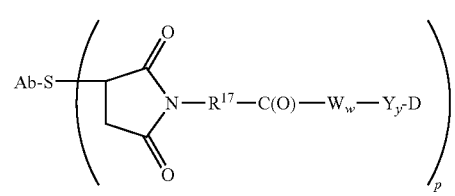

An illustrative Formula II Stretcher unit is derived from maleimido-caproyl (MC) wherein $R^{17}$ is —$(CH_2)_5$—:

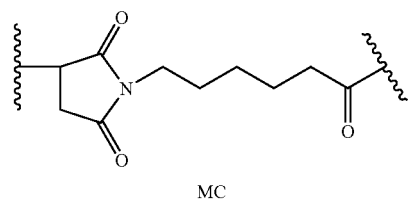

MC

An illustrative Stretcher unit of Formula II, and is derived from maleimido-propanoyl (MP) wherein $R^{17}$ is —$(CH_2)_2$—:

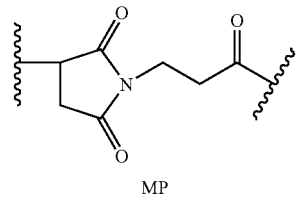

MP

Another illustrative Stretcher unit of Formula II wherein $R^{17}$ is —$(CH_2CH_2O)_r$—$CH_2$— and r is 2:

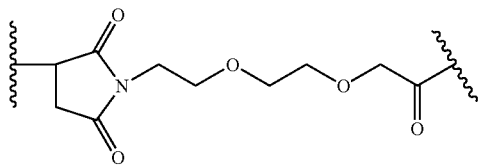

Another illustrative Stretcher unit of Formula II wherein $R^{17}$ is —$(CH_2)_rC(O)NR^b(CH_2CH_2O)_r$—$CH_2$— where $R^b$ is H and each r is 2:

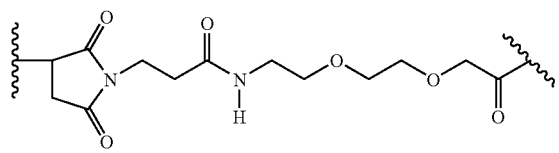

MPEG

Ab-S—(—CH$_2$—CONH—R$^{17}$—C(O)—W$_w$—Y$_y$-D)$_p$     III

An illustrative Stretcher unit of Formula II wherein $R^{17}$ is —$(CH_2)_5$—:

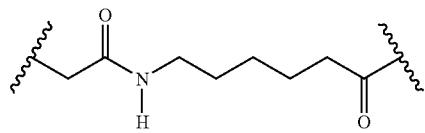

In another embodiment, the Stretcher unit is linked to the cysteine engineered anti-MUC16 antibody via a disulfide bond between the engineered cysteine sulfur atom of the antibody and a sulfur atom of the Stretcher unit. A representative Stretcher unit of this embodiment is depicted by Formula IV, wherein $R^{17}$, Ab-, —W—, —Y—, -D, w and y are as defined above.

Ab-S—(—S—R$^{17}$—C(O)—W$_w$—Y$_y$-D)$_p$     IV

In yet another embodiment, the reactive group of the Stretcher contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted by Formulas Va and Vb, wherein —$R^{17}$—, Ab-, —W—, —Y—, -D, w and y are as defined above;

Ab-S—(—C(O)NH—R$^{17}$—C(O)—W$_w$—Y$_y$-D)$_p$     Va

Ab-S—(—C(S)NH—R$^{17}$—C(O)—W$_w$—Y$_y$-D)$_p$     Vb

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Amino Acid Unit

The linker may comprise amino acid residues. The Amino Acid unit (—$W_w$—), when present, links the antibody (Ab) to the drug moiety (D) of the cysteine engineered antibody-drug conjugate (ADC) of the invention.

—$W_w$— is a dipeptide, tripeptide, tetrapeptide, pentapeptide, hexapeptide, heptapeptide, octapeptide, nonapeptide, decapeptide, undecapeptide or dodecapeptide unit. Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

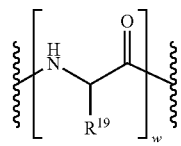

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

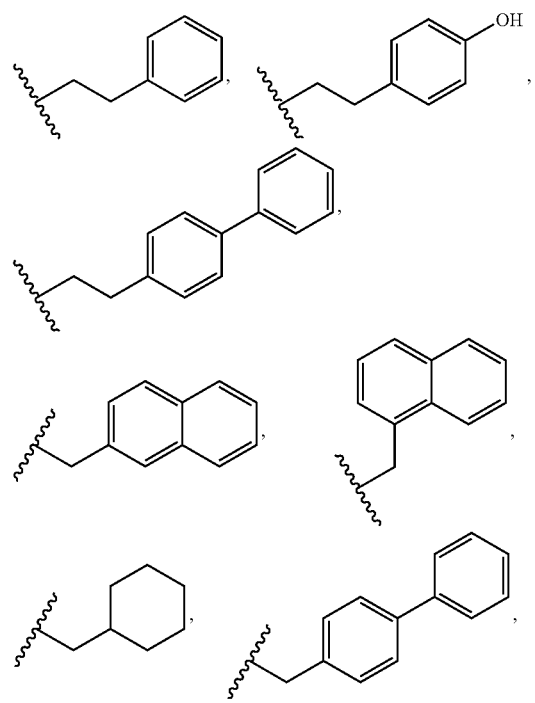

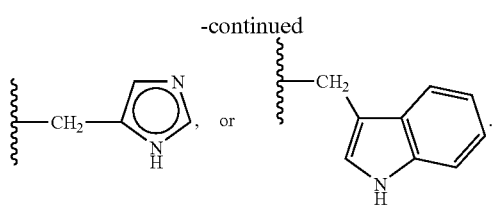

When $R^{19}$ is other than hydrogen, the carbon atom to which $R^{19}$ is attached is chiral. Each carbon atom to which $R^{19}$ is attached is independently in the (S) or (R) configuration, or a racemic mixture. Amino acid units may thus be enantiomerically pure, racemic, or diastereomeric.

Exemplary —$W_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline.

The Amino Acid unit can be enzymatically cleaved by one or more enzymes, including a tumor-associated protease, to liberate the Drug moiety (-D), which in one embodiment is protonated in vivo upon release to provide a Drug (D). Amino acid linker components can be designed and optimized in their selectivity for enzymatic cleavage by a particular enzymes, for example, a tumor-associated protease, cathepsin B, C and D, or a plasmin protease.

Spacer Unit

The Spacer unit (—$Y_y$—), when present (y=1 or 2), links an Amino Acid unit (—$W_w$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y 0). Spacer units are of two general types: self-immolative and non self-immolative. A non self-innmolative Spacer unit is one in which part or all of the Spacer unit remains bound to the Drug moiety after cleavage, particularly enzymatic, of an Amino Acid unit from the antibody-drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-$W_w$—. In one embodiment, an independent hydrolysis reaction takes place within the target cell, cleaving the glycine-Drug moiety bond and liberating the Drug.

In another embodiment, —$Y_y$— is a p-aminobenzylcarbamoyl (PAB) unit whose phenylene portion is substituted with $Q_m$ wherein Q is —$C_1$-$C_8$ alkyl, —O—($C_1$-$C_8$ alkyl), —halogen, -nitro or -cyano; and m is an integer ranging from 0-4.

Exemplary embodiments of a non self-immolative Spacer unit (-Y-) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —Y— is a PAB group that is linked to —$W_w$— via the amino nitrogen atom of the PAB group, and connected directly to -D via a carbonate, carbamate or ether group, where the ADC has the exemplary structure:

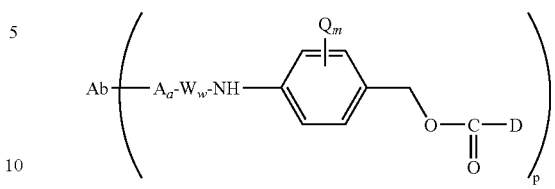

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237), heterocyclic PAB analogs (US 2005/0256030), beta-glucuronide (WO 2007/011968), and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

Exemplary Spacer units (—$Y_y$—) are represented by Formulas X-XII:

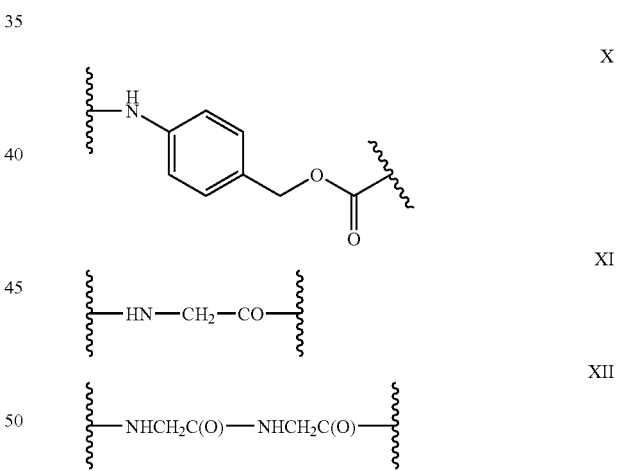

Dendritic Linkers

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11: 1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker. Exemplary embodiments of branched, dendritic linkers include 2,6-bis(hydroxymethyl)-p-cresol and 2,4,6-tris(hydroxymethyl)-phenol dendrimer units (WO 2004/01993; Szalai et al (2003) J. Amer. Chem. Soc. 125:

15688-15689; Shamis et al (2004) J. Amer. Chem. Soc. 126: 1726-1731; Amir et al (2003) Angew. Chem. Int. Ed. 42:4494-4499).

Exemplary embodiments of the Formula I antibody-drug conjugate compounds include XIIIa (MC), XIIIb (val-cit), XIIIc (MC-val-cit), and XIIId (MC-val-cit-PAB):

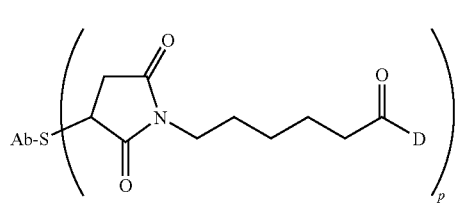

XIIIa

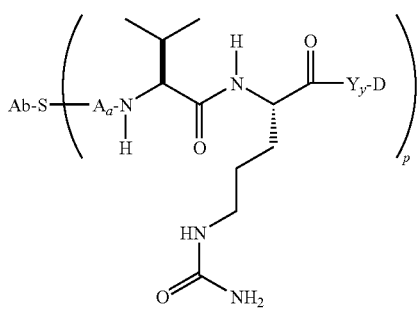

XIIIb

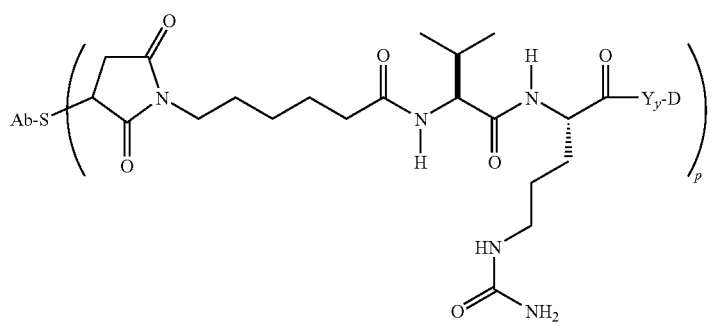

XIIIc

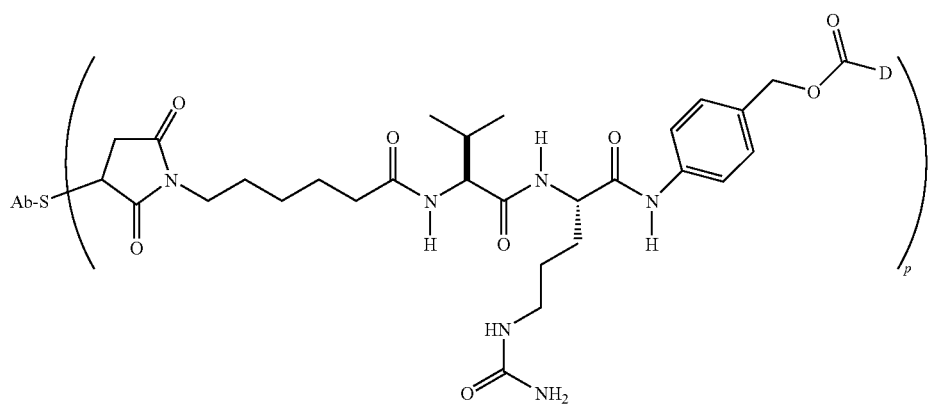

XIIId

In one embodiment, the Spacer unit is a branched bis(hydroxymethyl)styrene (BHMS), which can be used to incorporate and release multiple drugs, having the structure:

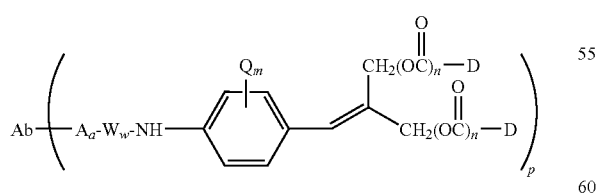

comprising a 2-(4-aminobenzylidene)propane-1,3-diol dendrimer unit (WO 2004/043493; de Groot et al (2003) Angew. Chem. Int. Ed. 42:4490-4494), wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to 4.

Other exemplary embodiments of the Formula Ia antibody-drug conjugate compounds include XIVa-e:

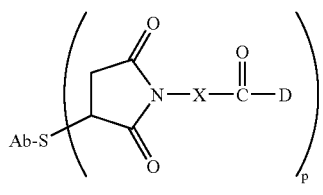

XIVa

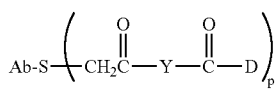

XIVb

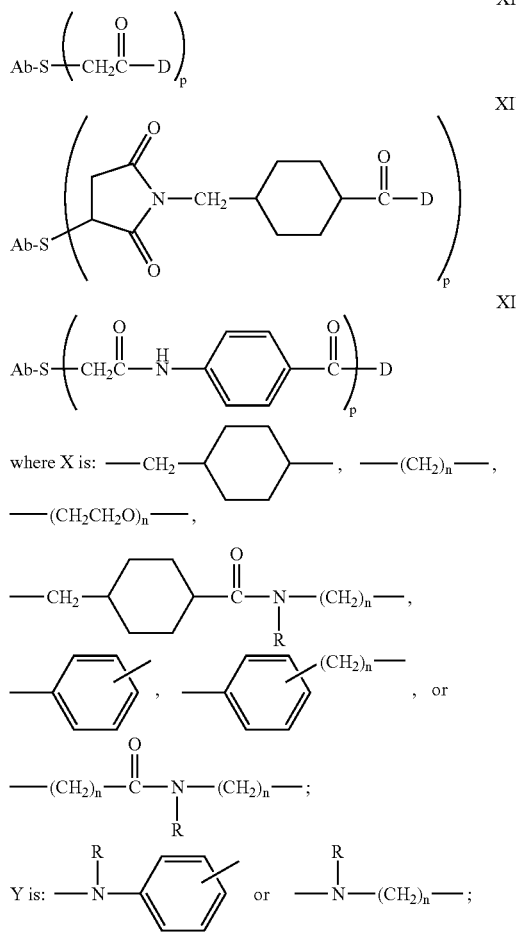

where R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry. Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to carboxyls, hydroxyls, para-nitrophenylcarbonate, isothiocyanate, and leaving groups, such as O-mesyl, O-tosyl, —Cl, —Br, —I; or maleimide.

In another embodiment, the Linker may be substituted with groups which modulated solubility or reactivity. For example, a charged substituent such as sulfonate (—$SO_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

Linker Reagents

Conjugates of the antibody and auristatin may be made using a variety of bifunctional linker reagents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Linker reagents useful for the antibody drug conjugates of the invention include, but are not limited to: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, 1,8-bis-maleimidodiethyleneglycol (BM(PEO)$_2$), and 1,11-bis-maleimidotriethyleneglycol (BM(PEO)$_3$), which are commercially available from Pierce Biotechnology, Inc., ThermoScientific, Rockford, Ill., and other reagent suppliers. Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, nemorubicin metabolite and analog drug moiety, or linker intermediate include iodoacetamide, bromoacetamide, vinyl pyridine, disulfide, pyridyl disulfide, isocyanate, and isothiocyanate.

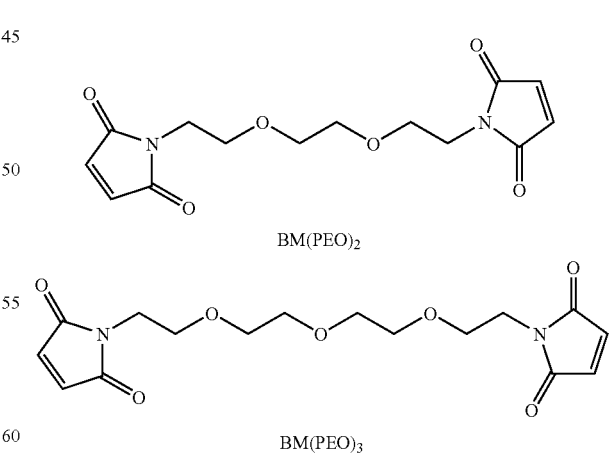

BM(PEO)$_2$

BM(PEO)$_3$

Useful linker reagents can also be obtained via other commercial sources or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No.

6,214,345; WO 02/088172; US 2003130189; US2003096743; WO 03/026577; WO 03/043583; and WO 04/032828.

An exemplary valine-citrulline (val-cit or vc) dipeptide linker reagent having a maleimide Stretcher and a para-aminobenzylcarbamoyl (PAB) self-immolative Spacer has the structure:

An exemplary phe-lys(Mtr, mono-4-methoxytrityl)dipeptide linker reagent having a maleimide Stretcher unit and a PAB self-immolative Spacer unit can be prepared according to Dubowchik, et al. (1997) Tetrahedron Letters, 38:5257-60, and has the structure:

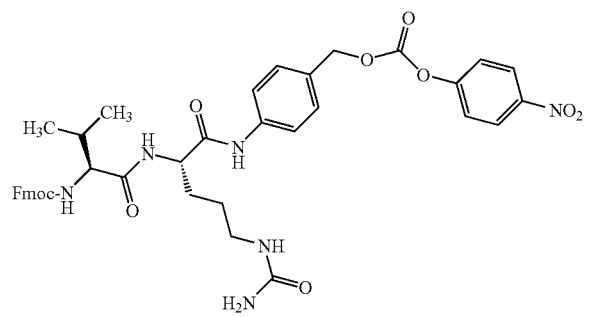

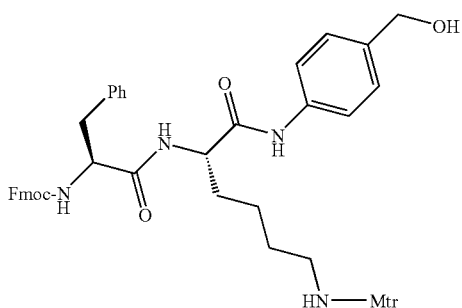

Exemplary drug-linker intermediates include:

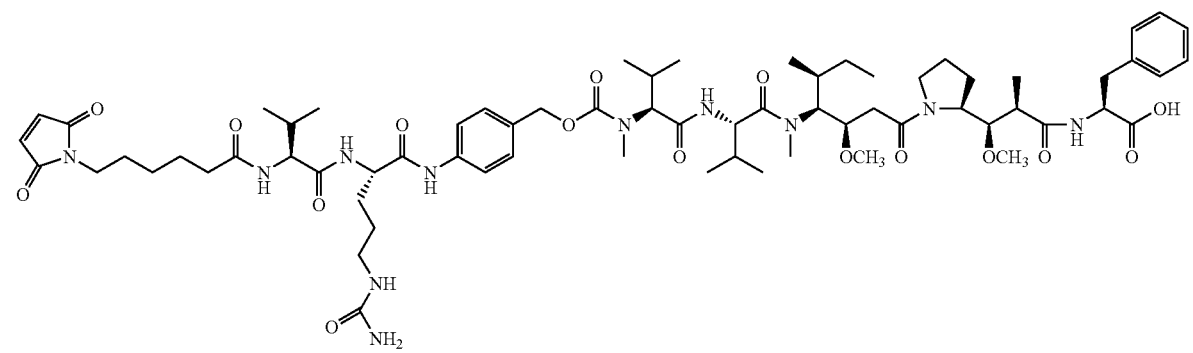

MC-val-cit-PAB-MMAF

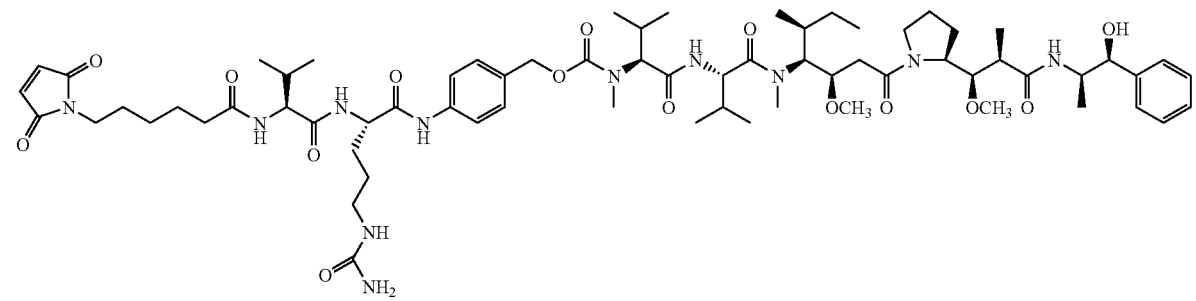

MC-val-cit-PAB-MMAE

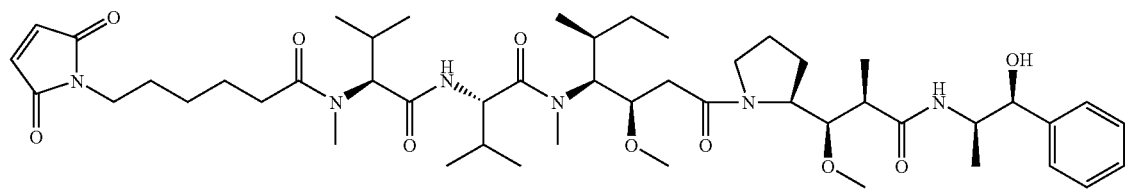

MC-MMAE

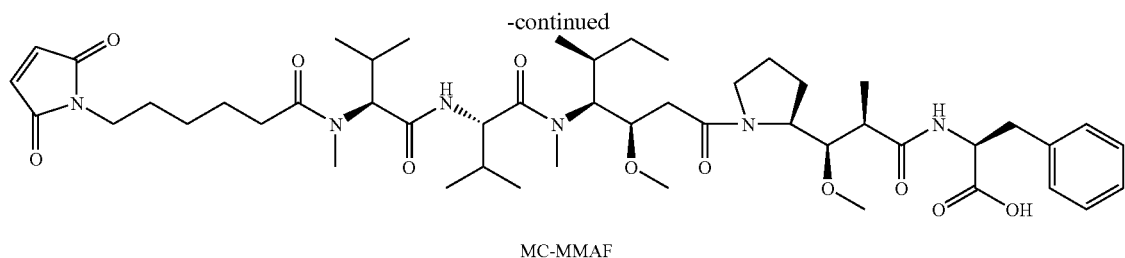
MC-MMAF
Exemplary antibody-drug conjugate compounds of the invention include:
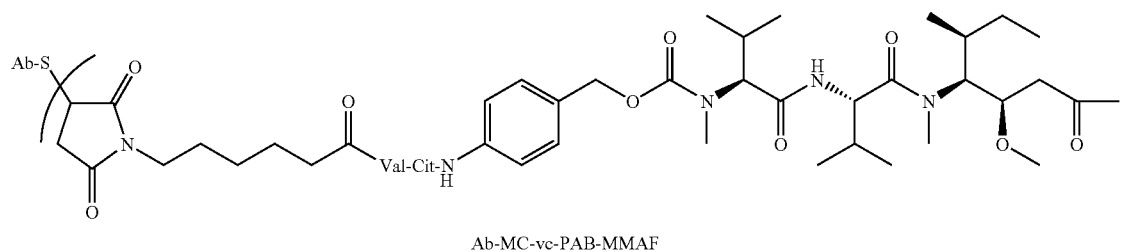
Ab-MC-vc-PAB-MMAF
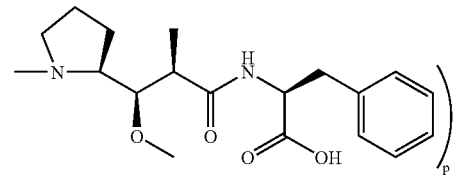
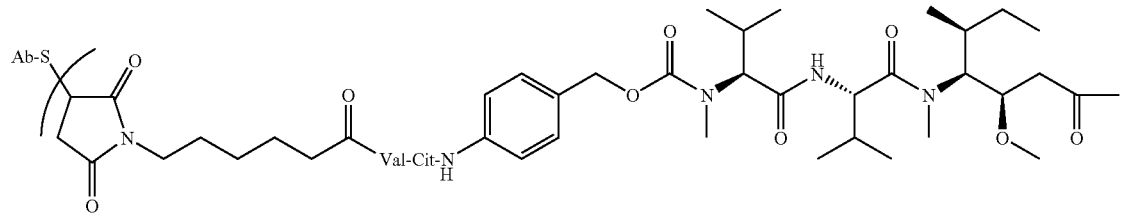
Ab-MC-vc-PAB-MMAE
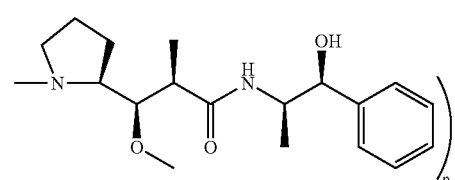
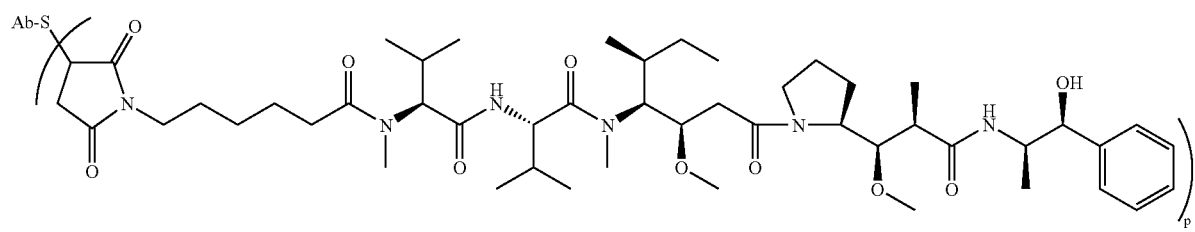
Ab-MC-MMAE

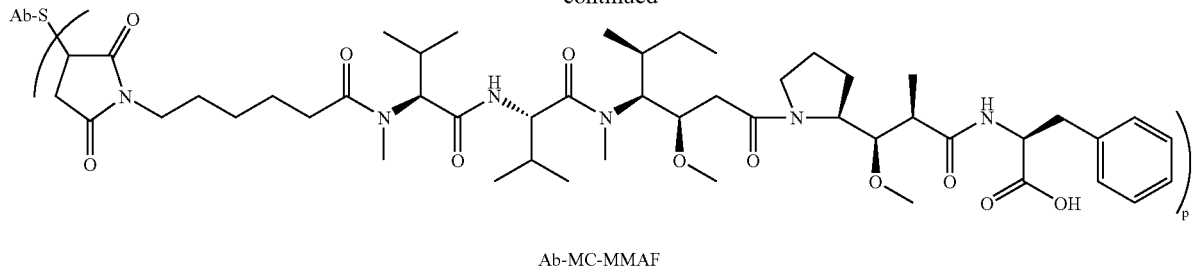

Ab-MC-MMAF where Val is valine; Cit is citrulline; p is 1, 2, 3, or 4; and Ab is a cysteine engineered anti-MUC16 antibody.

Preparation of Cysteine Engineered Anti-MUC16 Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.), followed by reoxidation to reform interchain and intrachain disulfide bonds (Example 2). For example, full length, cysteine engineered monoclonal antibodies (ThioMabs) expressed in CHO cells are reduced with about a 50 fold excess of TCEP for 3 hrs at 37° C. to reduce disulfide bonds in cysteine and glutathione adducts which may form between the newly introduced cysteine residues and the cysteine present in the culture media. This partial reduction which disrupts inter-chain disulfide bonds but not intra-chain disulfide bonds may be followed by diafiltration. The reduced ThioMab is diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate (CuSO$_4$) at room temperature, overnight. Alternatively, dehydroascorbic acid (DHAA) is an effective oxidant to reestablish the intrachain disulfide groups of the cysteine engineered antibody after reductive cleavage of the cysteine adducts, as demonstrated by SDS-PAGE analysis. Other oxidants, i.e. oxidizing agents, and oxidizing conditions, which are known in the art may be used. Ambient air oxidation is also effective. This mild, partial reoxidation step forms intrachain disulfides efficiently with high fidelity and preserves the thiol groups of the newly introduced cysteine residues. An approximate 3 fold excess of drug-linker intermediate, e.g. MC-vc-PAB-MMAE, relative to antibody (about 1.5 fold excess relative to newly introduced cysteine residues) was added, mixed, and let stand for about an hour at room temperature to effect conjugation and form the 3A5 anti-MUC16 antibody-drug conjugate. The conjugation mixture was gel filtered and loaded and eluted through a HiTrap S column to remove excess drug-linker intermediate and other impurities.

Figure 6A:
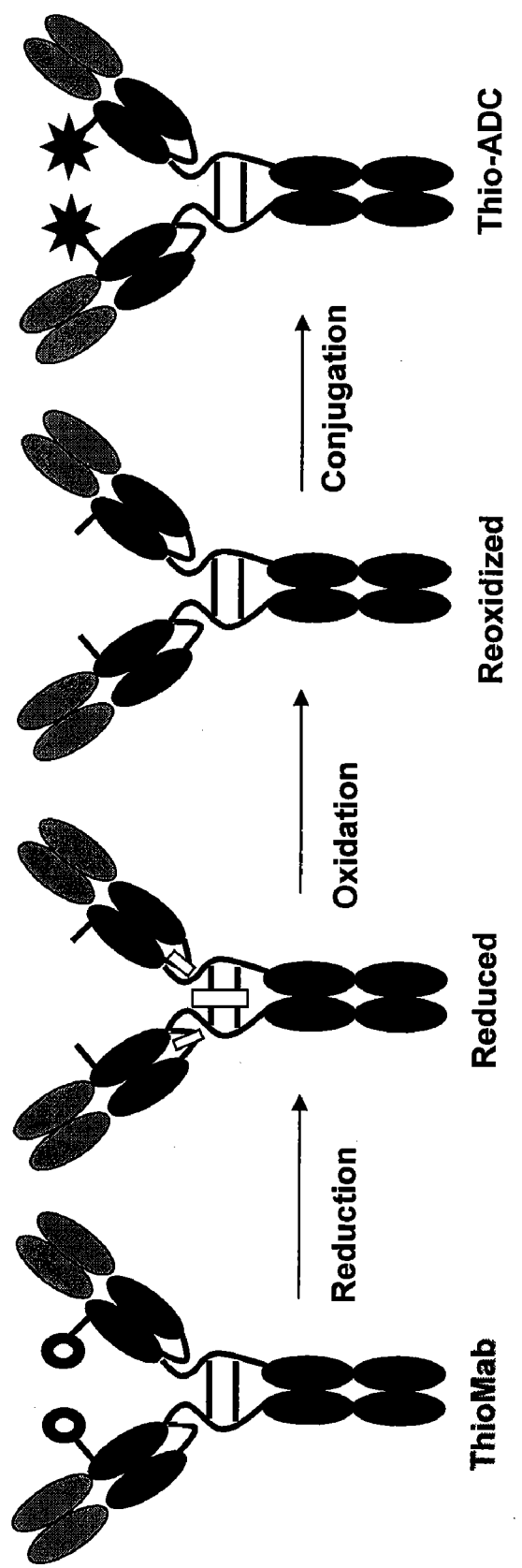
FIG. 6a shows the steps of: (i) reducing cysteine disulfide adducts and interchain and intrachain disulfides in a cysteine engineered anti-MUC16 antibody (ThioMab); (ii) partially oxidizing, i.e. reoxidation to reform interchain and intrachain disulfides; and (iii) conjugation of the reoxidized antibody with a drug-linker intermediate to form a cysteine engineered anti-MUC16 antibody drug conjugate (ADC).

FIG. 6a shows the general process to prepare a cysteine engineered antibody expressed from cell culture for conjugation. When the cell culture media contains cysteine, disulfide adducts can form between the newly introduced cysteine amino acid and cysteine or glutathione from media. Cysteine adducts, depicted as a circle in the exemplary ThioMab (left) in FIG. 6a, must be reduced to generate cysteine engineered antibodies reactive for conjugation. Cysteine adducts, presumably along with various interchain disulfide bonds, are reductively cleaved to give a reduced form of the antibody with reducing agents such as TCEP. The interchain disulfide bonds between paired cysteine residues are reformed under partial oxidation conditions with copper sulfate, DHAA, or exposure to ambient oxygen. The newly introduced, engineered, and unpaired cysteine residues remain available for reaction with linker reagents or drug-linker intermediates to form the antibody conjugates of the invention. The ThioMabs expressed in mammalian cell lines result in externally conjugated Cys adduct to an engineered Cys through —S—S— bond formation. Hence the purified ThioMabs are treated with the reduction and reoxidation procedures as described in Example 2 to produce reactive ThioMabs. These ThioMabs are used to conjugate with maleimide containing cytotoxic drugs, fluorophores, and other labels.

Figure 6B:
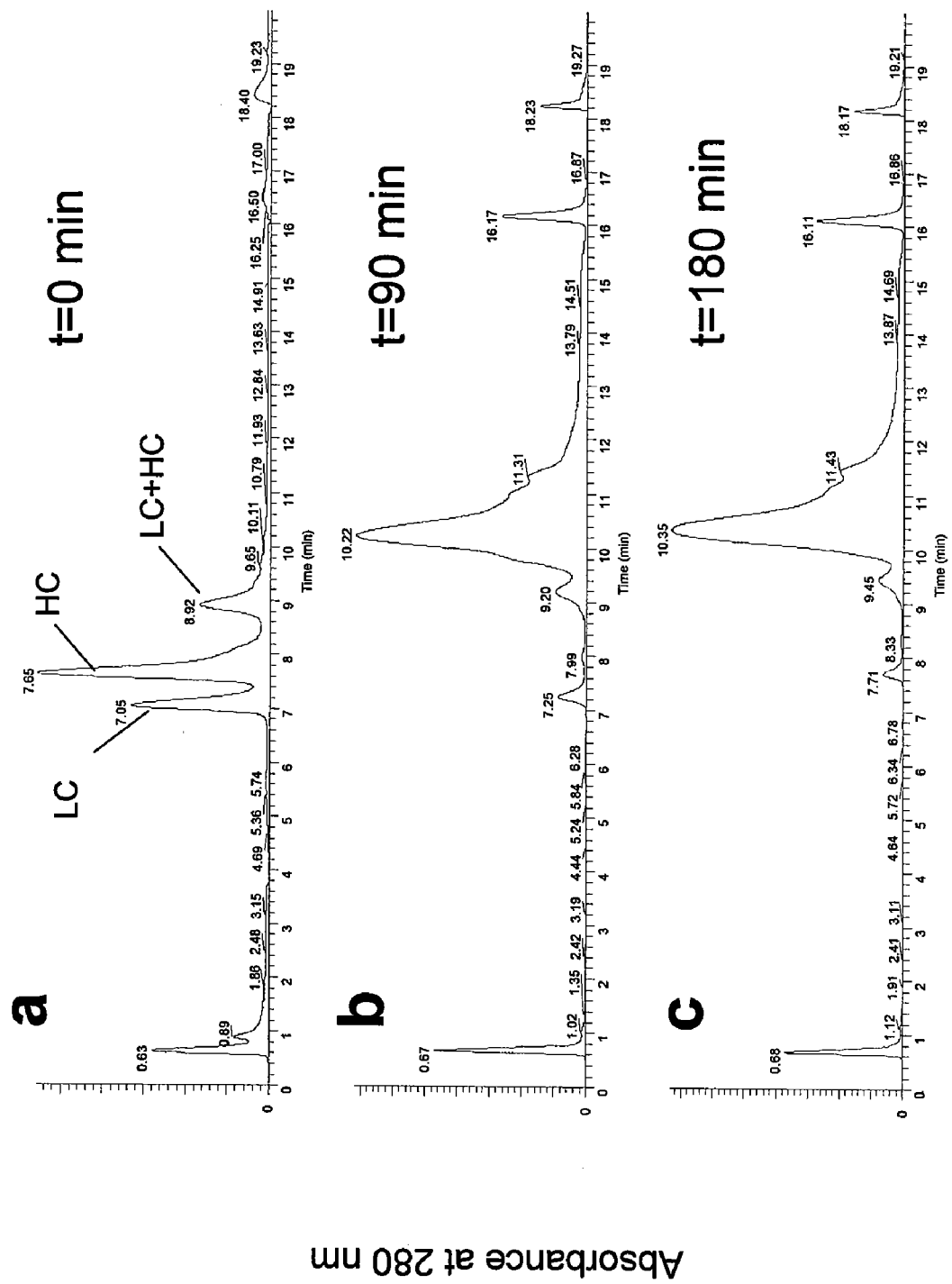
FIG. 6b shows the time course for re-oxidation for reduced antibody. Trastuzumab was reduced and purified on a cation exchange column at pH 5.5. Top panel a shows the reversed phase profile for the reduced antibody at time=0 min. The three peaks at retention time 7 minutes (from left to right) are: light chain (LC), heavy chain (HC) and a small amount of HC+LC that was not completely reduced. The purified, reduced antibody was allowed to re-oxidize at pH 7, and aliquots were taken as a function of time. Middle panel b shows that the majority of light and heavy chains have re-oxidized to form an intact antibody (~retention time 10 min peak) containing 2 LC and 2 HC within 90 min. No additional formation of intact antibody was seen at the 180 min reaction time point (bottom panel c).

FIG. 6b shows the time course for re-oxidation for reduced antibody. Trastuzumab was reduced and purified on a cation exchange column at pH 5.5. Top panel a shows the reversed phase profile for the reduced antibody at time=0 min. The three peaks at retention time 7 minutes (from left to right) are: light chain (LC), heavy chain (HC) and a small amount of HC+LC that was not completely reduced. The purified, reduced antibody was allowed to re-oxidize at pH 7, and aliquots were taken as a function of time. Middle panel b shows that the majority of light and heavy chains have re-oxidized to form an intact antibody (~retention time 10 min peak) containing 2 LC and 2 HC within 90 min. No additional formation of intact antibody was seen at the 180 min reaction time point (bottom panel c).

Figure 7A:
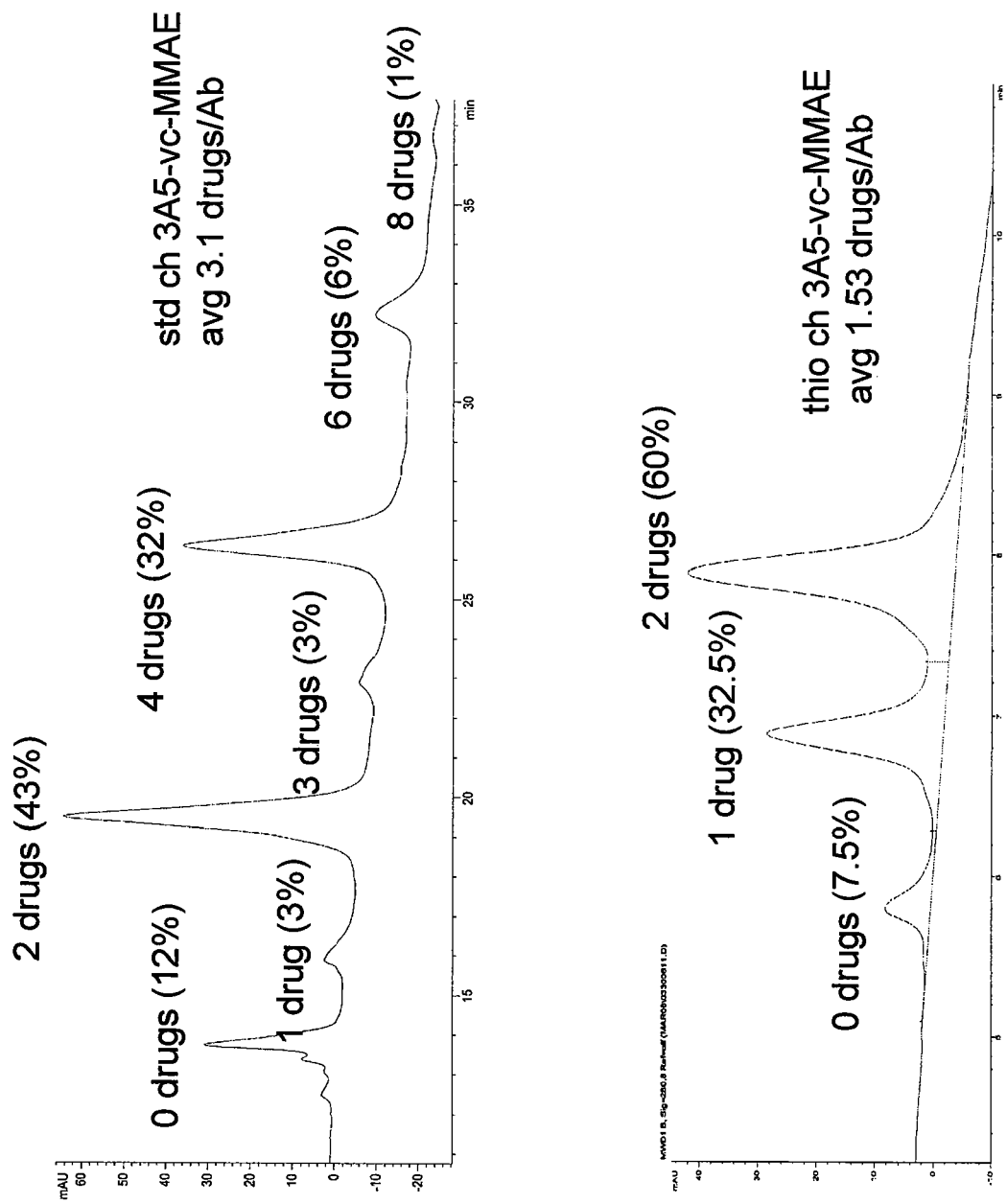
FIG. 7a shows two HIC (hydrophobic interaction chromatography) chromatograms of conjugation reaction products: (top) std ch 3A5-MC-vc-PAB-MMAE, 3.1 avg. MMAE/3A5; and (bottom) thio ch 3A5-MC-vc-PAB-MMAE, 1.5 avg. MMAE/3A5, where std ch 3A5 is the parent chimeric anti-MUC16 antibody called 3A5, and thio ch 3A5 is the cysteine engineered chimeric anti-MUC16 3A5 antibody. Samples were injected onto a Butyl HIC NPR column and eluted with linear gradient from 0 to 70% B at 0.8 ml/min (Buffer A: 1.5 M ammonium sulfate in 50 mM potassium phoshate, pH 7, Buffer B: 50 mM potassium phosphate pH 7, 20% isopropanol). An Agilent 1100 series HPLC system equipped with a multi wavelength detector and Chemstation software was used to resolve and quantitate antibody species in the antibody. Peak identities were assigned based on LC/MS analysis. DAR values are indicated for the corresponding peaks.
Figure 7B:
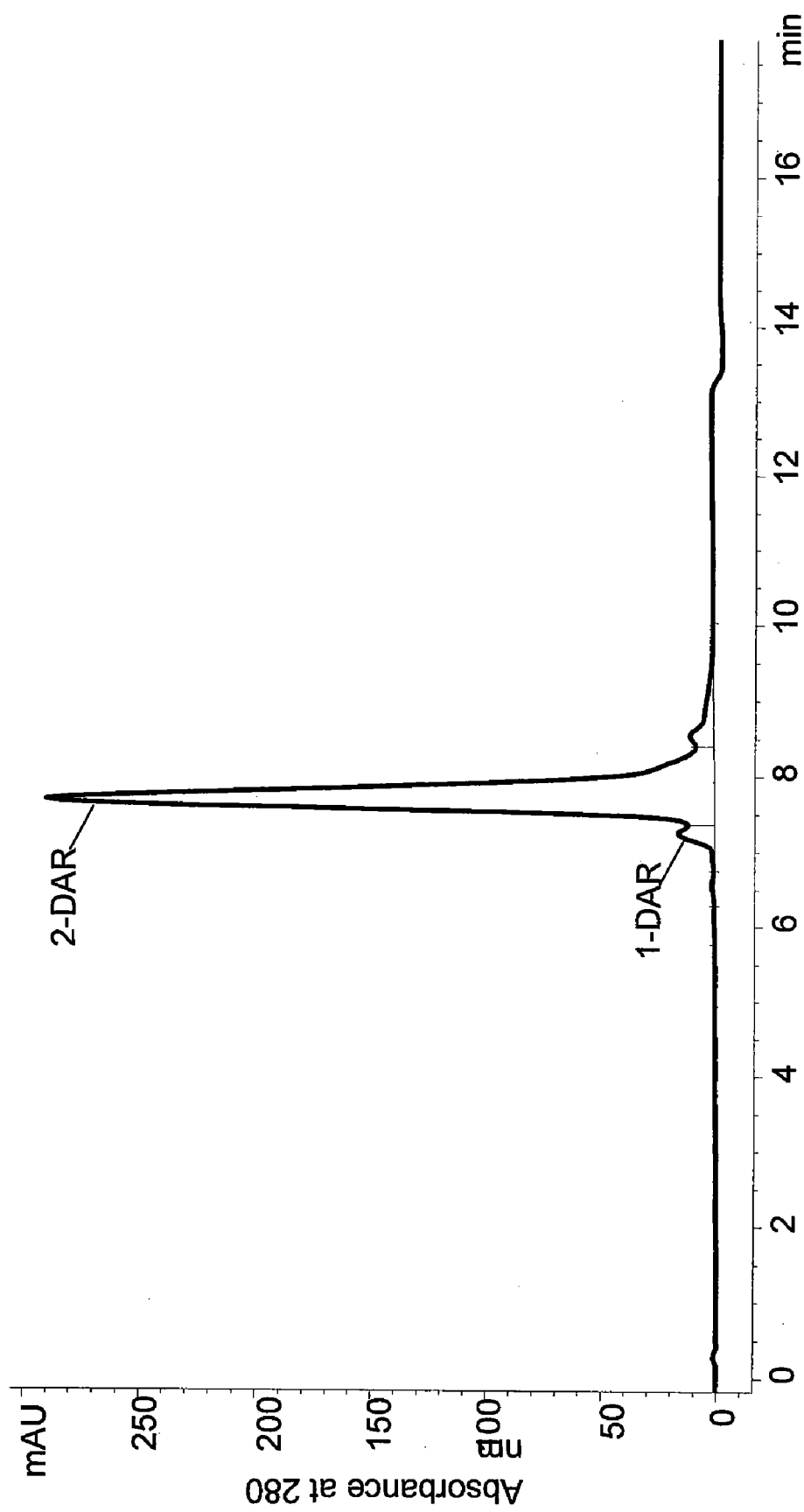
FIG. 7b shows HIC (hydrophobic interaction chromatography) chromatogram under the conditions of the analyses in FIG. 7a of a larger scale thio ch 3A5-MC-vc-PAB-MMAE conjugation reaction, where the average drug loading value was 1.9.

Analysis of cysteine engineered antibody drug conjugate reactions show decreased heterogeneity relative to antibody drug conjugates prepared by reduction of interchain or intrachain disulfide bonds followed by conjugation (standard ADC) with a thiol reactive drug linker intermediate. FIG. 7a shows HIC (hydrophobic interaction chromatography) analysis of the conjugation product of standard chimeric 3A5 with MC-vc-PAB-MMAE (top). The HIC analysis separates ADC on the basis of drugs per antibody. A distribution of groups of ADC with varying drugs per antibody results, with ADC bearing 0 (12%), 1 (3%), 2 (43%), 3 (3%), 4 (32%), 6 (6%) and 8 (1%) MMAE per 3A5 antibody. Within each group, there is presumed additional heterogeneity with MMAE linked to 3A5 at any of the eight interchain disulfide bonds. Some of these species are detectable by mass spectroscopy but are not resolved by HIC chromatography. In comparison, FIG. 7a also shows HIC analysis of the conjugation product of cysteine engineered chimeric 3A5 with MC-vc-PAB-MMAE (bottom). A less hetereogeneous distribution of products (mixture of ADC) and a lower average drug loading value (p, average drugs/Ab) results. The product mixture is predominantly a single species, 2 MMAE per 3A5 (60%), where the drug is attached at each of the A117C cysteine mutation sites in the heavy chain. Incomplete reaction results in about 32% of one MMAE per antibody and 7% of unconjugated antibody. Higher loaded ADCs are not detectable. FIG. 7b shows HIC (hydrophobic interaction chromatography) chromatogram under the conditions of the analyses in FIG. 7a of a larger scale thio ch 3A5-MC-vc-PAB-MMAE conjugation reaction, where the average drug loading value was 1.9 MMAE per thio ch 3A5.

Figure 8A:
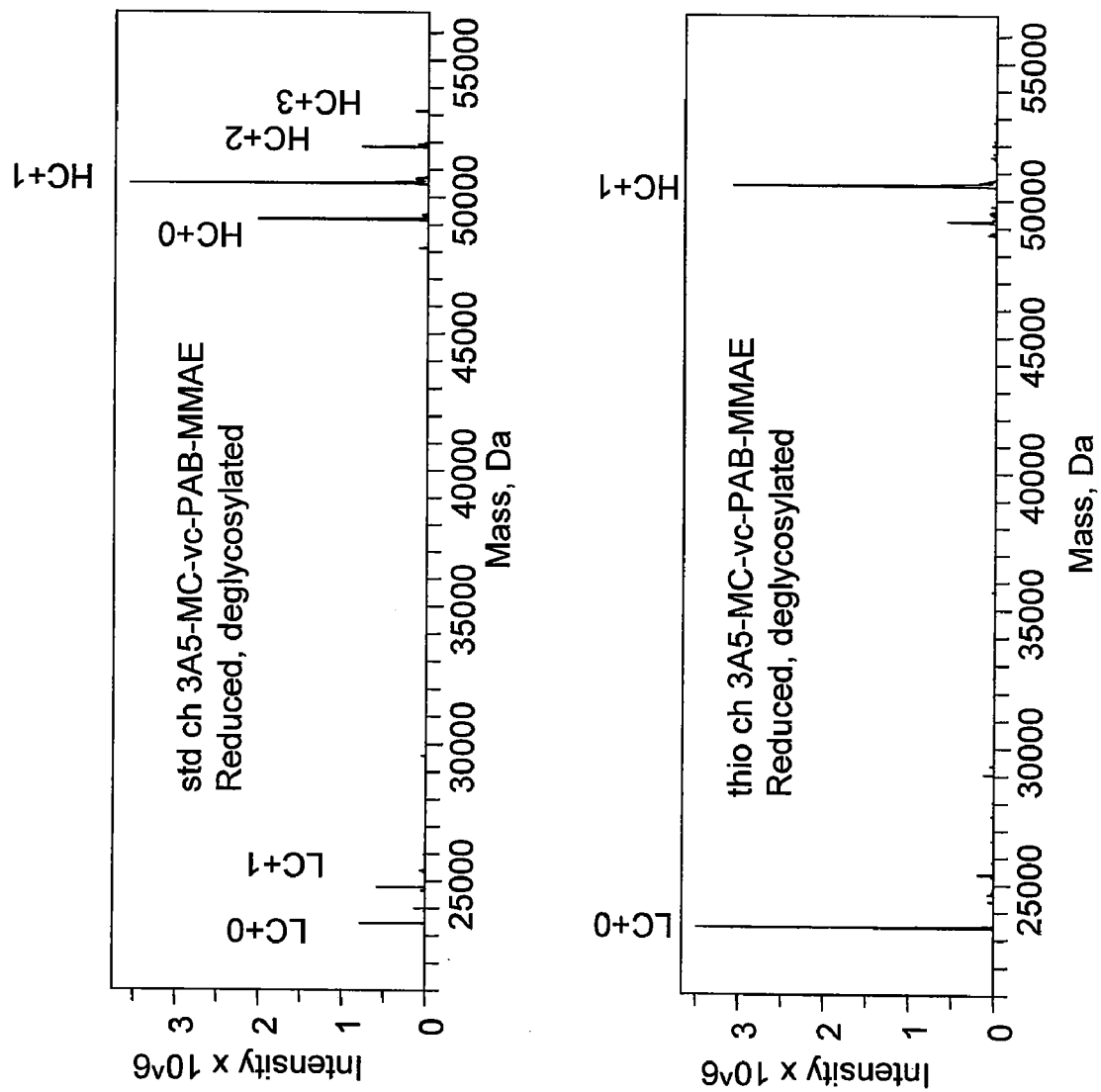
FIG. 8a shows mass spectroscopy analysis of conjugation reaction products after reduction and deglycosylation: (top) std ch 3A5-MC-vc-PAB-MMAE; and (bottom) thio ch 3A5-MC-vc-PAB-MMAE.

FIG. 8a shows mass spectroscopy analysis of the conjugation product of standard (parent) chimeric 3A5 with MC-vc-PAB-MMAE, after reduction and deglycosylation, shows the relative amounts of drug bound to the heavy (HC) and light (LC) chains (top). About half of the light chains were conjugated with one drug. The heavy chains had a distribution of 0, 1, 2, and 3 drugs. Within each detectable mass, there is presumed additional heterogeneity with MMAE linked to 3A5 at any of the interchain disulfide bonds. In comparison, FIG. 8a also shows mass spectroscopy analysis of the conjugation product of cysteine engineered chimeric 3A5 with MC-vc-PAB-MMAE (bottom). As expected, the light chains do not bear MMAE. The majority of heavy chain is conjugated with one MMAE, through the A117C cysteine mutation site as described in FIGS. 8b and 8c. The standard and thio ADC were deglycosylated and reduced prior to LC/MS analysis. Deconvoluted mass spectra of standard ADC (top, FIG. 8a) displayed zero or one drug species on the light chain and zero, one, two, or three drug species on the heavy chain, whereas thio ADC displayed only one drug species on the heavy chain, indicating more homogeneity of the thio ADC as expected.

Figure 8B:
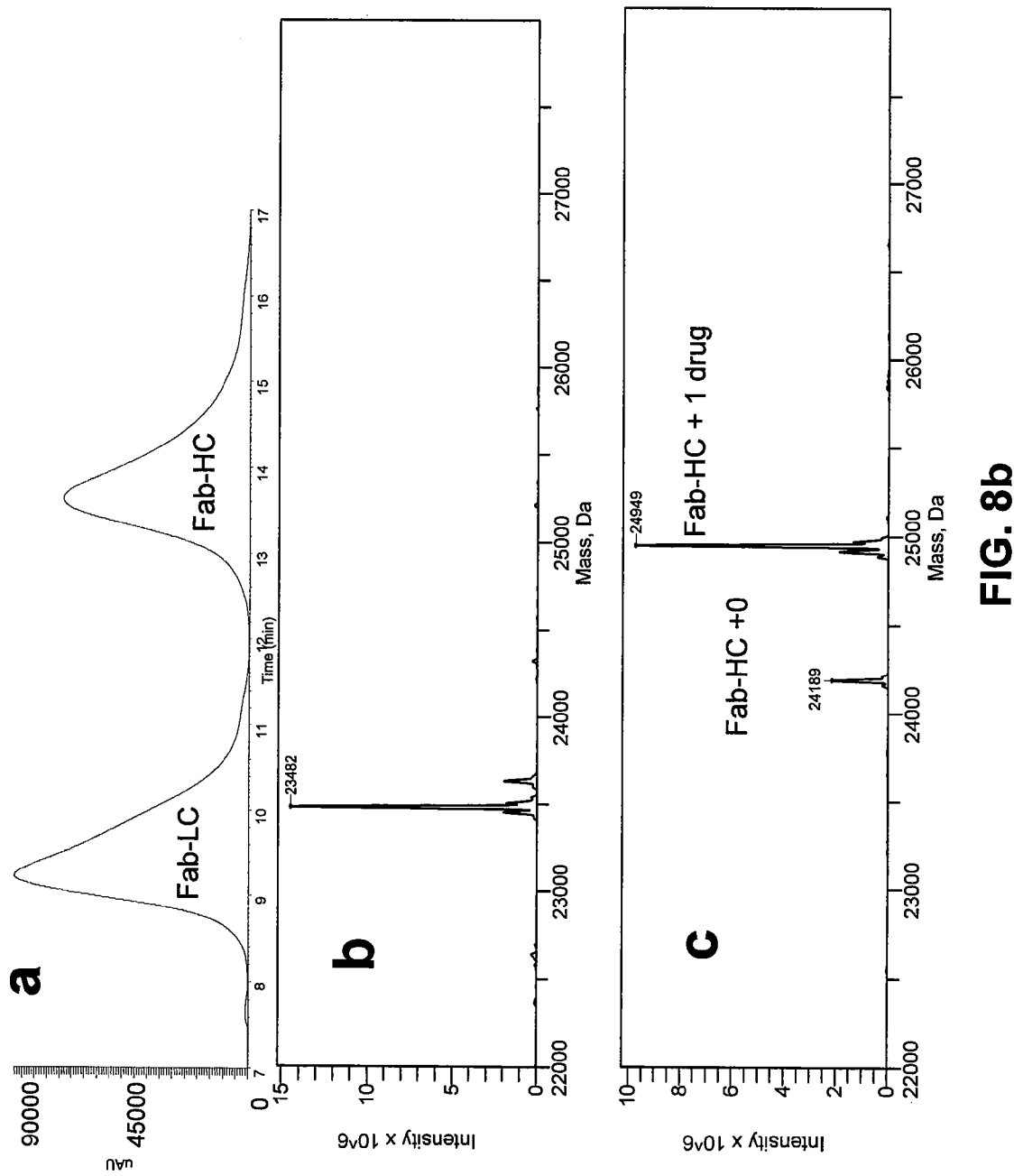
FIG. 8b shows mapping of the antibody region for cytotoxic drug attachment to the TDC-Fab. Top panel (a) shows a 280 nm absorbance spectrum of reduced, denatured light and heavy chain portions of the MC-vc-PAB-MMAE-conjugated Fab. Deconvoluted masses of light chain in the middle panel (b) and heavy chain in the lower panel (c) portions are consistent with drug labeling on the heavy chain only. The mass of 24189 observed in (c) results from the loss of MMAE-CO2 (minus 762 daltons) which is a characteristic fragmentation of the drug.

FIG. 8b shows mapping of the antibody region for cytotoxic drug attachment to the TDC-Fab. Top panel (a) shows a 280 nm absorbance spectrum of reduced, denatured light and heavy chain portions of the MC-vc-PAB-MMAE-conjugated Fab. Deconvoluted masses of light chain in the middle panel (b) and heavy chain in the lower panel (c) portions are consistent with drug labeling on the heavy chain only. The mass of 24189 observed in (c) results from the loss of MMAE-CO2 (minus 762 daltons) which is a characteristic fragmentation of the drug.

FIG. 8c shows peptide mapping—identification of peptide(s) containing cytotoxic drug in the TDC-Fab. Peptide maps of unconjugated (top panel a) and conjugated (middle panel b) Thio-3A5 and TDC generated from tryptic digests of maleimidylated purified Fabs. Peptides labeled with MC-vc-PAB-MMAE have increased hydrophobicity and are expected to elute later in the chromatogram. Four drug-conjugated peptides (labeled with *) eluted at the end of the gradient. They can also be identified as cytotoxic drug containing peptides by a characteristic in-source fragmentation ion (m/z 718.5) that is observed in all MC-vc-PAB-MMAE containing mass spectra. Bottom panel (c) shows an overlay of the extracted ion chromatogram from the unconjugated and the conjugated digests. The strongest peaks coincide with the late eluting peaks of the conjugate digest. All four peaks were identified as complete or partial tryptic cleavage fragments located around the mutated cysteine in position 114 of the Fab-HC. The m/z ions in the main peak at 29.05 min deconvoluted to give a mass of 3962 daltons, which is the expected mass for peptide HC99-120+1 drug. The drug-containing peptide masses did not map to any other region of the protein. The peak labeled with an arrow in top panel (a) is the maleimide labeled peptide HC99-120.

The standard and thio (cysteine engineered) ADC were also analyzed by SDS-PAGE under non-reducing and reducing conditions. The standard ADC showed multiple species due to loss of interchain disulfide bonds as depicted in FIG. 9a.

FIG. 9b compares the major species detected by tandem liquid chromatography and mass spectrometry (LC-MS) of the standard Hu3A5-VC-MMAE and two preparations ThioHu3A5-VC-MMAE. Before chromatographic analysis, the samples were either treated with DTT to reductively cleave disulfide bonds or left intact. The Hu3A5-VC-MMAE prepared with conventional methods yields a broad distribution of species, reflecting the heterogeneity of the conjugation process and the loss of inter-chain disulfide bonds. In contrast, both preparations of ThioHu3A5-VC-MMAE are much more nearly homogenous, and the detected species represent either intact non-conjugated antibody (bearing all normal disulfide bonds) or antibody conjugated with linker-drug at the engineered cysteines and nowhere else.

Methods of Screening

Yet another embodiment of the present invention is directed to a method of determining the presence of a MUC16/CA125/O772P polypeptide in a sample suspected of containing the MUC16/CA125/O772P polypeptide, wherein the method comprises exposing the sample to a cysteine engineered anti-MUC16 antibody, or antibody drug conjugate thereof, that binds to the MUC16/CA125/O772P polypeptide and determining binding of the cysteine engineered anti-MUC16 antibody, or antibody drug conjugate thereof, to the MUC16/CA125/O772P polypeptide in the sample, wherein the presence of such binding is indicative of the presence of the MUC16/CA125/O772P polypeptide in the sample. Optionally, the sample may contain cells (which may be cancer cells) suspected of expressing the MUC16/CA125/O772P polypeptide. The cysteine engineered anti-MUC16 antibody, or antibody drug conjugate thereof, employed in the method may optionally be detectably labeled, attached to a solid support, or the like.

Another embodiment of the present invention is directed to a method of diagnosing the presence of a tumor in a mammal, wherein the method comprises (a) contacting a test sample comprising tissue cells obtained from the mammal with a cysteine engineered anti-MUC16 antibody, or antibody drug conjugate thereof, that binds to a CA125/O772P polypeptide and (b) detecting the formation of a complex between the cysteine engineered anti-MUC16 antibody, or antibody drug conjugate thereof, and the CA125/O772P polypeptide in the test sample, wherein the formation of a complex is indicative of the presence of a tumor in the mammal. Optionally, the cysteine engineered anti-MUC16 antibody, or antibody drug conjugate thereof, is detectably labeled, attached to a solid support, or the like, and/or the test sample of tissue cells is obtained from an individual suspected of having a cancerous tumor.

In Vitro Cell Proliferation Assays

One embodiment of the present invention is directed to a method for inhibiting the growth of a cell that expresses a MUC16 polypeptide, wherein the method comprises contacting the cell with a cysteine engineered anti-MUC16 antibody, or antibody drug conjugate thereof, to the MUC16 polypeptide causes inhibition of the growth of the cell expressing the MUC16. The cell may be a cancer cell and binding of the cysteine engineered antibody, or antibody drug conjugate thereof, to the MUC16 polypeptide causes death or inhibits proliferation of the cell expressing the MUC16 polypeptide.

Generally, the cytotoxic or cytostatic activity of an antibody-drug conjugate (ADC) is measured by: exposing mammalian cells expressing MUC16 polypeptide to ADC in a cell culture medium; culturing the cells for a period from about 6 hours to about 5 days; and measuring cell viability. Mammalian cells useful for cell proliferation assays include: (1) a MUC16 polypeptide-expressing cell line OVCAR-3; (2) a PC3-derived cell line engineered to stably express a portion of the MUC16 polypeptide on its cell surface (PC3/MUC16); (3) the parental PC3 cell line that does not express the MUC16 polypeptide; and (4) a PC3 cell line that does not express MUC16 polypeptide but carries the vector used to drive exogenous MUC16 expression (PC3/neo). Cell-based in vitro assays are used to measure viability (proliferation), cytotoxicity, and induction of apoptosis (caspase activation) of the ADC of the invention.

Figure 10:
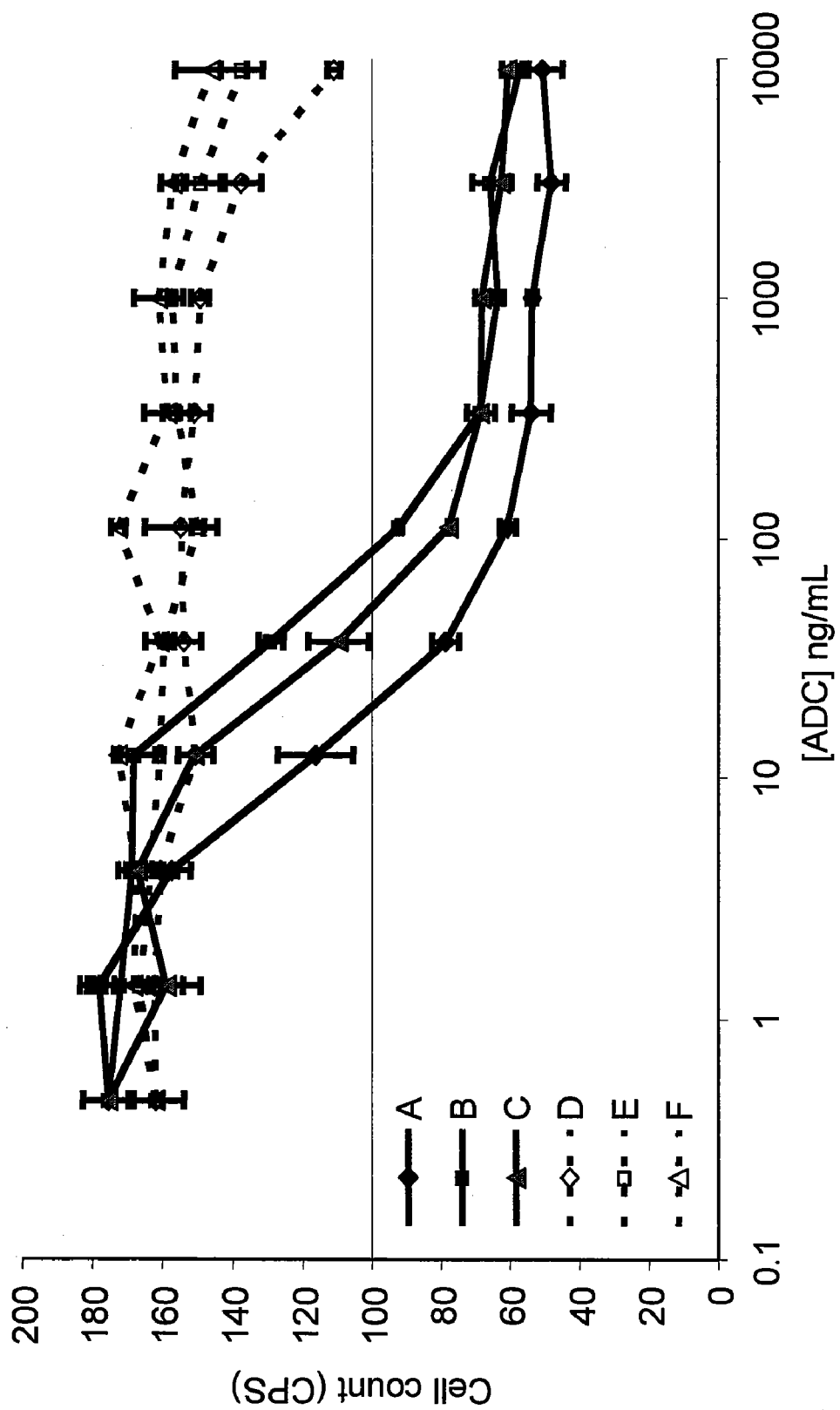
FIG. 10 shows a plot of in vitro, cell proliferation assay results with MUC16 expressing (PC3/MUC16) and non-expressing (PC3 parent) tumor cells, treated with varying concentrations 0.1 to 10000 ng of ADC per ml, including: (A) std hu 3A5(v4b.52)-MC-vc-PAB-MMAE, 3.5 MMAE/Ab loading, PC3/MUC16; (B) thio hu 3A5-MC-vc-PAB-MMAE, 1.9 MMAE/Ab loading, PC3/MUC16; (C) thio hu 3A5-MC-vc-PAB-MMAE, 1.60 MMAE/Ab loading, PC3/MUC16; (D) std hu 3A5(v4b.52)-MC-vc-PAB-MMAE, 3.5 MMAE/Ab loading, PC3 parent; (E) thio hu 3A5-MC-vc-PAB-MMAE, 1.9 MMAE/Ab loading, PC3 parent; and (F) thio hu 3A5-MC-vc-PAB-MMAE, 1.60 MMAE/Ab loading, PC3 parent. Data from cells receiving medium without ADC are plotted at 0.46 ng/mL. Std ch 3A5 is the parent chimeric anti-MUC16 antibody called 3A5, and thio ch 3A5 is the cysteine engineered chimeric anti-MUC16 3A5 antibody.
Figure 11:
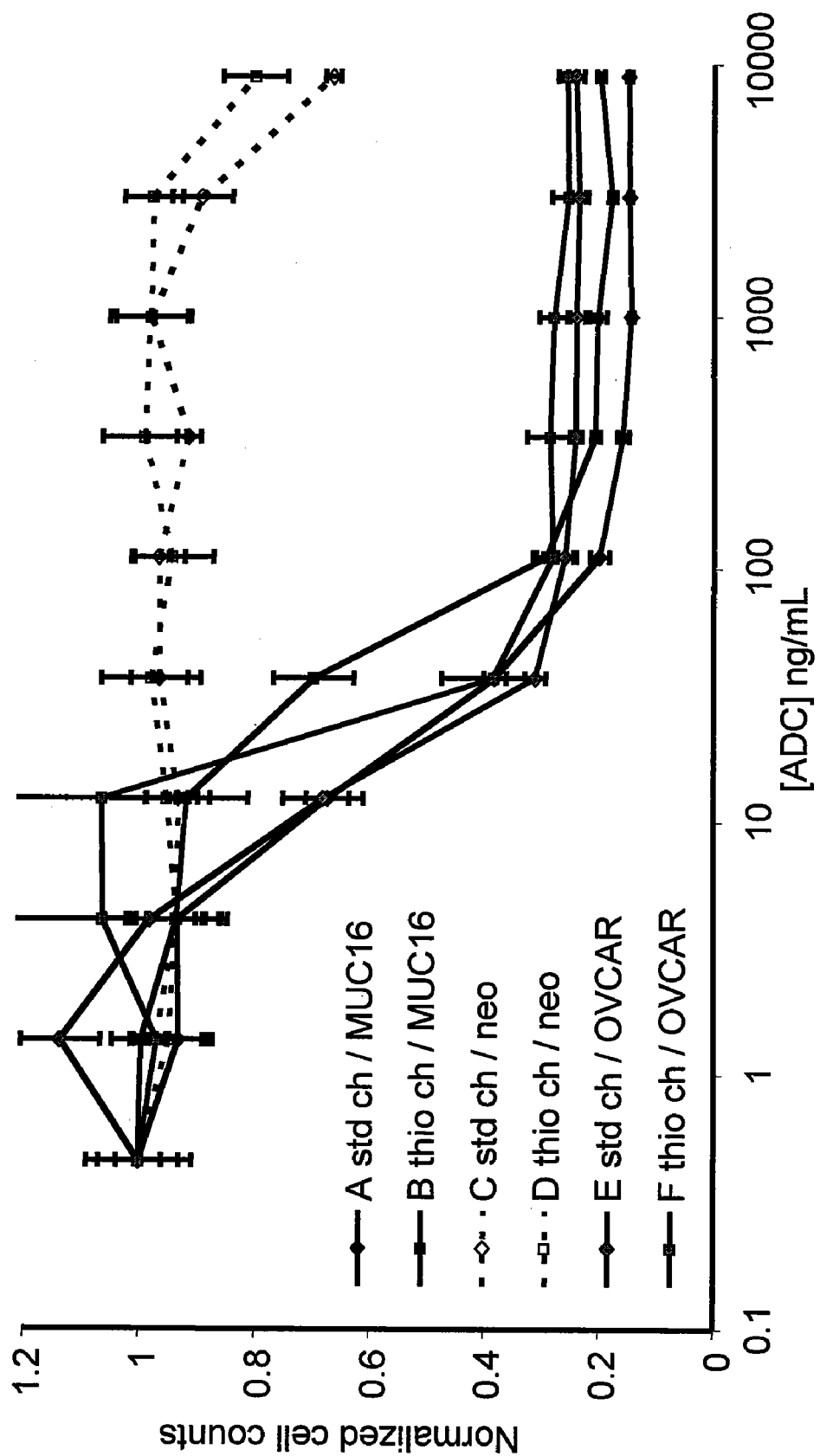
FIG. 11 shows a plot of in vitro, cell proliferation assay results with tumor cells including, treated with varying concentrations 1.4 to 9000 ng of ADC per ml, including: (A) std ch 3A5-MC-vc-PAB-MMAE, 3.1 MMAE/Ab loading, PC3/MUC16 cells; (B) thio ch 3A5-MC-vc-PAB-MMAE, 1.6 MMAE/Ab loading, PC3/MUC16 cells (C) std ch 3A5-MC-vc-PAB-MMAE, 3.1 MMAE/Ab loading, PC3/neo cells; (D) thio ch 3A5-MC-vc-PAB-MMAE, 1.6 MMAE/Ab loading, PC3/neo cells (E) std ch 3A5-MC-vc-PAB-MMAE, 3.1 MMAE/Ab loading, OVCAR-3 cells; (F) thio ch 3A5-MC-vc-PAB-MMAE, 1.6 MMAE/Ab loading, OVCAR-3 cells. Std ch 3A5 is the parent chimeric anti-MUC16 antibody called 3A5, and thio ch 3A5 is the cysteine engineered chimeric anti-MUC16 3A5 antibody. Data from cells receiving medium without ADC are plotted at 0.46 ng/mL.

The in vitro potency of antibody-drug conjugates was measured by a cell proliferation assay (FIGS. 10 and 11, Example 4). The CellTiter-Glo® Luminescent Cell Viability Assay is a commercially available (Promega Corp., Madison, Wis.), homogeneous assay method (Mendoza et al (2002) Cancer Res. 62:5485-5488) based on the recombinant expression of *Coleoptera luciferase* (U.S. Pat. No. 5,583,024; U.S. Pat. No. 5,674,713; U.S. Pat. No. 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677).

Results from the in vitro cell proliferation assays are shown in FIGS. 10 and 11 and demonstrate that each of the cysteine engineered anti-MUC16 antibody drug conjugates caused significant levels of cell death in the OVCAR-3 and PC3/MUC16 cells (i.e., cells that express MUC16 polypeptide on the cell surface), whereas no significant cell killing was observed for any of the antibodies in the parental PC3 and PC3/neo cells (which do not express MUC16 polypeptide on the cell surface). These data demonstrate the tested conjugates are capable of binding to the MUC16 polypeptide expressed on the surface of cells and causing the death of those cells in vitro.

Pharmacokinetics—Serum Clearance and Stability

The disposition of the anti-MUC16 antibody-drug conjugates in vivo was analyzed by measuring the serum concentrations of antibody and of drug conjugate after a single intravenous bolus dose into Sprague-Dawley rats. Concentrations of antibody-drug conjugates bearing at least one cytotoxic drug were measured with an ELISA that used a MUC16 extracellular domain (ECD) protein for the capture and anti-MMAE and horseradish peroxidase (HRP) conjugated anti-mouse Fc antibody for detection. Total Ch3A5 and ThioCh3A5 concentrations in serum were measured with an ELISA that used MUC16 ECD for capture and anti-human-Fc HRP for detection. This assay measured any anti-MUC16 antibody, both with and without conjugated MMAE. The assays have lower limits of quantitation of 0.78 ng/mL with a minimum dilution of 1:10. The assays have lower limits of quantitation of 0.78 ng/mL with a minimum dilution of 1:10. The serum concentration-time data from each animal was analyzed using a two-compartment model with IV bolus input, first-order elimination, and macro-rate constants (Model 8, WinNonlin Pro v.5.0.1, Pharsight Corporation, Mountain View, Calif.). Overall goodness of fit was based on the predicted estimate, standard error for the prediction, and percentage of coefficient of variation for primary and secondary parameters, as well as inspection of residual plots between observed and predicted concentration-time data. Individual primary PK parameters comprised the zero-time intercepts (A and B) associated with the alpha and beta phases, respectively, and the micro-rate constants (alpha and beta). The following modeling options were used: Initial estimates were determined using WinNonlin; Concentrations were weighted by the reciprocal of the predicted concentration squared ($1/\hat{y}^2$); Nelder-Mead minimization algorithm was used.

Results of 28-day pharmacokinetics analyses in rats are shown in FIG. 12. Rats were dosed with 0.5 mg/kg body weight of thio ch3A5-VC-MMAE or ch 3A5-VC-MMAE. Serum from rats was collected at 5 minutes, 1 hour, 6 hours, 24 hours, and 2, 3, 4, 8, 11, 15, 21, and 28 days after dosing. The thio ch3A5-VC-MMAE showed slower kinetics of in vivo clearance, in terms of total antibody or in terms of drug-conjugated antibody. This behavior could be advantageous for improving exposure to the therapeutic in the course of treating a malignancy or other disorder while reducing the potentially deleterious effects of cytotoxic drug clearance through rapid-clearance pathways including metabolism.

Animal Toxicity

The safety of cysteine engineered anti-MUC16 antibody-drug conjugates was evaluated in an acute toxicity rat model. Toxicity of ADC was investigated by treatment of female Sprague-Dawley rats with the ADC and subsequent inspection and analysis of the effects on various organs. Based on gross observations (body weights), clinical pathology parameters (serum chemistry and hematology) and histopathology, the toxicity of ADC may be observed, characterized, and measured. It was found that at equivalent dose levels, cysteine engineered anti-MUC16 antibody-drug conjugates were associated with less acute toxicity than the corresponding standard antibody-drug conjugates.

A 12 day acute toxicity study in adolescent female rats (100-125 gms) was conducted by a single injection of: std ch 3A5-VC-MMAE (24.19 mg/kg=1934 μg/m$^2$), thio ch 3A5-VC-MMAE (49.99 mg/kg=1934 μg/m$^2$), and a control Vehicle at day 1. Std ch 3A5 is the parent chimeric anti-MUC16 antibody called 3A5, and thio ch 3A5 is the cysteine engineered chimeric anti-MUC16 3A5 antibody. Body weight was measured daily. Clinical chemistry, serum enzymes and hematology analysis was conducted on days 5 and 12; concluding with complete necropsy with histopathological assessment. Toxicity signals included the clinical observation of weight loss.

Figure 13:
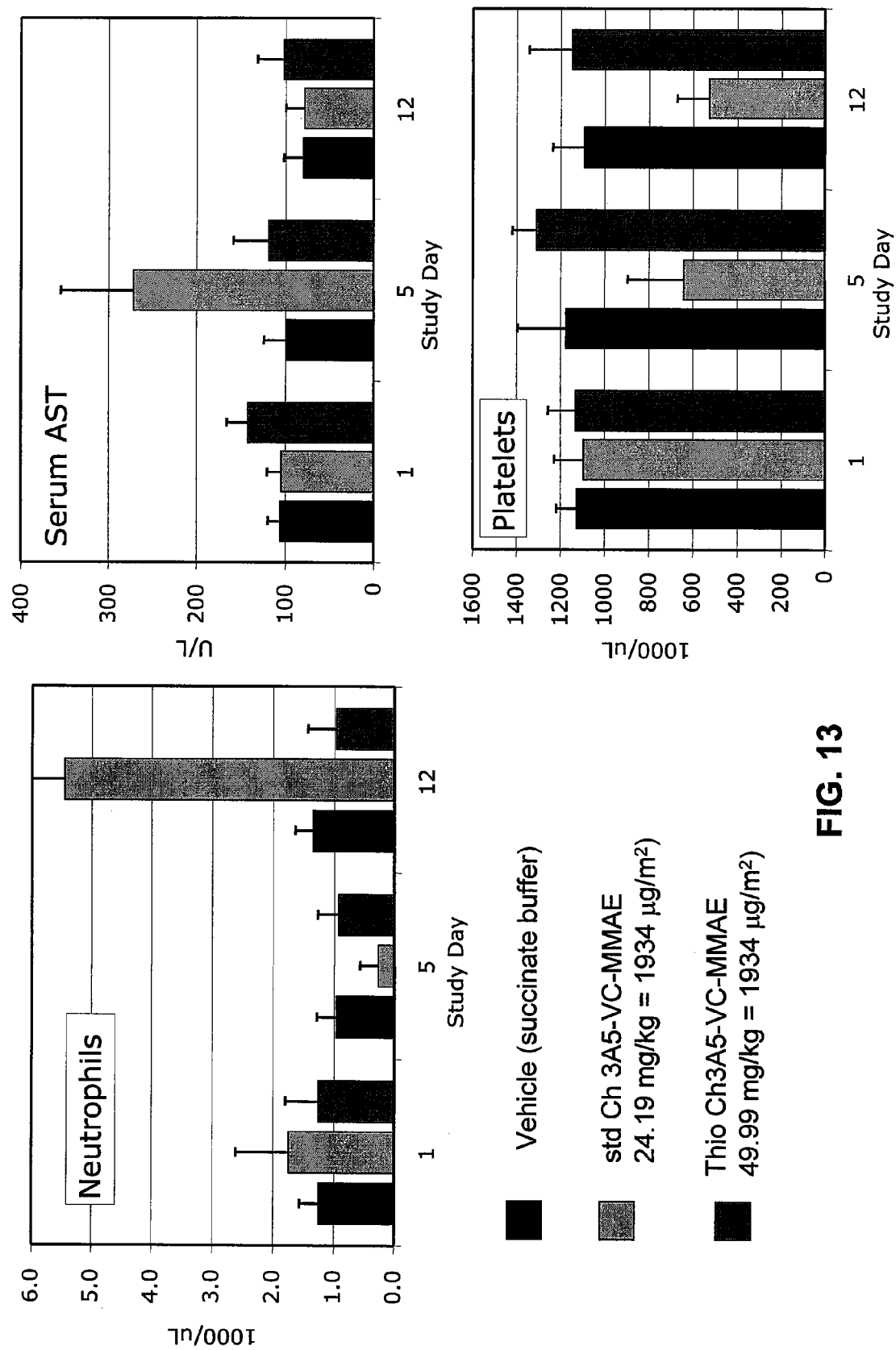
FIG. 13 shows the toxicities of ch 3A5-VC-MMAE and thio ch3A5-VC-MMAE at 1934 µg/m$^2$ exposure of cytotoxic drug in rats by measurement of neutrophils (top left), serum AST (top right), and platelets (bottom right).
Figure 14:
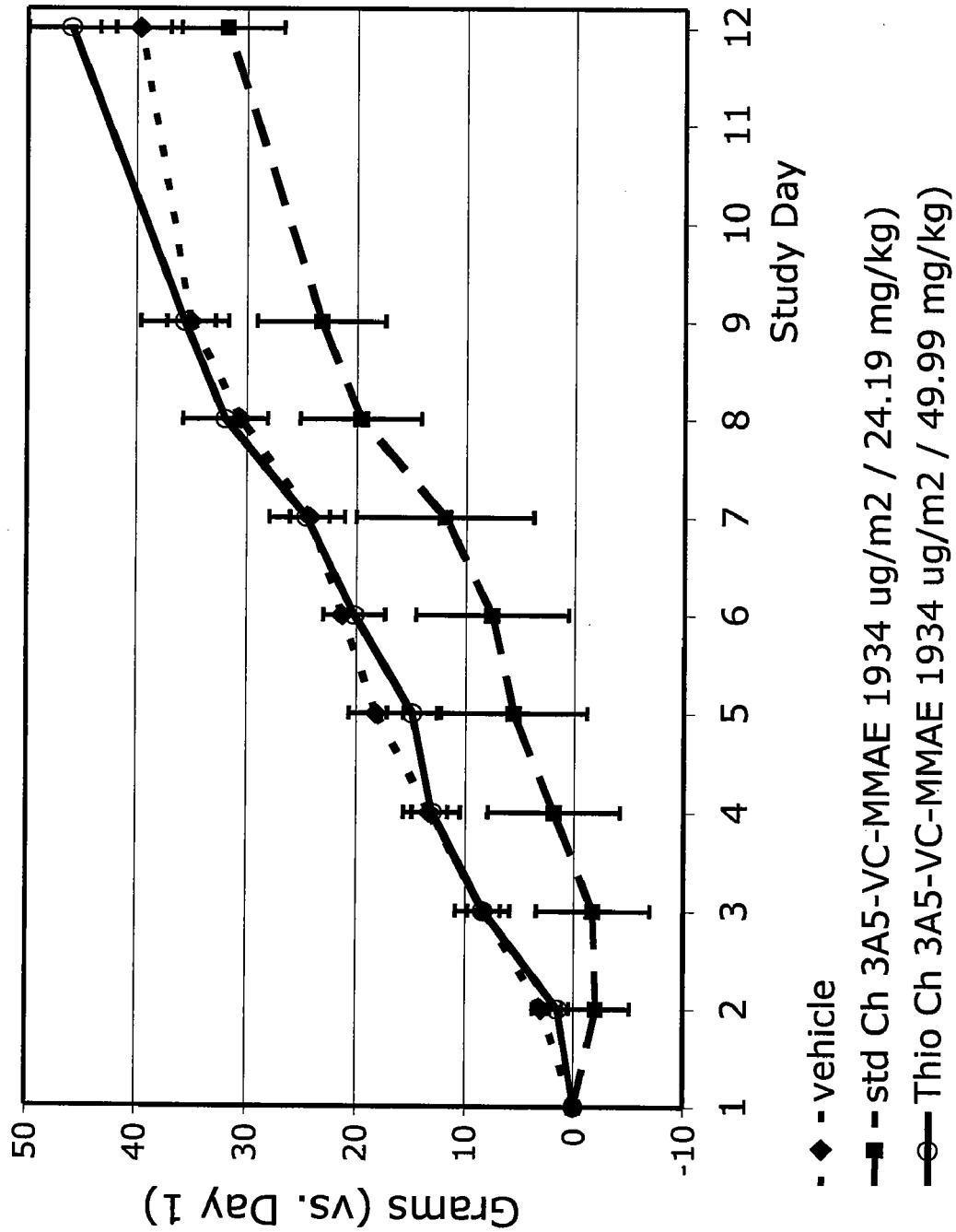
FIG. 14 shows the change in body weight over time of rats (6/group) dosed with: Vehicle (succinate buffer); 24.19 mg/kg=1934 µg/m$^2$ ch 3A5-VC-MMAE; 49.99 mg/kg=1934 µg/m$^2$ thio ch3A5-VC-MMAE.

Hepatotoxicity was measured by elevated liver enzymes in the serum, including aspartate aminotransferase (AST), alanine aminotransferase (ALT), and g-glutamyl transferase (GGT). Hematolymphoid toxicity was observed by depletion of leukocytes, primarily granuloctyes (neutrophils), and/or platelets, and lymphoid organ involvement, i.e. atrophy or apoptotic activity. It was found that the cysteine engineered anti-MUC16 antibody-drug conjugates caused no detectable changes in serum AST levels or in the levels of circulating platelets or neutrophils as compared with vehicle-treated animals. These findings are presented in FIG. 13. In contrast, the standard anti-MUC16 antibody-drug conjugate, at the same dose of cytotoxic drug and half the dose of antibody, produced transient elevation in AST and depletion of neutrophils and platelets in the circulation (observed at Day 5). Elevations in serum AST and GGT were also observed. The cysteine-engineered antibody conjugation technology appears to improve the safety of the antibody-drug conjugate in the rodent model. In rats, a single dose of 16.6 mg/kg standard anti-MUC16 ADC (equivalent to 1500 µg/m² drug exposure) produced a marked depletion of circulating neutrophils and other white blood cells at Day 5 (four days post-dose; FIG. 13), followed by a compensatory rebound at Day 12. This standard ADC dose also led to a mild elevation in serum levels of the liver enzyme aspartate aminotransferase (AST; FIG. 13) and transient weight loss (FIG. 14). The AST levels were more profoundly affected by a 50% increase in dose (24.5 mg/kg ADC; 2250 µg/m MMAE). At that dose, three of six rats did not survive to study termination (Day 12). In contrast, 36.4 mg/kg of thio anti-MUC16 ADC (equivalent to 1500 µg/m² drug exposure) yielded no adverse effects, with all parameters essentially identical to vehicle-treated animals. A dose of 68.6 mg/kg thio anti-MUC16 ADC (2820 µg/m² drug) produced toxicities that were nearly equivalent to those observed using the standard anti-MUC16 antibody-drug conjugate at one-fourth that dose. Importantly, while the highest thio anti-MUC16 ADC dose (100.8 mg/kg; 4150 µg/m² drug) did lead to pronounced effects, the overall profile of adverse effects was quite similar to that observed at the higher standard anti-MUC16 ADC dose (24.5 mg/kg ADC; 2250 µg/m² MMAE). The same trends were observed in a preliminary study using chimeric conjugates.

It is considered that weight loss, or weight change relative to animals dosed only with Vehicle in animals after dosing with ADC, is a gross and general indicator of systemic or localized toxicity. FIG. 14 shows the changes in body weight (grams) over 12 days. Rats receiving the cysteine-engineered conjugate gained weight at the same rate as vehicle-treated animals, whereas rats receiving the standard antibody-drug conjugate experienced a transient loss of body weight or a delay in weight gain.

The safety of standard and thio anti-MUC16 antibody-drug conjugates was also evaluated in cynomolgus monkey. Although both rat and monkey species express MUC16 recognized by the 3A5 antibody, the cynomolgus monkey antigen is more similar to the human antigen with respect to primary sequence. In a competitive binding assay, MAb 3A5 binding to CAI25 was inhibited with similar concentrations human and monkey MUC16 ECD proteins (IC50=0.76 nM and 1.89 nM, respectively), but competition by the rat MUC16 ECD was much less efficient (IC50=13.5 nM). Both rat and cynomolgus monkey are sensitive to antibody-MMAE conjugates. Pilot studies in cynomolgus monkeys have essentially echoed the findings in rats. The most significant adverse event in primates dosed with standard and thio anti-MUC16-MC-vc-PAB-MMAE ADC is a reversible decrease in neutrophils. Whereas a marked decrease was induced by the standard anti-MUC16-MC-vc-PAB-MMAE ADC at a drug exposure of 1200 µg/m² drug (5.9 mg/kg antibody), the thio ADC at 1200 µg/m² drug (12.8 mg/kg antibody) yielded no notable adverse events, with neutrophil counts tracking closely with sham-treated animals (FIG. 17). Animals were dosed at days 1 and 22. The 22 day neutrophil levels were pre-second dose. Doubling the dose to 25.6 mg/kg; 2400 µg/m² drug resulted in decreased neutrophil counts which were completely reversible. An even higher dose of thio anti-MUC16 ADC (38.4 mg/kg; 3600 µg/m² drug) gave no marked effects beyond the neutrophil decrease, which was more pronounced than at the medium dose level but remained reversible. Importantly, no toxicities were observed in organs known to express MUC16 (including cornea, lung, oviduct, and uterus). The only notable histopathologic findings in monkeys dosed with the TDC were minimal to mild increases in bone marrow myelopoiesis and minimal to mild thymic lymphoid depletion, consistent with the neutrophil decreases and indicative of a regenerative response. These results demonstrate that the thio ADC is safer than the standard ADC in preclinical models, even when compared on the basis of cytotoxic drug dose (i.e., equivalent µg/m²).

In vivo Activity Assays

The efficacy of the cysteine engineered anti-MUC16 antibody-drug conjugates were measured in vivo by implanting allografts or xenografts of cancer cells in rodents and treating the tumors with ADC. Variable results are to be expected depending on the cell line, the specificity of antibody binding of the ADC to receptors present on the cancer cells, dosing regimen, and other factors. The in vivo efficacy of the ADC was measured using a transgenic explant mouse model expressing moderate levels of MUC16. Subjects were treated once with ADC and monitored over 3-6 weeks to measure the time to tumor doubling, log cell kill, and tumor shrinkage. Follow up dose-response and multi-dose experiments were conducted.

Figure 15:
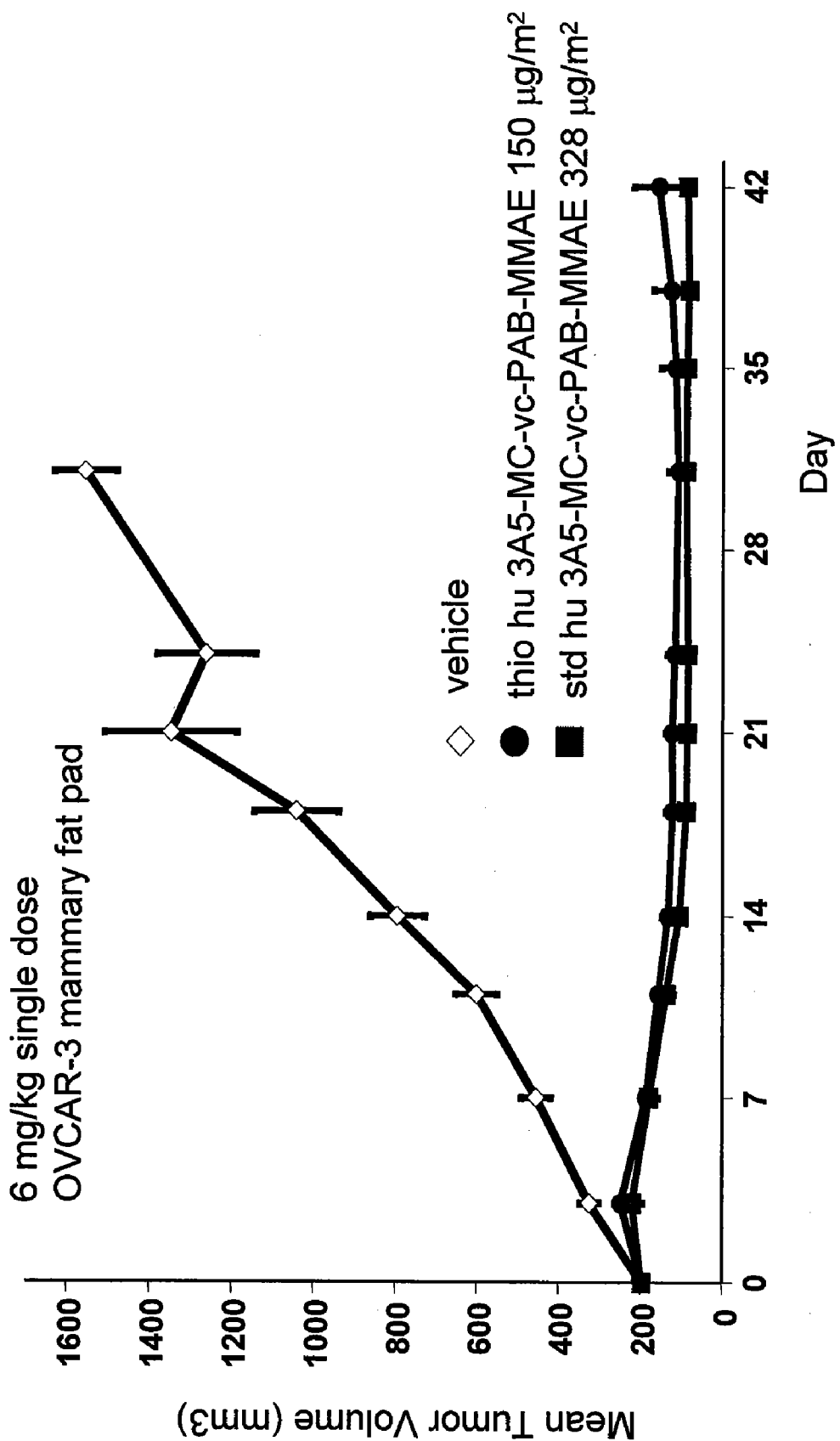
FIG. 15 shows the in vivo mean tumor volume change over time in SCID beige mice with an OVCAR-3 mammary fat pad after a single dose of: Vehicle (10 mL/kg succinate buffer); 6 mg/kg=328 µg/m2 std hu 3A5-MC-vc-PAB-MMAE, 3.5 MMAE/Ab loading; or 6 mg/kg=150 µg/m2 thio hu 3A5-MC-vc-PAB-MMAE, 1.6 MMAE/Ab loading.
Figure 16:
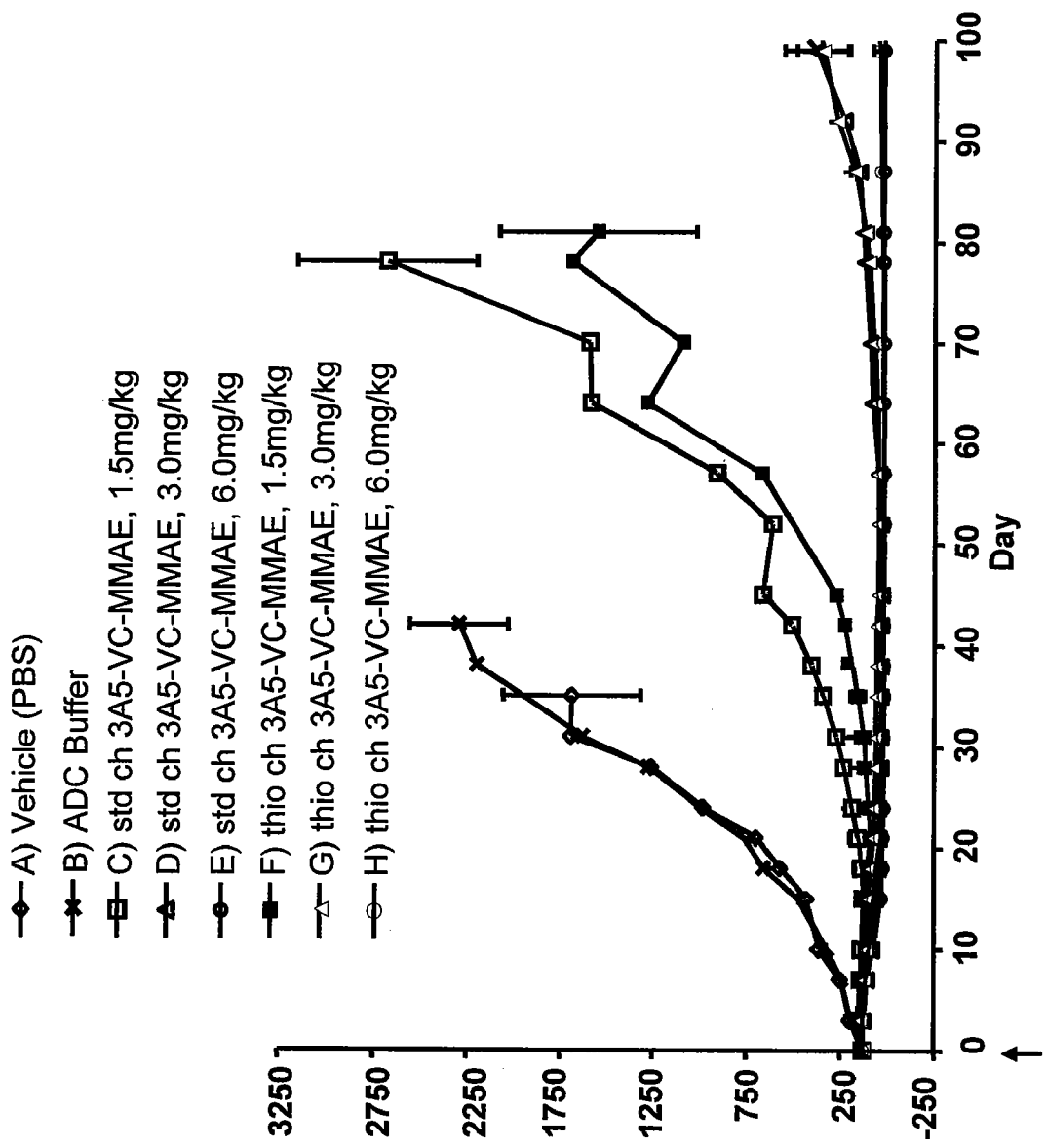
FIG. 16 shows the in vivo mean tumor volume change over time in SCID beige mice with an OVCAR-3 mammary fat pad tumor after a single dose of: A) Vehicle (PBS); B) ADC buffer; C) std ch 3A5-MC-vc-PAB-MMAE, 1.5 mg/kg; D)

FIGS. 15 and 16 show the activities of the cysteine-engineered anti-MUC16 drug conjugates compared with standard conjugates against OVCAR-3 tumor cells transplanted into the mammary fat pads of female SCID mice. Tumors were established and allowed to grow to 150-200 mm³ in volume (as measured using calipers) before a single treatment on day 0. Tumor volume was measured using calipers according to the formula: V (mm³)=0.5A×B², where A and B are the long and short diameters, respectively. Mice were euthanized before tumor volume reached 3000 mm³ or when tumors showed signs of impending ulceration. Data collected from each experimental group (10 mice per group) were expressed as mean±SE. FIG. 15 shows the comparable activities of 6 mg/kg doses of std hu 3A5-VC-MMAE (328 mg/m² drug dose) and thio hu3A5-VC-MMAE (150 mg/m² drug dose). FIG. 16 compares the chimeric conjugates, applying doses of 1.5, 3, and 6 mg/kg; the cysteine-engineered and standard conjugates exhibited comparable activities at each dose level. The data are summarized in tabular form below.

| Table for FIG. 15 | | | | | |
|---|---|---|---|---|---|
| | PR | CR | mg/kg | µg/m² | drug/Ab |
| Vehicle (PBS) | 0 | 0 | — | — | — |
| Std Hu 3A5-MC-VC-PAB-MMAE | 8 | 0 | 6 | 328 | 3.5 |
| Thio Hu 3A5-MC-VC-PAB-MMAE | 8 | 0 | 6 | 150 | 1.6 |

* Std Hu 3A5 is the parent chimeric anti-MUC16 antibody called 3A5, and Thio Hu 3A5 is the cysteine engineered chimeric anti-MUC16 3A5 antibody.

Table for FIG. 16

|  | PR | CR | mg/kg | µg/m² | drug/Ab |
|---|---|---|---|---|---|
| Vehicle (PBS) | 0 | 0 | — | — | — |
| ADC buffer | 0 | 0 | — | — | — |
| std ch 3A5-MC-vc-PAB-MMAE | 1 | 0 | 1.5 | 71 | 3.1 |
| std ch 3A5-MC-vc-PAB-MMAE | 2 | 6 | 3 | 141 | 3.1 |
| std ch 3A5-MC-vc-PAB-MMAE | 4 | 6 | 6 | 283 | 3.1 |
| thio ch 3A5-MC-vc-PAB-MMAE | 1 | 1 | 1.5 | 35 | 1.5 |
| thio ch 3A5-MC-vc-PAB-MMAE | 4 | 3 | 3 | 69 | 1.5 |
| thio ch 3A5-MC-vc-PAB-MMAE | 3 | 7 | 6 | 139 | 1.5 |

* Std ch 3A5 is the parent chimeric anti-MUC16 antibody called 3A5, and thio ch 3A5 is the cysteine engineered chimeric anti-MUC16 3A5 antibody.

Thio ch 3A5-MC-vc-PAB-MMAE was at least as active as std ch 3A5-MC-vc-PAB-MMAE against a transplant xenograft model of ovarian cancer at each IgG dose level, providing partial efficacy at 1.5 mg/kg (MMAE doses are 35 µg/m² for thio ch 3A5-MC-vc-PAB-MMAE and 71 µg/m² for std ch 3A5-MC-vc-PAB-MMAE) and near-complete elimination of tumors at 3 mg/kg (69 vs. 141 µg/m² MMAE) and 6 mg/kg (139 vs. 283 µg/m² MMAE). When stated in terms of MMAE dose, thio ch 3A5-MC-vc-PAB-MMAE was approximately twice as efficacious as std ch 3A5-MC-vc-PAB-MMAE. No adverse effects of either conjugate were observed at any dose level.

Methods of Treatment

Another embodiment of the present invention is directed to a method of therapeutically treating a mammal having a cancerous tumor comprising cells that express a MUC16/CA125/O772P polypeptide, wherein the method comprises administering to the mammal a therapeutically effective amount of a cysteine engineered antibody, or antibody drug conjugate thereof, that binds to the MUC16/CA125/O772P polypeptide, thereby resulting in the effective therapeutic treatment of the tumor.

Another embodiment of the present invention is directed to a method for treating or preventing a cell proliferative disorder associated with altered, preferably increased, expression or activity of a MUC16/CA125/O772P polypeptide, the method comprising administering to a subject in need of such treatment an effective amount of a cysteine engineered anti-MUC16 antibody, or antibody drug conjugate thereof. An exemplary cell proliferative disorder is cancer. Effective treatment or prevention of the cell proliferative disorder may be a result of direct killing or growth inhibition of cells that express a MUC16/CA125/O772P polypeptide or by antagonizing the cell growth potentiating activity of a MUC16/CA125/O772P polypeptide with the cysteine engineered anti-MUC16 antibody, or antibody drug conjugate thereof.

Yet another embodiment of the present invention is directed to a method of binding a cysteine engineered anti-MUC16 antibody, or antibody drug conjugate thereof, to a cell that expresses a MUC16/CA125/O772P polypeptide, wherein the method comprises contacting a cell that expresses a MUC16/CA125/O772P polypeptide with said cysteine engineered anti-MUC16 antibody, or antibody drug conjugate thereof, under conditions which are suitable for binding of the cysteine engineered anti-MUC16 antibody, or antibody drug conjugate thereof, to said MUC16/CA125/O772P polypeptide and allowing binding therebetween. In preferred embodiments, the cysteine engineered anti-MUC16 antibody, or antibody drug conjugate thereof, is labeled with a molecule or compound that is useful for qualitatively and/or quantitatively determining the location and/or amount of binding of the cysteine engineered anti-MUC16 antibody, or antibody drug conjugate thereof, to the cell.

Other embodiments of the present invention are directed to the use of a cysteine engineered anti-MUC16 antibody, or antibody drug conjugate thereof, in the preparation of a medicament useful for (i) the therapeutic treatment or diagnostic detection of a cancer or tumor, or (ii) the therapeutic treatment or prevention of a cell proliferative disorder.

Another embodiment of the present invention is directed to a method for inhibiting the growth of a cancer cell, wherein the growth of said cancer cell is at least in part dependent upon the growth potentiating effect(s) of a MUC16/CA125/O772P polypeptide (wherein the CA125/O772P polypeptide may be expressed either by the cancer cell itself or a cell that produces polypeptide(s) that have a growth potentiating effect on cancer cells), wherein the method comprises contacting the MUC16/CA125/O772P polypeptide with a cysteine engineered anti-MUC16 antibody, or antibody drug conjugate thereof, thereby antagonizing the growth-potentiating activity of the MUC16/CA125/O772P polypeptide and, in turn, inhibiting the growth of the cancer cell, whereby the growth of the cancer cell is inhibited.

Another embodiment of the present invention is directed to a method of therapeutically treating a tumor in a mammal, wherein the growth of said tumor is at least in part dependent upon the growth potentiating effect(s) of a MUC16/CA125/O772P polypeptide, wherein the method comprises administering to the mammal a therapeutically effective amount of an anti-MUC16 cysteine engineered antibody, or antibody drug conjugate thereof, that binds to the MUC16/CA125/O772P polypeptide, thereby antagonizing the growth potentiating activity of said MUC16/CA125/O772P polypeptide and resulting in the effective therapeutic treatment of the tumor.

The antibodies, antibody fragments, and conjugates thereof recognize extracellular epitopes of plasma membrane MUC16 proteins that are released into the extracellular fluid. The invention further provides methods for the detection, monitoring and treatment of malignancies such as breast cancer and ovarian cancer using the antibodies, antibody fragments and conjugates.

Antibody-drug conjugates (ADC) of the present invention may be used to treat various diseases or disorders, e.g. characterized by the overexpression of a MUC16 tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

The ADC compounds which are identified in the animal models and cell-based assays can be further tested in tumor-bearing higher primates and human clinical trials. The clinical trial may be designed to evaluate the efficacy of an ADC in combinations with known therapeutic regimens, such as radiation and/or chemotherapy involving known chemotherapeutic and/or cytotoxic agents.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include ovarian cancer, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic adenocarcinoma, glioblastoma, cervical cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-MUC16 antibody. Other dosage regimens may be useful. The progress of this therapy is easily monitored by conventional techniques and assays including ultrasound imaging.

Administration of Antibody-Drug Conjugates

The antibody-drug conjugates (ADC) of the invention may be administered by any route appropriate to the condition to be treated. The ADC will typically be administered parenterally, i.e. infusion, subcutaneous, intraperitoneal, intramuscular, intravenous, intradermal, intrathecal and epidural.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage, sterile injectable form. An antibody-drug conjugate (ADC) having the desired degree of purity is optionally mixed with pharmaceutically acceptable diluents, carriers, excipients or stabilizers (*Remington's Pharmaceutical Sciences* (1980) 16th edition, Osol, A. Ed.), in the form of a lyophilized formulation or an aqueous solution.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are disfavored due to hydrolysis or denaturation in the gut, formulations of ADC suitable for oral administration may be prepared as discrete units such as capsules, cachets or tablets each containing a predetermined amount of the ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The compositions of the invention may also be formulated as liposomes; a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al (1985) Proc. Natl. Acad. Sci. USA 82:3688; Hwang et al (1980) Proc. Natl Acad. Sci. USA 77:4030; U.S. Pat. No. 4,485,045; U.S. Pat. No. 4,544,545; U.S. Pat. No. 5,013,556; WO 97/38731. Liposomes can be generated by the reverse phase evaporation method with a lipid composition comprising phosphatidylcholine, cholesterol and PEG-derivatized phosphatidylethanolamine (PEG-PE). Liposomes may be extruded through filters of defined pore size to yield liposomes with the desired diameter. Fab' fragments of the compositions of the present invention can be conjugated to liposomes (Martin et al (1982) J. Biol. Chem. 257:286-288), via a disulfide interchange reaction. A chemotherapeutic agent is optionally contained within the liposome (Gabizon et al (1989) J. National Cancer Inst. 81(19):1484.

Combination Therapy

An antibody-drug conjugate (ADC) of the invention may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an ADC of the invention may also have a therapeutically effective amount of a chemotherapeutic agent such as a tubulin-forming inhibitor, a topoisomerase inhibitor, a DNA intercalator, or a DNA binder.

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an ADC involves the combined administration of a cysteine engineered anti-MUC16 antibody or antibody-drug conjugate thereof, and one or more chemotherapeutic agents, therapeutic biological, or growth inhibitory agents, including coadministration of cocktails of different chemotherapeutic agents. Chemotherapeutic agents include, but are not limited to: taxanes (such as paclitaxel and docetaxel (TAXOTERE®); platinum-containing compounds, such as carboplatin; EGFR inhibitors such as erlotinib, and gefitinib; tyrosine kinase inhibitors such as imatinib; and anthracycline antibiotics (such as doxorubicin or doxil). Therapeutic biological agents to be used in combination with a cysteine engineered anti-MUC16 antibody or antibody-drug conjugate thereof include bevacizumab (Avastin®) or pertuzumab (Omnitarg™, Genentech Inc). Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

The ADC may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the ADC (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}$C or $^{3}$H) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Articles of Manufacture

In another embodiment of the invention, an article of manufacture, or "kit", containing materials useful for the treatment of the disorders described above is provided. The article of manufacture comprises a container and a label or package insert on or associated with the container. The package insert may refer to instructions customarily included in commercial packages of therapeutic products and that contain information about the indications, usage, dosage, administration, contraindications and/or warnings concerning the use of such therapeutic products. Suitable containers include, for example, bottles, vials, syringes, blister pack, etc. The containers may be formed from a variety of materials such as glass or plastic.

In one embodiment, the article of manufacture comprises a container and a formulation of a cysteine engineered anti-MUC16 antibody, or antibody-drug conjugate thereof, contained within the container. The article may further optionally comprise a label affixed to the container, or a package insert included with the container, that refers to the use of the composition of matter for the therapeutic treatment or diagnostic detection of a tumor. The container holding the formulation is effective for storing and delivering the therapeutic and may have a sterile access port (for example the container may be an intravenous solution bag or a vial having a stopper pierceable by a hypodermic injection needle). The label or package insert indicates that the formulation is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Preparation of Anti-MUC16 3A5 Antibodies

Humanized and chimeric 3A5 anti-Muc16 3A5 antibodies (FIGS. 3 and 4) were prepared according to WO 2007/001851, the sequences and antibodies of which are incorporated by reference.

Light chain amino acids are numbered according to Kabat (Kabat et al., *Sequences of proteins of immunological interest*, (1991) 5th Ed., US Dept of Health and Human Service, National Institutes of Health, Bethesda, Md.). Heavy chain amino acids are numbered according to the Eu numbering system (Edelman et al (1969) Proc. Natl. Acad of Sciences 63(1):78-85), except where noted as the Kabat system. Single letter amino acid abbreviations are used.

Humanized (thio hu) and chimeric (thio ch) cysteine engineered anti-MUC16 3A5 monoclonal antibodies as A117C variants were expressed and purified, including the two embodiments:

thio hu anti-MUC16 HC A117C 3A5: MW=144834.84; pI=8.28; pI(oxidized C)=8.79; Length=1320; Ext. Coef. (280)=1.61. Heavy Chain 446 aa; MW: 48952.23, pI: 8.55, pI(oxidized c): 9.12, Ext. Coeff. (280): 1.70; Potential Signal Sequence (MGWSCIILFLVATATGVHS, SEQ ID NO:41) trimmed off prior to calculations. Length=19; dna start position: 987, dna stop position: 2324, FIG. 1, SEQ ID NO:1. Light Chain 214 aa; MW: 23483.20, pI: 6.71, pI(oxidized c): 6.72, Ext. Coeff (280): 1.43; Potential Signal Sequence (MGWSCIILFLVATATGVHS, SEQ ID NO:41) trimmed off prior to calculations. Length=19; dna start position: 7103, dna stop position: 7744, FIG. 1, SEQ ID NO:2 thio ch anti-MUC16 HC A117C: MW=145118.9; pI=7.99; pI(oxidized C)=8.44; Length=1320; Ext. Coef. (280)=1.59. Heavy Chain 446 aa; MW: 49236.50, pI: 8.29, pI(oxidized c): 8.85, Ext. Coeff(280): 1.66; Potential Signal Sequence (MGWSCIILFLVATATGAYA, SEQ ID NO:42) trimmed off prior to calculations. Length=19; dna start position: 987, dna stop position: 2324, FIG. 2, SEQ ID NO:3. Light Chain 214 aa; MW: 23340.96, pI: 6.71, pI(oxidized c): 6.72, Ext. Coeff (280): 1.44; Potential Signal Sequence (MGWSCIILFLVATATGVHS, SEQ ID NO:41) trimmed off prior to calculations. Length=19; dna start position: 7103, dna stop position: 7744. FIG. 2, SEQ ID NO:4

Example 2

Preparation of Cysteine Engineered Anti-MUC16 Antibodies for Conjugation by Reduction and Reoxidation Full length, cysteine engineered anti-MUC16 monoclonal antibodies (ThioMabs) expressed in CHO cells bear cysteine adducts (cystines) or glutathionylated on the engineered cysteines due to cell culture conditions. To liberate the reactive thiol groups of the engineered cysteines, the ThioMabs are dissolved in 500 nM sodium borate and 500 mM sodium chloride at about pH 8.0 and reduced with about a 50-100 fold excess of 1 mM TCEP (tris(2-carboxyethyl)phosphine hydrochloride; Getz et al (1999) Anal. Biochem. Vol 273:73-80; Soltec Ventures, Beverly, Mass.) for about 1-2 hrs at 37° C. Alternatively, DTT can be used as reducing agent. The formation of inter-chain disulfide bonds was monitored either by non-reducing SDS-PAGE or by denaturing reverse phase HPLC PLRP column chromatography. The reduced ThioMab (FIG. 6a) is diluted and loaded onto a HiTrap S column in 10 mM sodium acetate, pH 5, and eluted with PBS containing 0.3M sodium chloride. The eluted reduced ThioMab is treated with 2 mM dehydroascorbic acid (dhAA) at pH 7 for 3 hours, or 2 mM aqueous copper sulfate ($CuSO_4$) at room temperature overnight. Ambient air oxidation may also be effective. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Theoretical masses for the three major glycoforms of the standard 3A5 antibody are: 147407, 147568 and 147731 Da. Observed masses in the deconvoluted mass spectrum of standard 3A5 antibody were 147410, 147569 and 147734 Da., in excellent agreement with the expected theoretical masses. Theoretical masses are 147469, 147631 and 147793 Da. for the three major glycoforms of the thio 3A5 antibody. Observed masses (heterogeneous and poorly resolved) of the thio-3A5 antibody in the deconvoluted mass spectrum were approximately 147774, 147904 and 148061. The heterogeneity is due to the presence of a mixture of capping groups (usually cysteine or glutathionine) on the two newly introduced cysteines.

Liquid chromatography/Mass Spectrometric Analysis was performed on a TSQ Quantum Triple quadrupole mass spectrometer with extended mass range (Thermo Electron, San Jose Calif.). Samples were chromatographed on a PRLP-S, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluant was directly ionized using the electrospray source. Data were collected by the Xcalibur data system and deconvolution was performed using ProMass (Novatia, LLC, New Jersey). Prior to LC/MS analysis, antibodies or drug conjugates (50 μg) were treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 μm, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody.

Example 3

Conjugation of Cysteine Engineered Anti-MUC16 Antibodies and Drug-Linker Intermediates After the reduction and reoxidation procedures of Example 2, the cysteine engineered anti-MUC16 antibody is dissolved in PBS (phosphate buffered saline) buffer and chilled on ice. About 1.5 molar equivalents relative to engineered cysteines per antibody of an auristatin drug linker intermediate, such as MC-MMAE (maleimidocaproyl-monomethyl auristatin E), MC-MMAF, MC-val-cit-PAB-MMAE, or MC-val-cit-PAB-MMAF, with a thiol-reactive functional group such as maleimido, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The reaction mixture is concentrated by centrifugal ultrafiltration and the cysteine engineered anti-MUC16 antibody drug conjugate is purified and desalted by elution through G25 resin in PBS, filtered through 0.2 μm filters under sterile conditions, and frozen for storage.

By the procedure above, the following cysteine engineered anti-MUC16 antibody drug conjugates were prepared:

thio hu 3A5-MC-MMAF by conjugation of A117C thio hu 3A5 and MC-MMAF;

thio hu 3A5-MC-val-cit-PAB-MMAE by conjugation of A117C thio hu 3A5 and MC-val-cit-PAB-MMAE;

thio ch 3A5-MC-MMAF by conjugation of A117C thio ch 3A5 and MC-MMAF; and thio ch 3A5-MC-val-cit-PAB-MMAE by conjugation of A117C thio ch 3A5 and MC-val-cit-PAB-MMAE.

Example 4

In vitro Cell Proliferation Assay

The in vitro potency of antibody-drug conjugates was measured by a cell proliferation assay (FIGS. 10 and 11). The CellTiter-Glo® Luminescent Cell Viability Assay is a commercially available (Promega Corp., Madison, Wis.), homogeneous assay method based on the recombinant expression of Coleoptera luciferase (U.S. Pat. No. 5,583,024; U.S. Pat. No. 5,674,713; U.S. Pat. No. 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium.

The homogeneous "add-mix-measure" format results in cell lysis and generation of a luminescent signal proportional to the amount of ATP present. The substrate, Beetle Luciferin, is oxidatively decarboxylated by recombinant firefly luciferase with concomitant conversion of ATP to AMP and generation of photons. Viable cells are reflected in relative luminescence units (RLU). Data can be recorded by luminometer or CCD camera imaging device. The luminescence output is presented as RLU, measured over time. Alternatively, photons from luminescence can be counted in a scintillation counter in the presence of a scintillant. The light units can be represented then as CPS—counts per second.

Efficacy of ADC were measured by a cell proliferation assay employing the following protocol, adapted from Cell-Titer Glo Luminescent Cell Viability Assay, Promega Corp. Technical Bulletin TB288 and Mendoza et al (2002) Cancer Res. 62:5485-5488:

1. An aliquot of 50 µl of cell culture containing about 1000 (PC3) or 3000 (OVCAR-3) cells: (1) a MUC16 polypeptide-expressing cell line OVCAR-3; (2) a PC3-derived cell line engineered to stably express MUC16 polypeptide on its cell surface (PC3/MUC16); and (3) a PC3 cell line that does not express MUC16 polypeptide (PC3/neo) in medium was deposited in each well of a 96-well, opaque-walled plate.

2. ADC (50 ml) was added to triplicate experimental wells to final concentration of 9000, 3000, 1000, 333, 111, 37, 12.4, 4.1, or 1.4 ng/mL, with "no ADC" control wells receiving medium alone, and incubated for 3 (PC3) or 5 (OVCAR-3) days.

3. The plates were equilibrated to room temperature for approximately 30 minutes.

4. CellTiter-Glo Reagent (100 ml) was added.

5. The contents were mixed for 2 minutes on an orbital shaker to induce cell lysis.

6. The plate was incubated at room temperature for 10 minutes to stabilize the luminescence signal.

7. Luminescence was recorded and reported in graphs as RLU=relative luminescence units. Data from cells incubated with ADC-free medium were plotted at 0.46 ng/ml.

Media: PC3/neo and PC3/MUC16 grow in DMEM+ Ham's F012/10% FBS/glutamine/250 µg/mL G-418
OVCAR-3 grow in RPMI/20% FBS/glutamine Example 5

Pharmacokinetics—Serum Clearance and Stability

The disposition of the anti-MUC16 antibody-drug conjugates in vivo was analyzed by measuring the serum concentrations of antibody and of drug conjugate after a single intravenous bolus dose into Sprague-Dawley rats. Concentrations of antibody-drug conjugates bearing at least one cytotoxic drug were measured with an ELISA that used a MUC16 extracellular domain (ECD) protein for the capture and anti-MMAE and horseradish peroxidase (HRP) conjugated anti-mouse Fc antibody for detection. Total Ch3A5 and ThioCh3A5 concentrations in serum were measured with an ELISA that used MUC16 ECD for capture and anti-human-Fc HRP for detection. This assay measured any anti-MUC16 antibody, both with and without conjugated MMAE. The assays have lower limits of quantitation of 0.78 ng/mL with a minimum dilution of 1:10. The assays have lower limits of quantitation of 0.78 ng/mL with a minimum dilution of 1:10. The serum concentration-time data from each animal was analyzed using a two-compartment model with IV bolus input, first-order elimination, and macro-rate constants (Model 8, WinNonlin Pro v.5.0.1, Pharsight Corporation, Mountain View, Calif.).

|     |                          | CL (mL/day/kg) | $T_{1/2} \beta$ (days) |
|-----|--------------------------|----------------|------------------------|
| ADC | Total antibody           | 16.1 ± 3.5     | 10.3 ± 2.1             |
|     | Drug-conjugated antibody | 41.6 ± 4.8     | 6.0 ± 0.9              |
| TDC | Total antibody           | 9.5 ± 2.9      | 7.9 ± 2.1              |
|     | Drug-conjugated antibody | 14.1 ± 3.0     | 5.5 ± 1.0              |

Example 6

Animal Toxicity

A 12 day acute toxicity study in adolescent female rats (100-125 gms) was conducted by a single injection of: standard ch 3A5-VC-MMAE (24.19 mg/kg=1934 µg/m²), thio ch3A5-VC-MMAE (49.99 mg/kg=1934 µg/m²), and a control Vehicle at day 1. Injection of test article was as an intravenous bolus. Body weight was measured daily. Clinical chemistry, serum enzymes and hematology analysis was conducted on days 5 and 12. Toxicity signals included the clinical observation of weight loss.

Higher doses of the thio ADC were required to reduce neutrophil counts in cynomolgus monkeys. In two separate studies, female Chinese cynomolgus monkeys were dosed on days 1 and 22 with: standard humanized anti-MUC16 ADC (5.9 mg/kg IgG=1200 µg/m² MMAE); thio ADC at 12.8 mg/kg IgG (1200 µg/m² MMAE); thio ADC at 25.6 mg/kg IgG (2400 µg/m² MMAE); or thio ADC at 38.4 mg/kg IgG (3600 µg/m² MMAE). Blood was drawn for hematology and serum chemistry days 8, 22, 32, and 43 (day 22 values are from before the second dose). Average circulating neutrophil counts were normalized to the average counts from vehicle-treated monkeys at the given time point of the same study. The nadir in neutrophil levels occurred approximately one week after dosing, followed by a recovery to normal levels within three weeks.

Example 7

Tumor Growth Inhibition, in Vivo Efficacy Mouse Model

Efficacy studies were performed using female C.B-17 SCID beige mice (Charles River Laboratories). All studies were conducted in accordance with the Guide for the Care and Use of Laboratory Animals (Institute of Laboratory Animal Resources, "Guide for the Care and Use of Laboratory Animals", (NIH Publication #85-23). Washington (D.C.): National Academy Press; 1996.). The OVCAR-3 mammary fat pad transplant efficacy model was employed as described (Chen et al. (2007) Cancer Res 67:4924-4932), evaluating tumor volume after a single intravenous dose.

The OVCAR-3 mammary fat pad transplant model was developed using tumors excised from a mouse bearing an intraperitoneal tumor, then serially passaged into the mammary fat pads of recipient mice. When tumors reached a volume of ~150-200 mm³, mice were separated into five groups of ten and dosed as described. Tumor volume was measured using calipers according to the formula: V (mm³)= 0.5A×B², where A and B are the long and short diameters, respectively. Mice were euthanized before tumor volume reached 3000 mm³ or when tumors showed signs of impending ulceration. Data collected from each experimental group were expressed as mean±SE.

To test the efficacy of the cysteine engineered anti-MUC16 antibody drug conjugates in vivo, $2\times10^7$ OVCAR-3 cells per SCID mouse (110 mice total) were inoculated once into the mammary fat pad and allowed to grow for 14-21 days post-injection. When tumor volumes reached 150-200 mm³ (typically Day 14 to Day 21 after inoculation), the mice were segregated into 8 different groups of 9-10 mice per group and the tumor volume was determined in each mouse, as follows:

| Group | Sample | dose |
| --- | --- | --- |
| A | Vehicle (PBS) | |
| B | ADC buffer | |
| C | std ch 3A5-MC-vc-PAB-MMAE | 1.5 mg/kg |
| D | std ch 3A5-MC-vc-PAB-MMAE | 3.0 mg/kg |
| E | std ch 3A5-MC-vc-PAB-MMAE | 6.0 mg/kg |
| F | thio ch 3A5-MC-vc-PAB-MMAE | 1.5 mg/kg |
| G | thio ch 3A5-MC-vc-PAB-MMAE | 3.0 mg/kg |
| H | thio ch 3A5-MC-vc-PAB-MMAE | 6.0 mg/kg |

Example 8

Flow Cytometry and in Vitro Studies

OVCAR-3 cells (30,000 cells per sample) were incubated on ice with humanized standard or thio anti-MUC16 MAb for 75 minutes in 1 mL total volume. Antibodies were applied at 25, 50, 100, 200, and 400 ng/mL in PBS+1% FBS+2 mM EDTA. After this incubation, cells were washed and then incubated with phycoerythrein-labeled goat anti-human Fc secondary antibody (one hour on ice). Cells were then washed and analyzed by flow cytometry. $3\times10^4$ OVCAR-3 cells express approximately $1\times10^{10}$ binding sites for anti-MUC16 antibody 3A5. Even the lowest antibody concentration tested (25 ng or approximately $1\times10^{11}$ antibodies) provides a molar excess of antibodies over binding sites. Therefore, the concentration at which binding is reduced (as detected by flow cytometry) reflect the affinity of the antibody for MUC16. Binding affinities of anti-MUC16 variants were determined by surface plasmon resonance and by enzyme-linked immunosorbent assays (ELISA) using conventional procedures.

We claim:

1. An isolated cysteine engineered anti-MUC16 antibody which binds to a MUC16 polypeptide comprising the heavy chain sequence of SEQ ID NO:1.

2. The cysteine engineered anti-MUC16 antibody of claim 1 prepared by a process comprising replacing the residue at position 117 in the heavy chain of a parent anti-MUC16 antibody by cysteine.

3. The cysteine engineered anti-MUC16 antibody of claim 1 further comprising the light chain sequence:

SEQ ID NO:2
DIQMTQSPSSLSASVGDRVTITCKASDLIHNWLAWYQQKPGKAFKLLIYG

ATSLETGVPSRFSGSGSGTDFTLTISSLQPEDFATYYCQQYWTTPFTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSFVTKSFNRGEC.

4. The cysteine engineered anti-MUC16 antibody of claim 2 wherein the parent anti-MUC16 antibody is selected from a monoclonal antibody, a bispecific antibody, a chimeric antibody, a human antibody, and a humanized antibody.

5. The cysteine engineered anti-MUC16 antibody of claim 1 which is a Fab fragment.

6. The cysteine engineered anti-MUC16 antibody of claim 1 which is produced in bacteria.

7. The cysteine engineered anti-MUC16 antibody of claim 1 which is produced in CHO cells.

8. A method of determining the presence of a MUC16 protein in a sample suspected of containing said protein, said method comprising the steps of:
 exposing said sample to the cysteine engineered anti-MUC16 antibody having the heavy chain sequence of SEQ ID NO:1, and;
 determining binding of said antibody to said MUC16 protein in said sample, wherein binding of the antibody to said protein is indicative of the presence of said protein in said sample.

9. The method of claim 8 wherein said sample is an ovarian, breast, lung, or pancreatic cancer cell.

10. The method of claim 8 wherein the antibody is covalently attached to a label selected from a fluorescent dye, a radioisotope, biotin, or a metal-complexing ligand.

11. The cysteine engineered anti-MUC16 antibody of claim 1 wherein the antibody is covalently attached to an auristatin drug moiety whereby an antibody-drug conjugate is formed.

12. An antibody-drug conjugate comprising a cysteine engineered anti-MUC16 antibody (Ab) which binds to a MUC16 polypeptide and comprising the heavy chain sequence of SEQ ID NO: 1, and an auristatin drug moiety (D) wherein the cysteine engineered anti-MUC16 antibody is attached through a free cysteine amino acid by a linker moiety (L) to D; the compound having Formula I:

$$Ab\text{-}(L\text{-}D)_p \quad\quad\quad I$$

where p is 1, 2, 3, or 4.

13. The antibody-drug conjugate compound of claim 12 wherein p is 2.

14. The antibody-drug conjugate compound of claim 12 wherein L has the formula:

$$-A_a-W_w-Y_y-$$

where:
A is a Stretcher unit covalently attached to a cysteine thiol of the cysteine engineered antibody (Ab);
a is 0 or 1;
each W is independently an Amino Acid unit;
w is an integer ranging from 0 to 12;
Y is a Spacer unit covalently attached to the drug moiety; and
y is 0, 1 or 2.

15. The antibody-drug conjugate compound of claim 14 having the formula:

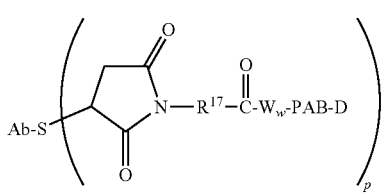

where PAB is para-aminobenzylcarbamoyl, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—$(C_3$-$C_8$ carbocyclyl), ($C_3$-$C_8$ carbocyclyl)-$(CH_2)_r$, $C_3$-$C_8$ heterocyclyl, $(CH_2)_r$—($C_3$-$C_8$ heterocyclyl), —($C_3$-$C_8$ heterocyclyl)-$(CH_2)_r$—, —$(CH_2)_rC(O)NR^b(CH_2)_r$—, —$(CH_2CH_2O)_r$—, —$(CH_2CH_2O)_r$—$CH_2$—, —$(CH_2)_rC(O)NR^b(CH_2CH_2O)_r$—, —$(CH_2)_rC(O)NR^b(CH_2CH_2O)_r$—$CH_2$—, —$(CH_2CH_2O)_rC(O)NR^b(CH_2CH_2O)_r$—, —$(CH_2CH_2O)_rC(O)NR^b(CH_2CH_2O)_r$—$CH_2$—, and —$(CH_2CH_2O)_rC(O)NR^b(CH_2)_r$—; where $R^b$ is H, $C_1$-$C_8$ alkyl, phenyl, or benzyl; and r is independently an integer ranging from 1 to 10.

16. The antibody-drug conjugate compound of claim 14 wherein $W_w$ is valine-citrulline.

17. The antibody-drug conjugate compound of claim 14 wherein $R^{17}$ is $(CH_2)_5$ or $(CH_2)_2$.

18. The antibody-drug conjugate compound of claim 14 having the formula:

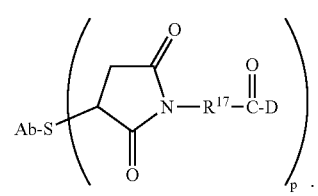

19. The antibody-drug conjugate compound of claim 18 wherein $R^{17}$ is $(CH_2)_5$ or $(CH_2)_2$.

20. The antibody-drug conjugate compound of claim 14 having the formula:

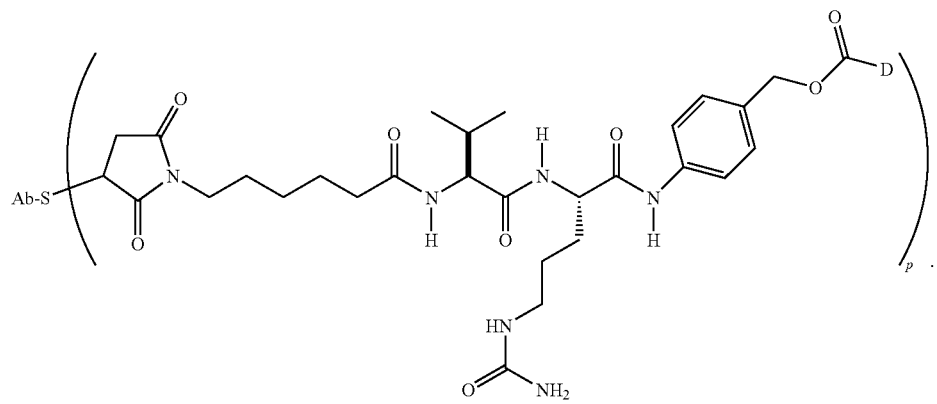

21. The antibody drug conjugate of claim 12 wherein L is MC-val-cit-PAB or MC.

22. The antibody-drug conjugate compound of claim 12 wherein L is a linker formed by linker reagents SMCC, BM(PEO)$_2$ or BM(PEO)$_3$.

23. The antibody-drug conjugate compound of claim 12 wherein D is MMAE, having the structure:

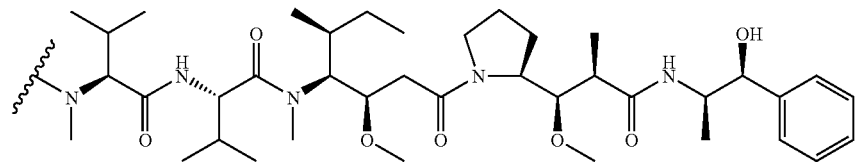

where the wavy line indicates the attachment site to the linker L.

24. The antibody-drug conjugate compound of claim 12 wherein D is MMAF, having the structure:

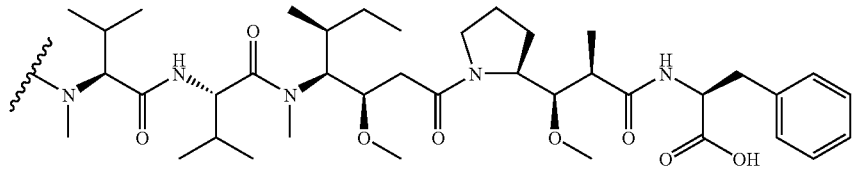

where the wavy line indicates the attachment site to the linker L.

25. The antibody-drug conjugate compound of claim 12 wherein the cysteine engineered anti-MUC16 antibody is selected from a monoclonal antibody, a bispecific antibody, a chimeric antibody, a human antibody, and a humanized antibody.

26. The antibody-drug conjugate compound of claim 12 wherein the cysteine engineered anti-MUC16 antibody is a Fab fragment.

27. An antibody-drug conjugate compound selected from the structures:

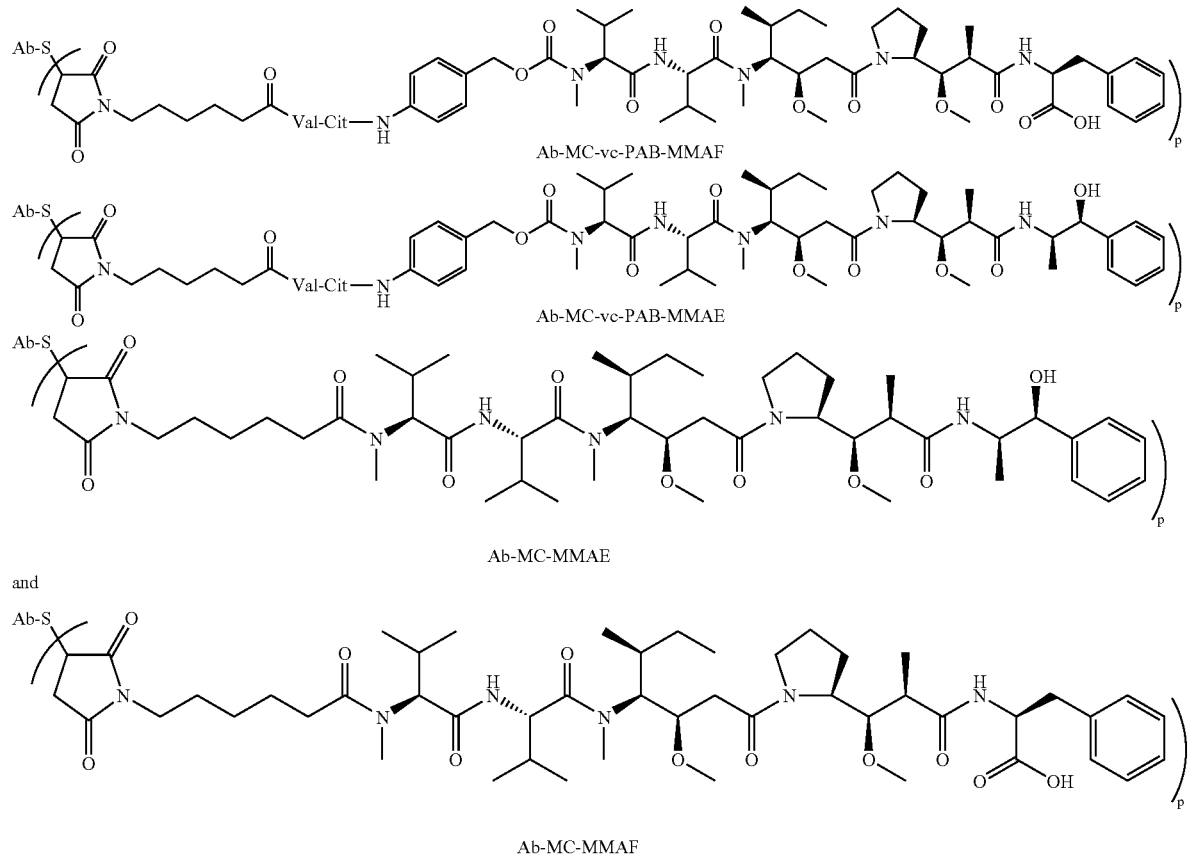

wherein Val is valine; Cit is citrulline; p is 1, 2, 3, or 4; and Ab is a cysteine engineered anti-MUC16 antibody which binds to a MUC16 polypeptide and comprising the heavy chain sequence of SEQ ID NO: 1.

28. The antibody drug conjugate of claim 27 wherein Ab further comprises SEQ ID NO: 2.

29. A mixture of antibody-drug conjugate compounds comprising a cysteine engineered anti-MUC16 antibody (Ab) which binds to a MUC16 polypeptide and comprising the heavy chain sequence of SEQ ID NO: 1, and an auristatin drug moiety (D) wherein the cysteine engineered anti-MUC16 antibody is attached through a free cysteine amino acid by a linker moiety (L) to D; the compound having Formula I:

$$Ab\text{-}(L\text{-}D)_p \quad\quad\quad I$$

where p is 1, 2, 3, or 4, and the average drug loading is from 1 to 2.

30. A pharmaceutical formulation comprising an antibody-drug conjugate comprising a cysteine engineered anti-MUC16 antibody which binds to a MUC16 polypeptide and comprising the heavy chain sequence SEQ ID NO: 1 and where the cysteine engineered anti-MUC16 antibody is covalently attached through a free cysteine amino acid to an auristatin drug moiety, and a pharmaceutically acceptable diluent, carrier or excipient.

31. The pharmaceutical formulation of claim 30 further comprising a therapeutically effective amount of a chemotherapeutic agent selected from letrozole, oxaliplatin, docetaxel, 5-FU, lapatinib, capecitabine, leucovorin, erlotinib, pertuzumab, bevacizumab, and gemcitabine.

32. A method of treating cancer comprising administering to a patient a pharmaceutical formulation comprising an antibody-drug conjugate comprising a cysteine engineered anti-MUC16 antibody which binds to a MUC16 polypeptide and having the heavy chain sequence of SEQ ID NO: 1 and where the cysteine engineered anti-MUC16 antibody is covalently attached through a free cysteine amino acid to an auristatin drug moiety, and a pharmaceutically acceptable diluent, carrier or excipient; and wherein the cancer is selected from the group consisting of ovarian cancer, prostate cancer, cancer of the urinary tract, pancreatic cancer, lung cancer, breast cancer, and colon cancer.

33. The method of claim 32 wherein the patient is administered a chemotherapeutic agent in combination with the antibody-drug conjugate compound, where the chemotherapeutic agent is selected from letrozole, cisplatin, carboplatin, taxol, paclitaxel, oxaliplatin, docetaxel, 5-FU, leucovorin, erlotinib, pertuzumab, bevacizumab, lapatinib, and gemcitabine.

34. An article of manufacture comprising
a pharmaceutical formulation comprising an antibody-drug conjugate comprising a cysteine engineered anti-MUC16 antibody which binds to a MUC16 polypeptide and having the heavy chain sequence of SEQ ID NO: 1 and where the cysteine engineered anti-MUC16 antibody is covalently attached through a free cysteine amino acid to an auristatin drug moiety, and a pharmaceutically acceptable diluent, carrier or excipient;
a container; and
a package insert or label indicating that the compound can be used to treat ovarian cancer, prostate cancer, cancer of the urinary tract, pancreatic cancer, lung cancer, breast cancer, or colon cancer characterized by the overexpression of a MUC16 polypeptide.

35. A method for making an antibody drug conjugate compound comprising a cysteine engineered anti-MUC16 antibody (Ab) which binds to a MUC16 polypeptide and having the heavy chain sequence of SEQ ID NO: 1, and an auristatin drug moiety (D) wherein the cysteine engineered antibody is attached through an engineered cysteine amino acid by a linker moiety (L) to D; the compound having Formula I:

$$Ab\text{-}(L\text{-}D)_p \qquad \qquad I$$

where p is 1, 2, 3, or 4; the method comprising the steps of:
(a) reacting an engineered cysteine group of the cysteine engineered antibody with a linker reagent to form antibody-linker intermediate Ab-L; and
(b) reacting Ab-L with an activated drug moiety D; whereby the antibody-drug conjugate compound is formed;
or comprising the steps of:
(c) reacting a nucleophilic group of a drug moiety with a linker reagent to form drug-linker intermediate D-L; and
(d) reacting D-L with an engineered cysteine group of the cysteine engineered antibody; whereby the antibody-drug conjugate compound is formed.

36. The method of claim 35 further comprising the step of expressing the cysteine engineered antibody in chinese hamster ovary (CHO) cells.

37. The method of claim 36 further comprising the step of treating the expressed cysteine engineered antibody with a reducing agent.

38. The method of claim 37 wherein the reducing agent is selected from TCEP and DTT.

39. The method of claim 38 further comprising the step of treating the expressed cysteine engineered antibody with an oxidizing agent, after treating with the reducing agent.

40. The method of claim 39 wherein the oxidizing agent is selected from copper sulfate, dehydroascorbic acid, and air.

* * * * *